(12) United States Patent
Joergensen et al.

(10) Patent No.: US 12,116,388 B2
(45) Date of Patent: Oct. 15, 2024

(54) AMYLIN RECEPTOR AGONISTS

(71) Applicant: Novo Nordisk A/S, Bagsvaerd (DK)

(72) Inventors: Cecilie Mia Joergensen, London (GB); Thomas Kruse, Herlev (DK); Jesper F. Lau, Farum (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 18/512,512

(22) Filed: Nov. 17, 2023

(65) Prior Publication Data
US 2024/0239852 A1    Jul. 18, 2024

(30) Foreign Application Priority Data
Dec. 22, 2022 (EP) .................................... 22215958

(51) Int. Cl.
*C07K 14/47* (2006.01)
*A61K 38/00* (2006.01)
*A61P 3/04* (2006.01)

(52) U.S. Cl.
CPC ............ *C07K 14/4705* (2013.01); *A61P 3/04* (2018.01); *A61K 38/00* (2013.01)

(58) Field of Classification Search
CPC .. C07K 14/4705; C07K 14/575; C07K 14/72; C07K 14/605; A61P 3/04; A61P 3/10; A61K 38/00; A61K 38/22
See application file for complete search history.

(56) References Cited

U.S. PATENT DOCUMENTS 5,622,839 A    4/1997    Moore et al.

FOREIGN PATENT DOCUMENTS

| WO | WO/1991/007978 | * | 6/1991 |
|----|----|----|----|
| WO | 2007/104789 A2 | | 9/2007 |
| WO | 2009/034119 A1 | | 3/2009 |
| WO | 2010/046357 A1 | | 4/2010 |
| WO | 2010/102886 A1 | | 9/2010 |
| WO | 2012168432 A1 | | 12/2012 |
| WO | 2013156594 A1 | | 10/2013 |
| WO | 15040182 A2 | | 3/2015 |
| WO | 15168488 A2 | | 11/2015 |
| WO | 16034604 A1 | | 3/2016 |
| WO | 2019149880 A1 | | 8/2019 |
| WO | 2019215063 A1 | | 11/2019 |
| WO | 22129254 A1 | | 6/2022 |
| WO | 2022129526 A1 | | 6/2022 |

OTHER PUBLICATIONS

Wineman-Fisher et al., Phys.Chem.Chem.Phys., 2016, 18, 12438-12442 (Year: 2016).*
Bower et al., "Molecular Signature for Receptor Engagement in the Metabolic Peptide Hormone Amylin," ACS Pharmacol. Transl. Sci., 2018, vol. 1, pp. 32-49.
Cao et al., "Commensal microbiota from patients with inflammatory bowel disease produce genotoxic metabolites", Science, Oct. 2022, vol. 378, No. 6618, pp. 1-11.
Enebo et al., "Safety, tolerability, pharmacokinetics, and pharmacodynamics of concomitant administration of multiple doses of cagrilintide with semaglutide 2•4 mg for weight management: a randomised, controlled, phase 1b trial", The Lancet, May 2021, vol. 397, No. 10286, pp. 1736-1748.
Lehninger et al., "Chapter 22—Molecular Mechanisms of Signal Transduction", Principles of Biochemistry, 1993, Second Edition, p. 762-767.
Sonne et al., "Mono and dual agonists of the amylin, calcitonin, and CGRP receptors and their potential in metabolic diseases", Mol. Metab. Nov. 2020, pp. 1-15.

* cited by examiner

*Primary Examiner* — Melissa L Fisher
*Assistant Examiner* — Joseph Fischer
(74) *Attorney, Agent, or Firm* — Rosemarie R. Wilk-Orescan

(57) ABSTRACT

The invention relates to a compound comprising an amylin receptor agonist. The invention also relates to a pharmaceutical composition, suitable for but not limited to oral administration, which comprises such a compound. The compound and pharmaceutical composition comprising it may be used for the medical treatment of subjects with overweight, obesity and associated co-morbidities.

15 Claims, No Drawings
Specification includes a Sequence Listing.

SEQUENCE LISTING

```
Sequence total quantity: 36
SEQ ID NO: 1              moltype = AA   length = 37
FEATURE                   Location/Qualifiers
source                    1..37
                          mol_type = protein
                          organism = Homo sapiens
SEQUENCE: 1
KCNTATCATQ RLANFLVHSS NNFGAILSST NVGSNTY                                37

SEQ ID NO: 2              moltype = AA   length = 37
FEATURE                   Location/Qualifiers
source                    1..37
                          mol_type = protein
                          organism = synthetic construct
SEQUENCE: 2
ASHLSTAQTQ RLAEFLHHSS DNFGPILPPT DVGSNTP                                37

SEQ ID NO: 3              moltype = AA   length = 33
FEATURE                   Location/Qualifiers
source                    1..33
                          mol_type = protein
                          organism = synthetic construct
SEQUENCE: 3
ASHLSTAQTQ RLAEFLHHFG PILPPTDVGS ETP                                    33

SEQ ID NO: 4              moltype = AA   length = 33
FEATURE                   Location/Qualifiers
source                    1..33
                          mol_type = protein
                          organism = synthetic construct
SEQUENCE: 4
ASHLSTAQTA RLAEFLHHFG PILPPTDVGS ETP                                    33

SEQ ID NO: 5              moltype = AA   length = 37
FEATURE                   Location/Qualifiers
source                    1..37
                          mol_type = protein
                          organism = synthetic construct
SEQUENCE: 5
ASHLSTAQTA RLAEFLHHSS DNFGPILPPT DVGSNTP                                37

SEQ ID NO: 6              moltype = AA   length = 37
FEATURE                   Location/Qualifiers
source                    1..37
                          mol_type = protein
                          organism = synthetic construct
SEQUENCE: 6
ASHLSTAQTQ RLAEFLHHSS DPFGAIPSST DVGPDTP                                37

SEQ ID NO: 7              moltype = AA   length = 37
FEATURE                   Location/Qualifiers
source                    1..37
                          mol_type = protein
                          organism = synthetic construct
SEQUENCE: 7
AGHLSTAQTQ RLAEFLHHSS DPFGAIPSST DVGPDTP                                37

SEQ ID NO: 8              moltype = AA   length = 37
FEATURE                   Location/Qualifiers
source                    1..37
                          mol_type = protein
                          organism = synthetic construct
SEQUENCE: 8
AGSLSTAQTQ RLAEFLHHSS DPFGAIPSST DVGPDTP                                37

SEQ ID NO: 9              moltype = AA   length = 37
FEATURE                   Location/Qualifiers
source                    1..37
                          mol_type = protein
                          organism = synthetic construct
SEQUENCE: 9
AGELSTAQTQ RLAEFLHHSS DPFGAIPSST DVGPDTP                                37

SEQ ID NO: 10             moltype = AA   length = 37
FEATURE                   Location/Qualifiers
source                    1..37
                          mol_type = protein
                          organism = synthetic construct
```

```
SEQUENCE: 10
ASNLATAQTQ RLAEFLHHSS DPFGAIPSST DVGPDTP                              37

SEQ ID NO: 11           moltype = AA  length = 37
FEATURE                 Location/Qualifiers
source                  1..37
                        mol_type = protein
                        organism = synthetic construct
SEQUENCE: 11
AGSLSTAQTA RLAEFLHHSS DNFGPILPPT DVGSNTP                              37

SEQ ID NO: 12           moltype = AA  length = 33
FEATURE                 Location/Qualifiers
source                  1..33
                        mol_type = protein
                        organism = synthetic construct
SEQUENCE: 12
AGSLSTAQTA RLAEFLHHFG PILPPTDVGS ETP                                  33

SEQ ID NO: 13           moltype = AA  length = 33
FEATURE                 Location/Qualifiers
source                  1..33
                        mol_type = protein
                        organism = synthetic construct
SEQUENCE: 13
AGELSTAQTA RLAEFLHHFG PILPPTDVGS ETP                                  33

SEQ ID NO: 14           moltype = AA  length = 37
FEATURE                 Location/Qualifiers
source                  1..37
                        mol_type = protein
                        organism = synthetic construct
SEQUENCE: 14
ASQLSTAQTQ RLAEFLHHSS DNFGKILPPT DVGSNTP                              37

SEQ ID NO: 15           moltype = AA  length = 37
FEATURE                 Location/Qualifiers
source                  1..37
                        mol_type = protein
                        organism = synthetic construct
SEQUENCE: 15
ASQLSTAQTQ RLAEFLHHSS DPFGKIPSST DVGPDTP                              37

SEQ ID NO: 16           moltype = AA  length = 37
FEATURE                 Location/Qualifiers
source                  1..37
                        mol_type = protein
                        organism = synthetic construct
SEQUENCE: 16
ASQLSTAQTA RLAEFLHHSS DNFGPILPPT DVGSNTP                              37

SEQ ID NO: 17           moltype = AA  length = 37
FEATURE                 Location/Qualifiers
source                  1..37
                        mol_type = protein
                        organism = synthetic construct
SEQUENCE: 17
ASALSTAQTA RLAEFLHHSS DNFGPILPPT DVGSNTP                              37

SEQ ID NO: 18           moltype = AA  length = 37
FEATURE                 Location/Qualifiers
source                  1..37
                        mol_type = protein
                        organism = synthetic construct
SEQUENCE: 18
ASQLSTAQTQ RLAEFLHHSS DPFGAIPSST DVGPDTP                              37

SEQ ID NO: 19           moltype = AA  length = 37
FEATURE                 Location/Qualifiers
source                  1..37
                        mol_type = protein
                        organism = synthetic construct
SEQUENCE: 19
ASHLSTAQTA RLAEFLHHSS DPFGAIPSST DVGPDTP                              37

SEQ ID NO: 20           moltype = AA  length = 37
FEATURE                 Location/Qualifiers
source                  1..37
                        mol_type = protein
```

-continued

```
                         organism = synthetic construct
SEQUENCE: 20
ASHLSTAQTQ RLAEFLHHSS DPFGAIPSST DVGPNTP                                    37

SEQ ID NO: 21            moltype = AA   length = 37
FEATURE                  Location/Qualifiers
source                   1..37
                         mol_type = protein
                         organism = synthetic construct
SEQUENCE: 21
ASHLSTAQTQ RLAEFLHHSS EPFGAIPSST EVGPETP                                    37

SEQ ID NO: 22            moltype = AA   length = 33
FEATURE                  Location/Qualifiers
source                   1..33
                         mol_type = protein
                         organism = synthetic construct
SEQUENCE: 22
ASELSTAQTQ RLAEFLHHFG PILPPTDVGS ETP                                        33

SEQ ID NO: 23            moltype = AA   length = 33
FEATURE                  Location/Qualifiers
source                   1..33
                         mol_type = protein
                         organism = synthetic construct
SEQUENCE: 23
AGSLSTAQTQ RLAEFLHHFG PILPPTDVGS ETP                                        33

SEQ ID NO: 24            moltype = AA   length = 33
FEATURE                  Location/Qualifiers
source                   1..33
                         mol_type = protein
                         organism = synthetic construct
SEQUENCE: 24
ASHLSTAQTQ RLAEFLHHFG PILPPTDVGS ETY                                        33

SEQ ID NO: 25            moltype = AA   length = 37
FEATURE                  Location/Qualifiers
source                   1..37
                         mol_type = protein
                         organism = synthetic construct
SEQUENCE: 25
ASHLSTLQTQ RLAEFLHHSS DPFGAIPSST DVGPDTP                                    37

SEQ ID NO: 26            moltype = AA   length = 37
FEATURE                  Location/Qualifiers
source                   1..37
                         mol_type = protein
                         organism = synthetic construct
SEQUENCE: 26
ASHLSTLQTQ RLAEFLHHSS DNFGPILPPT DVGSNTP                                    37

SEQ ID NO: 27            moltype = AA   length = 33
FEATURE                  Location/Qualifiers
source                   1..33
                         mol_type = protein
                         organism = synthetic construct
SEQUENCE: 27
ASHLSTLQTQ RLAEFLHHFG PILPPTDVGS ETP                                        33

SEQ ID NO: 28            moltype = AA   length = 37
FEATURE                  Location/Qualifiers
source                   1..37
                         mol_type = protein
                         organism = synthetic construct
SEQUENCE: 28
ASHLSTAQTQ RLAEFLHHSS DPFGAIPSST DVGPDTY                                    37

SEQ ID NO: 29            moltype = AA   length = 37
FEATURE                  Location/Qualifiers
source                   1..37
                         mol_type = protein
                         organism = synthetic construct
SEQUENCE: 29
ASHLSTAQTA RLAEFLHHSS DPFGAIPSST DVGPDTY                                    37

SEQ ID NO: 30            moltype = AA   length = 37
FEATURE                  Location/Qualifiers
source                   1..37
```

```
                            mol_type = protein
                            organism = synthetic construct
SEQUENCE: 30
ASHLSTAQTA RLAEFLHHSS DNFGPILPPT DVGSNTY                              37

SEQ ID NO: 31               moltype = AA   length = 37
FEATURE                     Location/Qualifiers
source                      1..37
                            mol_type = protein
                            organism = synthetic construct
SEQUENCE: 31
ASHLSTAQTA RLAEFLHHSS DPFGKIPSST DVGPDTP                              37

SEQ ID NO: 32               moltype = AA   length = 37
FEATURE                     Location/Qualifiers
source                      1..37
                            mol_type = protein
                            organism = synthetic construct
SEQUENCE: 32
ASHLSTAQTA RLAEFLHHSS DNFGKILPPT DVGSNTP                              37

SEQ ID NO: 33               moltype = AA   length = 33
FEATURE                     Location/Qualifiers
source                      1..33
                            mol_type = protein
                            organism = synthetic construct
SEQUENCE: 33
ASHLSTAQTA RLAEFLHHFG PILPPTDVGS ETY                                  33

SEQ ID NO: 34               moltype = AA   length = 37
FEATURE                     Location/Qualifiers
source                      1..37
                            mol_type = protein
                            organism = synthetic construct
SEQUENCE: 34
KCNTATCATQ RLAEFLRHSS NNFGPILPPT NVGSNTP                              37

SEQ ID NO: 35               moltype = AA   length = 37
FEATURE                     Location/Qualifiers
source                      1..37
                            mol_type = protein
                            organism = synthetic construct
SEQUENCE: 35
KCNTATCATQ RLANFLVHSS NNFGPILPPT NVGSNTY                              37

SEQ ID NO: 36               moltype = AA   length = 37
FEATURE                     Location/Qualifiers
source                      1..37
                            mol_type = protein
                            organism = synthetic construct
VAR_SEQ                     2
                            note = S or G
VAR_SEQ                     3
                            note = N, H, S, Q, A or E
VAR_SEQ                     5
                            note = A or S
VAR_SEQ                     7
                            note = A or L
VAR_SEQ                     10
                            note = Q or A
VAR_SEQ                     19
                            note = s or absent
VAR_SEQ                     20
                            note = S or absent
VAR_SEQ                     21
                            note = D, E or absent
VAR_SEQ                     22
                            note = S or P
VAR_SEQ                     25
                            note = A, K or P
VAR_SEQ                     27
                            note = L or P
VAR_SEQ                     28
                            note = S or P
VAR_SEQ                     29
```

```
                      note = S or P
VAR_SEQ             31
                      note = D or E
VAR_SEQ             34
                      note = S or P
VAR_SEQ             35
                      note = N, D or E
VAR_SEQ             37
                      note = Y or P
SEQUENCE: 36
AXXLXTXQTX RLAEFLHHXX XXFGXIXXXT XVGXXTX                    37
```

AMYLIN RECEPTOR AGONISTS

TECHNICAL FIELD

The invention relates to compounds that are dual acting amylin and calcitonin receptor agonists. The invention also relates to a pharmaceutical composition, suitable for, but not limited to, oral administration, which comprises the above-mentioned compounds. The compounds and pharmaceutical composition comprising it may be used for the medical treatment of individuals with overweight or obesity, with or without associated comorbidities; diabetes cardiovascular diseases, non-alcoholic steatohepatitis (NASH) and cognitive impairment, such as that caused by Alzheimer's disease.

CROSS-REFERENCE TO RELATED APPLICATIONS

This application claims priority to European Patent Application 22215958.4, filed Dec. 22, 2022; the contents of which are incorporated herein by reference.

INCORPORATION-BY-REFERENCE OF THE SEQUENCE LISTING

The instant application contains a Sequence Listing which has been submitted in XML format via the USPTO patent electronic filing system and is hereby incorporated by reference in its entirety. Said XML file, created on Nov. 16, 2023, is named 220032US01_SeqList.xml and is 39 kilobytes in size.

BACKGROUND

Overweight and obesity are the abnormal or excessive accumulation of body fat that present a risk to an individual's overall health. A body mass index (BMI) over 25 is classified as overweight, and a BMI of over 30 is classified obese. Obesity is a leading risk factor in numerous serious conditions, including type 2 diabetes and its associated co-morbidities, and cardiovascular diseases such as heart disease and stroke, which are the leading causes of death worldwide. Obesity is now recognized by the World Health Organization (WHO) as an issue that has grown to epidemic proportion, even in children. In 2016, 1.9 billion adults worldwide were reportedly obese; in 2019, 38.3 million children under the age of 5 worldwide were reportedly obese. According to the WHO, 422 million people worldwide have diabetes and 1.6 million deaths are directly attributed to diabetes each year. There is, therefore, a huge incentive for the individual, as well as society, for preventing and/or treating obesity.

When diet and exercise alone do not suffice in reducing the body mass index (BMI) of an obese individual to an acceptable level, treatment with pharmaceutical drugs such as liraglutide, semaglutide, orlistat and naltrexone-bupropion have been shown to cause some weight loss. Nonetheless, bariatric surgery has proven necessary in many cases. While bariatric surgery is currently the most effective treatment in terms of obtaining long-term weight loss, it is an invasive procedure associated with high risk to the patient and high cost. Therefore, an efficacious and minimally invasive treatment would be a significant improvement in the treatment of obesity.

Amylin is a 37-amino acid long polypeptide hormone that is produced in and co-secreted with insulin from the pancreatic beta (β)-cell. Endogenous amylin has a half-life of approximately 15-20 minutes. It produces its effects in several different organ systems, primarily acting via amylin receptors 1-3 (AMYR1-3). Amylin is an important regulator of energy metabolism in health and disease, inhibiting glucagon secretion, delaying gastric emptying, signaling satiety, and suppressing appetite. Other amylin actions have also been reported, such as on the cardiovascular system and on bone.

Clinical studies have shown that amylin receptor agonists may be useful for the treatment of overweight, obesity, type 1 diabetes and/or type 2 diabetes. Currently, there is one product on the market (Symlin®) which contains an amylin receptor agonist (pramlintide acetate) as the active pharmaceutical ingredient. Symlin®, a liquid pharmaceutical formulation for subcutaneous administration, is approved for use in patients with type 1 or type 2 diabetes who use basal and mealtime insulin and have failed to achieve desired glycemic control, despite optimal insulin therapy. Pramlintide for use in overweight and obese patients was also investigated in the clinic. Pramlintide has a short biological half-life (less than 1 hour), necessitating administration thrice daily. Consequently, there is a large diurnal difference in the pramlintide plasma levels of patients treated with it.

A fixed-dose combination of an amylin receptor agonist, cagrilintide, and a GLP-1 receptor agonist, semaglutide, is currently under investigation for the treatment of overweight and obesity (Lancet 2021; 397: 1736-48). The drug products being investigated are separate liquid pharmaceutical formulations for subcutaneous use. A clinical trial has demonstrated that a combination of semaglutide and cagrilintide induced a greater weight loss in obese patients than the maximal approved dose of semaglutide monotherapy, without resulting in a significant worsening of the side-effect profile. While semaglutide has successfully been formulated for oral administration, cagrilintide may not necessarily provide sufficient bioavailability for such route of administration. An alternative orally available amylin receptor agonist for monotherapy or combination with, but not limited to, semaglutide could therefore prove useful.

Whilst current therapy options and investigatory drugs provide promise, individuals with overweight, obesity and/or associated comorbidities can, at best, hope to be treated with injectable pharmaceutical formulations or medications with modest efficacy. There still remains a need in the art for a more efficacious medicament, which does not result in a proportionally increased level of side-effects and which is suitable for oral administration. It is therefore an object of the present invention to provide an amylin receptor agonist with bioavailability suitable for oral administration.

SUMMARY

The object as outlined above is achieved by the aspects of the present invention. In addition, the present invention may also solve further problems, which will be apparent from the disclosure of the exemplary embodiments.

In an aspect of the present invention is provided an amylin receptor agonist comprising a peptide according to Formula I (SEQ ID NO: 36):

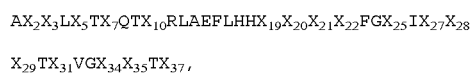

wherein
$X_2$ is S or G
$X_3$ is N, H, S, Q, A or E $X_5$ is A or S
$X_7$ is A or L
$X_{10}$ is Q or A
$X_{19}$ is S or absent
$X_{20}$ is S, or absent
$X_{21}$ is D, E or absent
$X_{22}$ is N, P or absent
$X_{25}$ is A, K or P
$X_{27}$ is L or P
$X_{28}$ is S or P
$X_{29}$ is S or P
$X_{31}$ is D or E
$X_{34}$ is S or P
$X_{35}$ is N, D or E
$X_{37}$ is Y or P,
wherein the peptide comprises a C-terminal amide.

In an embodiment, the peptide of the amylin receptor agonist is an amylin analogue. The amylin receptor agonist according to Formula I may be considered a modified human amylin analogue without the disulfide bridge that normally spans from positions 2 to 7 of native human amylin. Accordingly, in a preferred embodiment the amylin receptor agonist according to the present invention does not comprise a disulfide bridge. While it has generally been believed that an intact ring structure in amylin is necessary for full bioactivity (ACS Pharmacol. Transl. Sci. 2018, 1, 32.49) the present inventors have surprisingly found that compounds according to Formula I remain potent. The amylin receptor agonist comprises a peptide with alanine (Ala, A) at position 1, leucine (Leu, L) at position 4, and threonine (Thr, T) at position 6. Furthermore, the peptide comprises serine (Ser, S) or glycine (Gly, G) at position 2, asparagine (Asn, N), histidine (His, H), serine (Ser, S), glutamine (Gln, Q), alanine (Ala, A), or glutamic acid (Glu, E) at position 3, alanine (Ala, A) or serine (Ser, S) at position 5, and alanine (Ala, A) or leucine (Leu, L) at position 7. Furthermore, the peptide comprises glutamine (Gln, Q) at position 8. Without being bound by any particular theory it is believed that the substitutions introduced at the N-terminus sequence of the peptide allow for the entire human amylin analogue to retain potency while not having an intact ring structure. Accordingly, the human amylin analogue according to Formula I maintains a threonine (Thr, T) at position 9, arginine (Arg, R), leucine (Leu, L), and alanine (Ala, A) at positions 11 to 13, respectively, phenylalanine (Phe, F) and leucine (Leu, L) at positions 15 and 16, respectively, histidine (His, H) at position 18, phenylalanine (Phe, F) and glycine (Gly, G) at positions 23 and 24, respectively, isoleucine, (Ile, I) at position 26, threonine, (Thr, T) at position 30, valine (Val, V) and glycine (Gly, G) at positions 32 and 33, respectively, and threonine, (Thr, T) at position 36. Retaining full bioactivity without a disulfide bridge is considered highly advantageous as it enables a more robust production of the amylin receptor agonist. It is further believed that compounds without a disulfide bridge have improved stability in a liquid formulation for s.c. dosing. Accordingly, in an embodiment the amylin receptor agonist provides an improved stability in a liquid formulation. The present inventors further found that the compounds not having a disulfide bridge may be formulated at an approximate neutral pH range, which may facilitate coformulation with other compounds having the same or similar preferred pH range.

The amylin receptor agonist according to Formula I comprises glutamine at position 8. The present inventors have found that amylin receptor agonists comprising this substitution are highly potent on both the amylin and calcitonin receptors (with $EC_{50}$ values in the low pM range). Furthermore, the compounds comprising the substitution proved potent in reducing food intake in rats. Accordingly, in an embodiment the amylin receptor agonist according to Formula I provides an improved effect in reduction in food intake.

In an embodiment, the amylin receptor agonist is according to Formula I with the proviso that at least two of the amino acids at positions 21, 31 and 35 are an aspartic acid or a glutamic acid. The present inventors have observed that the amylin receptor agonist in a SNAC formulation has a high bioavailability in dogs following oral dosing. Accordingly, in an embodiment the amylin receptor agonist provides an improved bioavailability in oral administration.

In an embodiment, the amylin receptor agonist further comprises a protraction moiety attached via an alanine (Ala, A) residue at position 1 or a lysine (Lys, K) residue at position 25. The compounds disclosed herein exhibit a long half-life compared to their native ligands. In an embodiment, the amylin receptor agonist possesses a long biological half-life, relative to dosing interval, thus reducing the variability in steady state exposure.

In an embodiment, the amylin receptor agonist may exhibit a variety of properties rendering it useful as a medicament, as described herein. Accordingly, an aspect of the present invention relates to the amylin receptor agonist for use as a medicament. An embodiment relates to the amylin receptor agonist for use in the treatment of subjects with: an initial body mass index (BMI) of 27 or more, such as 30 or more, optionally in the presence of at least one weight-related comorbidity; diabetes, optionally in the presence of at least one comorbidity; cardiovascular disease; non-alcoholic steatohepatitis; and/or cognitive impairment, such as that caused by Alzheimer's disease.

A further aspect of the present invention relates to a pharmaceutical composition comprising the amylin receptor agonist and pharmaceutically acceptable excipients.

In yet another aspect of the present invention is provided a pharmaceutical co-composition comprising the amylin receptor agonist as disclosed herein and one or more peptide (s), such as but not limited to an insulin peptide, or a GLP-1 peptide, such as but not limited to semaglutide, liraglutide, or tirzepatide.

SEQUENCE LISTING

The present application is filed with a Sequence Listing in electronic form. The entire content of the sequence listing is hereby incorporated by reference.

SEQ ID NO: 1 represents the amino acid sequence of human amylin (1-37).

SEQ ID NOS: 2-33 represent the amino acid sequences of the peptides in compounds 2-43.

SEQ ID NO: 34 represents the amino acid sequence of the polypeptide backbone within cagrilintide.

SEQ ID NO: 35 represents the amino acid sequence of the polypeptide backbone within pramlintide.

SEQ ID NO: 36 represents the amino acid sequence of Formula I.

| Compound number | SEQ ID NO | |
|---|---|---|
| Peptide backbone in human amylin | 1 | KCNTATCATQRLANFLVHSSNNFGAILSSTNVGSNTY |
| Peptide backbone in Compound 2 | 5 | ASHLSTAQTARLAEFLHHSSDNFGPILPPTDVGSNTP |
| Peptide backbone in Compound 3 | 2 | ASHLSTAQTQRLAEFLHHSSDNFGPILPPTDVGSNTP |
| Peptide backbone in Compound 4 | 3 | ASHLSTAQTQRLAEFLHHFGPILPPTDVGSETP |
| Peptide backbone in Compound 5 | 4 | ASHLSTAQTARLAEFLHHFGPILPPTDVGSETP |
| Peptide backbone in Compound 6 | 6 | ASHLSTAQTQRLAEFLHHSSDPFGAIPSSTDVGPDTP |
| Peptide backbone in Compound 7 | 7 | AGHLSTAQTQRLAEFLHHSSDPFGAIPSSTDVGPDTP |
| Peptide backbone in Compound 8 | 6 | ASHLSTAQTQRLAEFLHHSSDPFGAIPSSTDVGPDTP |
| Peptide backbone in Compound 9 | 6 | ASHLSTAQTQRLAEFLHHSSDPFGAIPSSTDVGPDTP |
| Peptide backbone in Compound 10 | 8 | AGSLSTAQTQRLAEFLHHSSDPFGAIPSSTDVGPDTP |
| Peptide backbone in Compound 11 | 9 | AGELSTAQTQRLAEFLHHSSDPFGAIPSSTDVGPDTP |
| Peptide backbone in Compound 12 | 10 | ASNLATAQTQRLAEFLHHSSDPFGAIPSSTDVGPDTP |
| Peptide backbone in Compound 13 | 11 | AGSLSTAQTARLAEFLHHSSDNFGPILPPTDVGSNTP |
| Peptide backbone in Compound 14 | 5 | ASHLSTAQTARLAEFLHHSSDNFGPILPPTDVGSNTP |
| Peptide backbone in Compound 15 | 12 | AGSLSTAQTARLAEFLHHFGPILPPTDVGSETP |
| Peptide backbone in Compound 16 | 13 | AGELSTAQTARLAEFLHHFGPILPPTDVGSETP |
| Peptide backbone in Compound 17 | 4 | ASHLSTAQTARLAEFLHHFGPILPPTDVGSETP |
| Peptide backbone in Compound 18 | 14 | ASQLSTAQTQRLAEFLHHSSDNFGKILPPTDVGSNTP |
| Peptide backbone in Compound 19 | 15 | ASQLSTAQTQRLAEFLHHSSDPFGKIPSSTDVGPDTP |
| Peptide backbone in Compound 20 | 5 | ASHLSTAQTARLAEFLHHSSDNFGPILPPTDVGSNTP |
| Peptide backbone in Compound 21 | 2 | ASHLSTAQTQRLAEFLHHSSDNFGPILPPTDVGSNTP |
| Peptide backbone in Compound 22 | 16 | ASQLSTAQTARLAEFLHHSSDNFGPILPPTDVGSNTP |
| Peptide backbone in Compound 23 | 17 | ASALSTAQTARLAEFLHHSSDNFGPILPPTDVGSNTP |
| Peptide backbone in Compound 24 | 18 | ASQLSTAQTARLAEFLHHSSDPFGAIPSSTDVGPDTP |
| Peptide backbone in Compound 25 | 19 | ASHLSTAQTARLAEFLHHSSDPFGAIPSSTDVGPDTP |
| Peptide backbone in Compound 26 | 20 | ASHLSTAQTQRLAEFLHHSSDPFGAIPSSTDVGPNTP |

| Compound number | SEQ ID NO | |
|---|---|---|
| Peptide backbone in Compound 27 | 21 | ASHLSTAQTQRLAEFLHHSSEPFGAIPSSTEVGPETP |
| Peptide backbone in Compound 28 | 3 | ASHLSTAQTQRLAEFLHHFGPILPPTDVGSETP |
| Peptide backbone in Compound 29 | 22 | ASELSTAQTQRLAEFLHHFGPILPPTDVGSETP |
| Peptide backbone in Compound 30 | 23 | AGSLSTAQTQRLAEFLHHFGPILPPTDVGSETP |
| Peptide backbone in Compound 31 | 3 | ASHLSTAQTQRLAEFLHHFGPILPPTDVGSETP |
| Peptide backbone in Compound 32 | 24 | ASHLSTAQTQRLAEFLHHFGPILPPTDVGSETY |
| Peptide backbone in Compound 33 | 25 | ASHLSTLQTQRLAEFLHHSSDPFGAIPSSTDVGPDTP |
| Peptide backbone in Compound 34 | 26 | ASHLSTLQTQRLAEFLHHSSDNFGPILPPTDVGSNTP |
| Peptide backbone in Compound 35 | 27 | ASHLSTLQTQRLAEFLHHFGPILPPTDVGSETP |
| Peptide backbone in Compound 36 | 28 | ASHLSTAQTQRLAEFLHHSSDPFGAIPSSTDVGPDTY |
| Peptide backbone in Compound 37 | 29 | ASHLSTAQTARLAEFLHHSSDPFGAIPSSTDVGPDTY |
| Peptide backbone in Compound 38 | 30 | ASHLSTAQTARLAEFLHHSSDNFGPILPPTDVGSNTY |
| Peptide backbone in Compound 39 | 19 | ASHLSTAQTARLAEFLHHSSDPFGAIPSSTDVGPDTP |
| Peptide backbone in Compound 40 | 31 | ASHLSTAQTARLAEFLHHSSDPFGKIPSSTDVGPDTP |
| Peptide backbone in Compound 41 | 32 | ASHLSTAQTARLAEFLHHSSDNFGKILPPTDVGSNTP |
| Peptide backbone in Compound 42 | 33 | ASHLSTAQTARLAEFLHHFGPILPPTDVGSETY |
| Peptide backbone in Compound 43 | 4 | ASHLSTAQTARLAEFLHHFGPILPPTDVGSETP |

DESCRIPTION

It is noted that all headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed.

The compounds disclosed herein may be a potent amylin receptor agonist with desirable properties, such as being suitable for oral administration. In a first aspect the present invention relates to an amylin receptor agonist comprising a peptide according to Formula I (SEQ ID NO: 36):

$$AX_2X_3LX_5TX_7QTX_{10}RLAEFLHHX_{19}X_{20}X_{21}X_{22}FGX_{25}IX_{27}X_{28}X_{29}TX_{31}VGX_{34}X_{35}TX_{37},$$

wherein $X_2$ is S or G, $X_3$ is N, H, S, Q, A or E, $X_5$ is A or S, $X_7$ is A or L, $X_{10}$ is Q or A, $X_{19}$ is S or absent, $X_{20}$ is S, or absent, $X_{21}$ is D, E or absent, $X_{22}$ is N, P or absent, $X_{25}$ is A, K or P, $X_{27}$ is L or P, $X_{28}$ is S or P, $X_{29}$ is S or P, $X_{31}$ is D or E, $X_{34}$ is S or P, $X_{35}$ is N, D or E, $X_{37}$ is Y or P, wherein the peptide comprises a C-terminal amide.

General Definitions

Unless otherwise stated, all technical and scientific terms used herein have the same meanings as commonly understood by one of ordinary skill in the art to which this invention belongs. The practice of the present invention employs, unless otherwise indicated, conventional methods of chemistry, biochemistry, biophysics, molecular biology, cell biology, genetics, immunology and pharmacology, known to those skilled in the art.

The term "peptide" or "peptide sequence", as used herein refers to a compound which comprises a series of two or more amino acids interconnected via amide (or peptide) bonds. The term peptide is used interchangeably with the term "polypeptide" and the term "protein".

The term "analogue" as used herein generally refers to a polypeptide, the sequence of which has one or more amino acid changes as compared to a reference amino acid sequence. Said amino acid changes may include amino acid additions, amino acid deletions, and/or amino acid substitutions. Amino acid substitutions, deletions and/or additions may also be referred to as "mutations". In particular embodiments, an analogue "comprises" specified changes. In other particular embodiments, an analogue "consists of" or "has" specified changes. When the term "comprises" or "comprising" is used in relation to amino acid changes in an analogue, the analogue may have further amino acid changes as compared to its reference sequence. When the term "consisting of" or "has" is used in relation to amino acid changes in an analogue, the specified amino acid mutations are the only amino acid changes in the analogue as compared to the reference sequence.

The term "compound" as used herein refers to a molecular entity, and "compounds" may thus have different structural elements besides the minimum element defined for each compound or group of compounds. The term compound is used interchangeably with the term "construct". The term "compound" may be used to describe an amylin receptor agonist of the invention. The compounds of the invention may be referred to as "compound", and the term "compound" is also meant to cover pharmaceutically relevant forms hereof, i.e. the invention relates to a compound as defined herein or a pharmaceutically acceptable salt, amide, or ester thereof.

The term "derivative" generally refers to a chemically modified peptide in which one or more substituents or protraction moieties are covalently linked to the amino acid sequence of the peptide, such as via a bond to the alpha position of the alanine (Ala, A) at position 1 or to the epsilon position of a lysine (Lys, K) at position 25.

Amino Acids

Amino acids are molecules containing an amine group and a carboxylic acid group, and, optionally, one or more additional groups, often referred to as a side chain. The term "amino acid" includes canonical amino acids (which are genetically encoded), and unnatural amino acids. Non-limiting examples of unnatural amino acids are Aib (α-aminoisobutyric acid) and the D-isomers of the canonical amino acids. All amino acid residues within the polypeptide for which the optical isomer is not stated is herein to be understood to mean the L-isomer, unless otherwise specified.

Receptor Agonist

A "receptor agonist" or "agonist" is a ligand, such as a compound, that binds to and activates a biological receptor to produce a biological response. A full agonist may be defined as being one that elicits a response of the same magnitude as the natural ligand (see e.g. "Principles of Biochemistry", A L Lehninger, D L Nelson, M M Cox, Second Edition, Worth Publishers, 1993, page 763). Receptors can be activated by either endogenous agonists, such as endogenous hormones, or exogenous agonists, such as pharmaceutical drugs.

Amylin Receptor

An amylin receptor agonist may activate or agonize the calcitonin receptors (CTRs) and/or the amylin receptors (AMYRs). Amylin receptors consist of heterodimers of two components: the calcitonin receptor (CTR) and one of three receptor activity-modifying proteins (RAMP1-3), resulting in three possible complexes, AMYR1-3. Unless otherwise specified herein, "amylin receptor" at least refers to amylin receptor 3 (AMYR3). Nonetheless, some concomitant activity on the other receptors can be expected.

Amylin Receptor Agonists

The compounds disclosed herein comprise an amylin receptor agonist. An "amylin receptor agonist" may be defined as a chemical entity which is capable of binding to the amylin receptor and can activate it. In the context of the current invention, an "amylin receptor agonist" is capable of binding to and activating at least the AMYR3 complex. The amylin receptor agonist may also be capable of activating the calcitonin receptor and AMYR1-2.

Examples of endogenous amylin receptor agonists are human amylin and human calcitonin. Human amylin (SEQ ID No: 1) is a 37 amino acid long polypeptide having an amidated C-terminus and a disulfide bridge between cysteine residues 2 and 7. Both the amidated C-terminus and the disulfide bridge appear to be necessary for the full biological activity of amylin. Examples of exogenous amylin receptor agonists are pramlintide and cagrilintide (disclosed in WO 2012/168432).

In a preferred embodiment, the amylin receptor agonist according to the present invention is a potent amylin receptor agonist. In an embodiment, the amylin receptor agonist is a potent amylin receptor agonist and a potent calcitonin receptor agonist. The in vitro potency of the amylin receptor agonist on the amylin-3 receptor may be measured as described in the assay of Example 4. The potency of the compound may be described by means of its $EC_{50}$ values. $EC_{50}$ represents the concentration of compound upon which 50% of its maximal effect is observed. The lower the $EC_{50}$ value, the more potent the compound. The in vitro potency of the amylin receptor agonist on the calcitonin receptor may be measured as described in Example 4.

In an embodiment, when tested as described in the assay of Example 4 for amylin-3 receptor potency, the amylin receptor agonist disclosed herein has an $EC_{50}$ value of less than 300 pM, such as less than 200 pM, such as less than 150 pM, preferably less than 100 pM, such as less than 75 pM, even more preferably less than 50 pM, such as less than 40 pM, such as less than 30 pM, such as less than 20 pM, such as less than 10 pM, such as less than 7 pM, such as less than 5 pM, such as less than 3 pM, such as less than 2 pM. In a particular embodiment, the amylin receptor agonist has an $EC_{50}$ value of less than 10 pM, measured in an in vitro potency on the amylin-3 receptor according to the assay of Example 4.

In an embodiment, when tested as described in the assay Example 4 for calcitonin receptor potency, the amylin receptor agonist disclosed herein has an $EC_{50}$ value of less than 300 pM, such as less than 200 pM, such as less than 150 pM, preferably less than 100 pM, such as less than 75 pM, preferably less than 50 pM, such as less than 40 pM, such as less than 30 pM, such as less than 20 pM, such as less than 16 pM, such as less than 10 pM, such as less than 7 pM, such as less than 5 pM, such as less than 3 pM, such as less than 2 pM. In a particular embodiment, the amylin receptor agonist has an $EC_{50}$ value of less than 20 pM, measured in an in vitro potency on the calcitonin receptor according to the assay of Example 4.

Human Amylin Analogues

In an embodiment, the peptide of the amylin receptor agonist is an amylin analogue. The amylin receptor agonist disclosed herein comprises a peptide according to Formula I (SEQ ID NO: 36):

$AX_2X_3LX_5TX_7QTX_{10}RLAEFLHHX_{19}X_{20}X_{21}X_{22}FGX_{25}IX_{27}X_{28}$ $X_{29}TX_{31}VGX_{34}X_{35}TX_{37}$, wherein $X_2$ is S or G, $X_3$ is N, H, S, Q, A or E, $X_5$ is A or S, $X_7$ is A or L, $X_{10}$ is Q or A, $X_{19}$ is S or absent, $X_{20}$ is S, or absent, $X_{21}$ is D, E or absent, $X_{22}$ is N, P or absent, $X_{25}$ is A, K or P, $X_{27}$ is L or P, $X_{28}$ is S or P, $X_{29}$ is S or P, $X_{31}$ is D or E, $X_{34}$ is S or P, $X_{35}$ is N, D or E, $X_{37}$ is Y or P, wherein the peptide comprises a C-terminal amide.

In an embodiment, the amylin receptor agonist is according to Formula I, wherein $X_2$ is S or G, $X_3$ is H, S, Q or E, $X_5$ is S, $X_7$ is A, $X_{10}$ is Q or A, $X_{19}$ is S or absent, $X_{20}$ is S or absent, $X_{21}$ is D, E or absent, $X_{22}$ is N, P or absent, $X_{25}$ is A or P, $X_{27}$ is L or P, $X_{28}$ is S or P, $X_{29}$ is S or P, $X_{31}$ is D, $X_{34}$ is S or P, $X_{35}$ is N, D or E, and $X_{37}$ is P.

In an embodiment, the amylin receptor agonist is according to Formula I, wherein $X_2$ is S or G, $X_3$ is H, S, Q or E, $X_5$ is S, $X_7$ is A, $X_{10}$ is Q or A, $X_{19}$ is absent, $X_{20}$ is absent, $X_{21}$ is absent, $X_{22}$ is absent, $X_{25}$ is A or P, $X_{27}$ is L or P, $X_{28}$ is S or P, $X_{29}$ is S or P, $X_{31}$ is D, $X_{34}$ is S or P, $X_{35}$ is N, D or E, and $X_{37}$ is P.

In an embodiment, the amylin receptor agonist is according to Formula I, wherein $X_2$ is S or G, $X_3$ is H, S, or E, $X_5$ is S, $X_7$ is A, $X_{10}$ is Q or A, $X_{19}$ is absent, $X_{20}$ is absent, $X_{21}$ is absent, $X_{22}$ is absent, $X_{25}$ is P, $X_{27}$ is L, $X_{28}$ is P, $X_{29}$ is P, $X_{31}$ is D, $X_{34}$ is S, $X_{35}$ is E, and $X_{37}$ is P.

In an embodiment, the amylin receptor agonist is according to Formula I, wherein $X_{27}X_{28}X_{29}$ is selected from LPP or PSS.

In an embodiment, the amylin receptor agonist is according to Formula I with the proviso that at least two of the amino acids at positions 21, 31 and 35 are an aspartic acid (Asp, D) or a glutamic acid (Glu, E).

In an embodiment, the amino acid at position 2 is a glycine (Gly, G) or a serine (Ser, S).

In an embodiment, the amino acid at position 3 is a glutamic acid (Glu, E), a glutamine (Gln, Q), or a histidine (His, H).

In an embodiment, the amino acid at position 5 is serine (Ser, S).

In an embodiment, the amino acid at position 7 is alanine (Ala, A).

In an embodiment, the amino acid at position 10 is alanine (Ala, A).

In an embodiment, the amino acid at position 19 is a serine (Ser, S) or absent.

In an embodiment, the amino acid at position 20 is a serine (Ser, S) or absent.

In an embodiment, the amino acid at position 21 is an aspartic acid (Asp, D) or absent.

In an embodiment, the amino acid at position 22 is an asparagine (Asn, N), a proline (Pro, P) or absent.

In an embodiment, the amino acid at position 25 is a proline (Pro, P) or a alanine (Ala, A).

In an embodiment, the amino acid at position 27 is a proline (Pro, P) or a leucine (Leu, L).

In an embodiment, the amino acid at position 28 is a proline (Pro, P) or a serine (Ser, S).

In an embodiment, the amino acid at position 29 is a proline (Pro, P) or a serine (Ser, S).

In an embodiment, the amino acid at position 31 is aspartic acid (Asp, D).

In an embodiment, the amino acid at position 34 is a serine (Ser, S) or a proline (Pro, P).

In an embodiment, the amino acid at position 35 is an aspartic acid (Asp, D), an asparagine (Asn, N) or a glutamic acid (Glu, E).

In an embodiment, the amino acid at position 37 is proline (Pro, P).

In an aspect is provided an amylin receptor agonist comprising a peptide selected from the group consisting of SEQ ID NOs: 2-33. In a particular embodiment, the amylin receptor agonist comprising a peptide selected from any one of the following:

```
                                    (SEQ ID NO: 13)
AGELSTAQTARLAEFLHHFGPILPPTDVGSETP, (SEQ ID NO: 16)
ASQLSTAQTARLAEFLHHSSDNFGPILPPTDVGSNTP, (SEQ ID NO: 19)
ASHLSTAQTARLAEFLHHSSDPFGAIPSSTDVGPDTP.
```

In a preferred embodiment, the amylin receptor agonist disclosed herein comprises a C-terminal amide, which is considered essential for bioactivity. In one embodiment, wherein the amylin receptor agonist is considered a human amylin analogue it follows that the proline substituted for tyrosine at the C-terminal comprises an amide group. In a preferred embodiment, the amine group of the C-terminal amide is $NH_2$.

In an embodiment, the amylin receptor agonist does not comprise an intact ring structure. The term "ring structure" means as any functional group that links two or more amino acid residues to each other, such as a disulfide bridge. In an embodiment, the amylin receptor agonist does not comprise a disulfide bridge. The term "disulfide bridge" in reference to human amylin and analogues thereof, refers to a functional group with the structure R-S-S-R' and may also be referred to as a "S S-bond".

In an embodiment, the amylin receptor agonist does not comprise a cysteine residue.

Protraction Moiety

In a preferred embodiment, the amylin receptor agonist comprises a protraction moiety, which may also be referred to as a substituent.

The term "protraction moiety" as used herein refers to a moiety having half-life extending properties and a protraction moiety may be represented by the general formula "A-B" or (A)-(B), in which (A) is an optional linker and (B) is a protractor. The term "protractor" as used herein refers to a molecule which is capable of increasing the half-life of the peptide to which it is attached. The term "protraction" thus refers to half-life extension and a protractor or protraction moiety serves the purpose of the extending the half-life of the amylin receptor agonists as disclosed herein.

The term "protraction moiety" or "substituent", as used herein, refers to a moiety that is covalently attached to a peptide. If a substituent is attached to a peptide, the peptide is referred to as "substituted". When a substituent is covalently attached to a peptide or to an amino acid residue, the peptide or amino acid is said to "carry" a substituent. The substituent may comprise a series of individually defined moieties; these moieties together may be referred to as "substituent elements".

The protraction moiety or substituent may be capable of forming a non-covalent conjugate with albumin, thereby promoting the circulation of the compound in the blood stream, and thus having the effect of protracting the time of which the compound is present in the blood stream, since the aggregate of the fusion compound and albumin is only slowly disintegrated to release the free form of the compound. Thus, the substituent or the protraction moiety, as a whole, may also be referred to as an "albumin-binding moiety", and the substituent or the protraction moiety may be said to have a "protracting effect". The substituent may comprise a portion which is particularly relevant for the albumin binding and thereby the protraction, which portion may be referred to as a "protractor" or a "protracting moiety". Accordingly, the term "substituent" may also be referred to as a "side-chain" or a "protraction moiety".

The protracting moiety may comprise a portion between the protractor (B) and the point of attachment to the polypeptide, which portion may be referred to as a "linker" (A) or "side-chain linker" (A). The linker (A) may comprise several "linker elements". The linker elements may be selected so that they improve the overall properties of the molecule, e.g. so that they improve the oral bioavailability, the conversion half-life or the protracting effect, thus improving the overall exposure profile upon oral administration of the compound.

In particular embodiments, the protractor (B) has at least 10 carbon atoms, or at least 15, 20, 25, 30, 35, or at least 40 carbon atoms. In further particular embodiments, the protractor may further include at least 5 hetero atoms, in particular O and N, for example at least 7, 9, 10, 12, 15, 17, or at least 20 hetero atoms, such as at least 1, 2, or 3 N-atoms, and/or at least 3, 6, 9, 12, or 15 O-atoms.

In particular embodiments, the albumin binding moiety and/or the protracting moiety is lipophilic, and/or negatively charged at physiological pH (7.4).

The albumin binding moiety, the protracting moiety, the protractor or the linker may be covalently attached to the alanine (Ala, A) residue at position 1 or a lysine (Lys, K) residue at position 25 of the peptide by acylation, i.e., via an amide bond formed between a carboxylic acid group thereof (of the albumin binding moiety, the protracting moiety, the protractor or the linker) and an amino group of said alanine (in alpha-position) or lysine (in epsilon-position), respectively. Additional or alternative conjugation chemistry includes alkylation, ester formation, or amide formation, or coupling to a cysteine residue, such as by maleimide or haloacetamide (such as bromo-/fluoro-/iodo-) coupling.

Unless otherwise stated, when reference is made to an acylation of a lysine residue, it is understood to be to the epsilon-amino group thereof. Unless otherwise stated, when reference is made to an acylation of the alanine residue at position 1, it is understood to be to the alpha-amino group thereof.

The term "fatty acid" refers to aliphatic mono- or dicarboxylic acids having from 4 to 28 carbon atoms, it is preferably un-branched, and it may be saturated or unsaturated.

As described above, a protraction moiety may be represented by the general formula "A-B" or (A)-(B), in which (A) is an optional "linker" or "side-chain linker" and (B) is a protractor. Each protraction moiety attaches to the alanine residue at position 1 or a lysine residue in the peptide backbone of the amylin receptor agonist, such as a lysine residue in position 25. When the linker (A) is present, the protraction moiety attaches to the polypeptide backbone via linker (A). When the linker (A) is absent, (B) attaches to the polypeptide backbone.

In an embodiment, a protraction moiety represented by the formula (A)-(B) is covalently attached, via linker (A), to the alpha position of the alanine (Ala, A) at position 1 or to the epsilon position of a lysine (Lys, K) at position 25, via an amide bond formed between a carboxylic acid group of the protraction moiety and an amino group of said alanine (in alpha-position) or lysine (in epsilon-position), respectively. In a particular embodiment, the protraction moiety is covalently attached to the alpha position (i.e. amino group) of the alanine (Ala, A) at position 1. In another particular embodiment, the protraction moiety is covalently attached to the epsilon position (i.e. amino group) of lysine (Lys, K) at position 25. In a further embodiment, the amino acid at position 25 is alanine (Ala, A) or Proline (Pro, P) when the protraction moiety is attached to the alanine (Ala, A) at position 1.

The side-chain linker (A) may comprise Ado, Aeep or Aeeep, sulfonamide, Trx, ε-Lys, Ahx, Glu, γGlu, Gly, Ser, Ala, Thr, and/or a bond.

The optional side-chain linker (A) may comprise at least a moiety which may be represented by the following chemical formula:

Chem. 1a:

Chem. 1b:

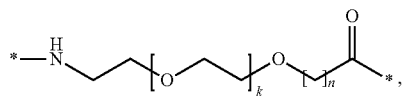

wherein k is an integer in the range of 1-5, and n is an integer in the range of 1-5. When k=1 and n=1, the linker element may be designated Ado, or a 8-amino-3,6-dioxaoctanoyl, which may be represented by the following chemical formula:

Chem. 2a

\*—NH—$(CH_2)_2$—O—$(CH_2)_2$—O—$CH_2$—CO—\*. or

Chem. 2b

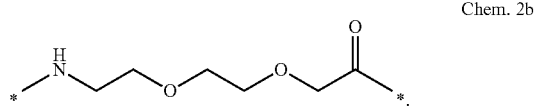

When k=1 and n=2, the linker element may be designated Aeep, which may be represented by the following chemical formula:

Chem. 3a:

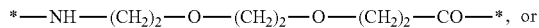

Chem. 3b:

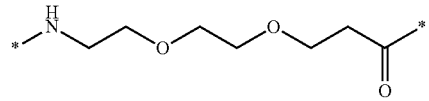

When k=2 and n=2, the linker element may be designated Aeeep, which may be represented by the following chemical formula:

Chem. 4a:

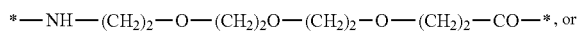
*—NH—(CH₂)₂—O—(CH₂)₂O—(CH₂)₂—O—(CH₂)₂—CO—*, or

Chem. 4b:

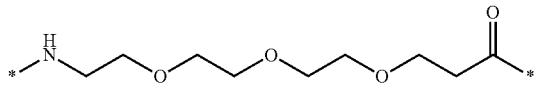

The optional side-chain linker (A) may comprise a sulfonamide-C4 moiety. A sulfonamide-C4 group is a sulfonamide group attached to a 4-butanoyl group and having the following chemical formula:

Chem. 5a:

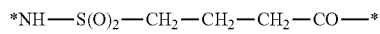
*NH—S(O)₂—CH₂—CH₂—CH₂—CO—*

Chem. 5b:

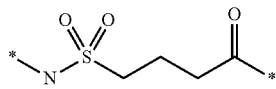

The optional side-chain linker (A) may comprise Trx. Trx is also referred to as Tranexamic acid, trans-4-(aminomethyl)cyclohexanecarboxylic acid and has the following chemical formula:

Chem. 6a

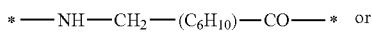
*—NH—CH₂—(C₆H₁₀)—CO—* or

Chem. 6b

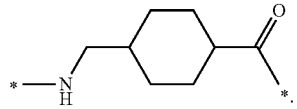

The optional side-chain linker (A) may comprise epsilon-lysine (ε-Lys).

The optional side-chain linker (A) may comprise lysine (Lys).

The optional side-chain linker (A) may comprise Ahx. Ahx is also referred to as Aminocaproic acid, 6-aminohexanoic acid and is defined by Chem. 7a:

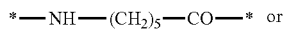
*—NH—(CH₂)₅—CO—* or

Chem. 7b:

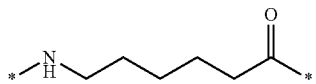

In an embodiment, the side-chain linker (A) comprises a Glu di-radical, such as

Chem. 8a:

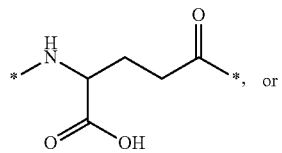
, or

Chem. 8b:

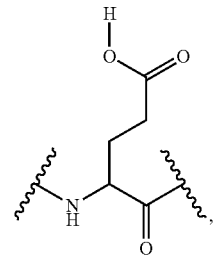
, wherein the Glu di-radical may be included p times, where p is an integer in the range of 1-3. Chem. 8a may also be referred to as gamma-Glu, or briefly gGlu, due to the fact that it is the gamma carboxy group of the amino acid glutamic acid which is here used for connection to another linker element, or to the epsilon-amino group of lysine, or to the alpha group of the alanine in position 1. The amino group of Glu in turn forms an amide bond with the carboxy group of the fatty di-acid, or with the gamma-carboxy group of, e.g., another Glu, if present. Chem. 8b may also be referred to as a Glu.

In an embodiment, the linker (A) of the protraction moiety comprises a moiety according to Chem. 8a. In some embodiments, the linker (A) of the protraction moiety comprises one or two moieties according to Chem. 8a. In a particular embodiment, the linker (A) of the protraction moiety consists of one moiety according to Chem. 8a. In another particular embodiment, the linker (A) of the protraction moiety consists of two moieties according to Chem. 8a.

In an embodiment, the linker (A) of the protraction moiety comprises a moiety according to Chem. 8b. In some embodiments, the linker (A) of the protraction moiety comprises one or two moieties according to Chem. 8b. In a particular embodiment, the linker (A) of the protraction moiety consists of one moiety according to Chem. 8b. In another particular embodiment, the linker (A) of the protraction moiety consists of two moieties according to Chem. 8b. In an embodiment, Glu is of the L-form.

The protractor (B) may comprise an acyl group. The acyl group may be branched or unbranched. The acyl group may be saturated or unsaturated. The protractor (B) may comprise a fatty acyl group. The acyl group may be branched or unbranched. The acyl group may be saturated or unsaturated.

In an embodiment, the protractor (B) comprises a distal carboxylic acid group.

In an embodiment, the protractor (B) comprises a fatty acid group.

In an embodiment, the protractor (B) comprises a fatty acid group and an amide group.

In an embodiment, the protractor (B) comprises a distal carboxylic acid group and an amide group.

In an embodiment, the protractor (B) comprises an alkyl group.

In an embodiment, the protractor (B) comprises an aryl group.

In an embodiment, the protractor (B) comprises a tetrazole group.

In an embodiment, the protractor (B) comprises a sulfonic acid group.

In an embodiment, the protractor (B) comprises a phenoxy group.

In an embodiment, the protractor (B) comprises a benzoic acid group.

In an embodiment, the protractor (B) comprises a group defined by Chem. 9: HOOC—$(CH_2)_n$—CO—* wherein n is an integer in the range of 8-30, which may also be referred to as a C(n+2) diacid or as Chem. 10:

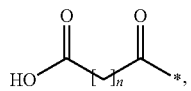

wherein n is an integer in the range of 8-30.

In an embodiment, the protractor (B) of the protraction moiety comprises a C14 diacid, a C16 diacid, a C18 diacid, a C20 diacid, a C18-tetrazole, a C14-sulfonic acid, 4-(9-carboxynonyloxy) benzoic acid, 4-(10-carboxydecyloxy) benzoic acid, or 3-(9-carboxynonyloxy) benzoic acid. In a particular embodiment, the protractor (B) of the protraction moiety comprises a C14 diacid, C16 diacid, C18 diacid, or C20 diacid. Specifically, in an embodiment, the protractor (B) of the protraction moiety consists of a C18 diacid. Specifically in another embodiment, the protractor (B) of the protraction moiety consists of a C20 diacid.

In an embodiment where the protraction moiety is attached to the epsilon position of lysine (Lys, K) at position 25, the peptide comprises an N-terminal substituent. In a further embodiment, the substituent is covalently attached to the alpha-amino group of the amino acid residue in the N-terminus, i.e. alanine (Ala, A) at position 1. In a further embodiment, the N-terminal substituent is an alkanoyl or acyl group. In a further particular embodiment, the N-terminal substituent is an acetyl group. As an example of an N-terminal substituted amino acid is Ac-Ala at position 1.

The compounds disclosed herein have a long half-life compared to their native ligands. The in vivo half-life of the amylin receptor agonist may be assessed as described in Example 5. The compound disclosed herein may possess a long biological half-life, relative to dosing interval, thus reducing the variability in steady state exposure. The half-life of the amylin receptor agonist in animal subjects may be as long as about 150 hours, or longer. In an embodiment, the half-life of the amylin receptor agonist in animal subjects is at least 4 hours. In an embodiment, the half-life of the amylin receptor agonist is more than 5, 10, 15, 20, 25, 30, 35, 40, 45, 50, 55, 60, 65, 70, 75, 80, 85, or 90 hours. In an embodiment, the half-life of the amylin receptor agonist is 15-160 hours, such as 50-155 hours.

In a particular embodiment, the amylin receptor agonist has a half-life [h] of at least 80 in Beagle dogs following oral administration, measured according to the assay of Example 5. More specifically, in an embodiment, the amylin receptor agonist has a half-life [h] of 80-150 in Beagle dogs following oral administration, measured according to the assay of Example 5.

Pharmaceutically Acceptable Salt, Amide, or Ester

The derivatives, analogues, and intermediate products of the invention may be in the form of a pharmaceutically acceptable salt, amide, or ester. An aspect of the present invention relates to a pharmaceutically acceptable salt of the amylin receptor agonist as disclosed herein. Another aspect of the present invention relates to a pharmaceutically acceptable ester of the amylin receptor agonist as disclosed herein. Yet another aspect of the present invention relates to a pharmaceutically acceptable amide of the amylin receptor agonist as disclosed herein.

Salts are e.g. formed by a chemical reaction between a base and an acid, e.g.: $2NH_3+H_2SO_4 \rightarrow (NH_4)_2SO_4$.

The salt may be a basic salt, an acid salt, or it may be neither nor (i.e. a neutral salt). Basic salts produce hydroxide ions and acid salts hydronium ions in water.

The salts of the derivatives of the invention may be formed with added cations or anions between anionic or cationic groups, respectively. These groups may be situated in the peptide moiety, and/or in the side chain of the derivatives of the invention.

Non-limiting examples of anionic groups of the derivatives of the invention include free carboxylic groups in the side chain, if any, as well as in the peptide moiety. The peptide moiety often includes a free carboxylic acid group at the C-terminus, and it may also include free carboxylic groups at internal acid amino acid residues such as Asp and Glu.

Non-limiting examples of cationic groups in the peptide moiety include the free amino group at the N-terminus, if present, as well as any free amino group of internal basic amino acid residues such as His, Arg, and Lys.

The ester of the derivatives of the invention may, e.g., be formed by the reaction of a free carboxylic acid group with an alcohol or a phenol, which leads to replacement of at least one hydroxyl group by an alkoxy or aryloxy group The ester formation may involve the free carboxylic group at the C-terminus of the peptide, and/or any free carboxylic group in the side chain.

The amide of the derivatives of the invention may, e.g., be formed by the reaction of a free carboxylic acid group with an amine or a substituted amine, or by reaction of a free or substituted amino group with a carboxylic acid.

The amide formation may involve the free carboxylic group at the C-terminus of the peptide, any free carboxylic group in the side chain, the free amino group at the N-terminus of the peptide, and/or any free or substituted amino group of the peptide in the peptide and/or the side chain.

In a particular embodiment, the peptide or derivative is in the form of a pharmaceutically acceptable salt. In another particular embodiment, the derivative is in the form of a pharmaceutically acceptable amide, preferably with an amide group at the C-terminus of the peptide. In a still further particular embodiment, the peptide or derivative is in the form a pharmaceutically acceptable ester.

Compounds

In an embodiment according to the present invention the amylin receptor agonist is selected from the group consisting of Compound 2-43.

In a particular embodiment, the amylin receptor agonist is selected from the group consisting of Compound 16, Compound 22, and Compound 25.

In a particular embodiment, the amylin receptor agonist is Compound 16 according to the formula:

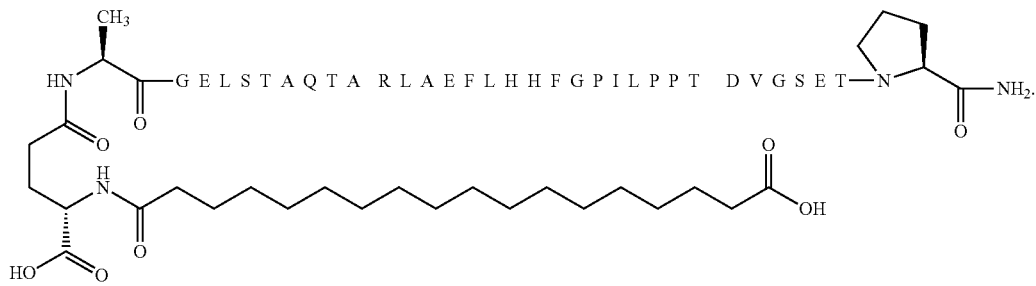

In a particular embodiment, the amylin receptor agonist is Compound 22 according to the formula:

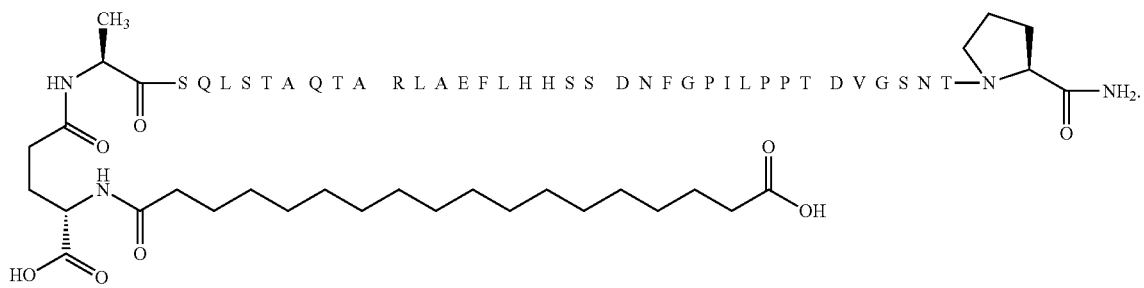

In a particular embodiment, the amylin receptor agonist is Compound 25 according to the formula:

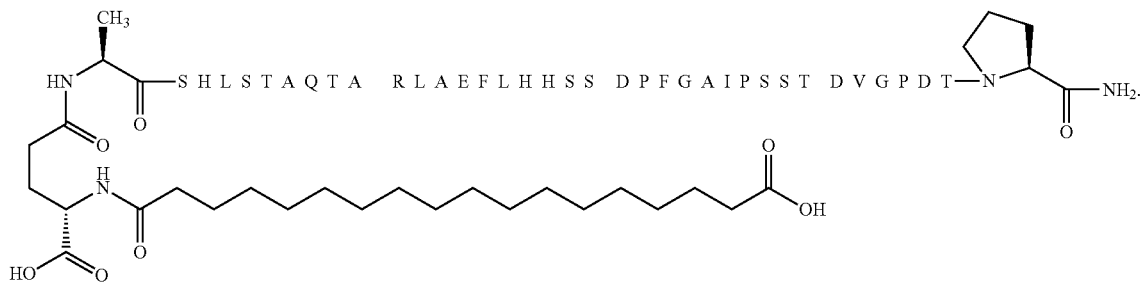

In an embodiment, the amylin receptor agonist disclosed herein reduces food intake in a subject. In an embodiment, administration of the amylin receptor agonist disclosed herein results in an acute reduction in the intake of food. In an embodiment, the amylin receptor agonist reduces body weight. The in vivo effect of the amylin receptor agonist on food intake in rats may be assessed as described in Example 6. In an embodiment, administration of the amylin receptor agonist disclosed herein results in a food intake in rats, relative to vehicle, which is 0-90%, such as 0-80%, such as 0-70%, such as 0-60%, preferably 0-50%, even more preferably 0-40%, within 0-24 hours after a single subcutaneous injection of 3 nmol/kg or 10 nmol/kg of said co-agonist, wherein a food intake of 0% relative to vehicle means that the rat does not eat. In an embodiment, administration of the amylin receptor agonist disclosed herein results in a food intake in rats, relative to vehicle, which is 0-90%, such as 0-80%, such as 0-70%, such as 0-60%, preferably 0-50%, even more preferably 0-40%, within 24-48 hours after a single subcutaneous injection of 3 nmol/kg or 10 nmol/kg of said co-agonist, wherein a food intake of 0% relative to vehicle means that the rat does not eat.

In an embodiment, the amylin receptor agonist shows food intake reduction in rats tested according to the assay of Example 6 after administration of 3 nmol/kg. In an embodiment, the amylin receptor agonist shows reduction in food intake in rats tested according to the assay of Example 6 of which can be seen within 0-24 hours after administration of 3 nmol/kg. In an embodiment, the amylin receptor agonist shows reduction in food intake in rats tested according to the assay of Example 6 which can be seen within 0-24 and/or 24-48 hours after administration of 3 nmol/kg. In an embodiment, the amylin receptor agonist shows reduction in food intake by at least 10%, such as at least 15%, 20%, 30%, 40%, 50%, 60%, or 70%, in rats tested according to the assay of Example 6 which can be seen within 0-24 hours after administration of 3 nmol/kg. In an embodiment, the amylin receptor agonist shows reduction in food intake by at least 10% such as at least 15%, 20%, 30%, 40%, 50%, or 60%, in rats tested according to the assay of Example 6 which can be seen within 24-48 hours after administration of 3 nmol/kg. In an embodiment, the amylin receptor agonist shows reduction in food intake by at least 10% such as at least 15%, 20%, 30%, 40%, 50%, or 60%, in rats tested according to the assay of Example 6 which can be seen within 48-72 hours after administration of 3 nmol/kg.

Oral Bioavailability

Oral treatment with pharmacological active compounds may be hampered by poor bioavailability. The term "bioavailability" refers to the capability of a compound to reach systemic circulation following administration, and it may be quantified as the fractional extent of the compound dosage that reaches systemic circulation upon administration. It is desirable that a drug intended for oral administration has a high oral absorption (i.e. a high absorption form the gastrointestinal tract following oral administration) since it may reduce the dosage required to reach the intended systemic concentration of the drug, and thus e.g. reduce tablet size and manufacturing costs.

The term "oral bioavailability" as used herein refers to the capability of a compound to reach systemic circulation following oral administration. The oral bioavailability reflects the extent to which a compound is absorbed in the gastrointestinal tract following oral administration. In other words a high oral bioavailability is associated with a high oral absorption. A high oral bioavailability of a drug is associated with a high drug exposure following oral administration. The oral bioavailability may be measured in a formulation with the absorption enhancer sodium N-(8-[2-hydroxybenzoyl] amino) caprylate (SNAC) in beagle dogs as described in WO 2019/149880.

The oral bioavailability may be measured as described in Example 5. In one embodiment, the compound of the invention has a high oral bioavailability. In one embodiment, the compound of the invention has an oral bioavailability that is similar to that of semaglutide. In one embodiment, the compound of the invention has an oral bioavailability that is not inferior to that of semaglutide. In one embodiment, the compound of the invention has an oral bioavailability that is as least as high as that of semaglutide. In one embodiment, the compound of the invention has an oral bioavailability which is suitable for oral dosing in humans. In one embodiment, the compound of the invention has an oral bioavailability which is determined in Beagle dogs and measured as Cmax/Dose [kg/L]. Specifically, in an embodiment the oral bioavailability is determined in Beagle dogs, measured according to the assay of Example 5. In a particular embodiment, the oral exposure level is determined in Beagle dogs upon administration of tablets containing 3 mg of the compound, 300 mg sodium N-(8-(2-hydroxybenzoyl) amino)caprylate (SNAC) and 7.7 mg magnesium stearate.

In one embodiment, the compound of the invention has an oral bioavailability which is measured as Cmax/Dose [kg/L] in Beagle dogs; wherein the Cmax/Dose [kg/L] is at least 0.1, preferably at least 0.15, and most preferably at least 0.20. In an embodiment, the oral bioavailability is measured as Cmax/Dose [kg/L] in Beagle dogs; and wherein the Cmax/Dose [kg/L] is 0.1-0.5.

In one embodiment, the compound of the invention has an oral bioavailability which is determined in Beagle dogs and measured as AUC/Dose [kg*hr/L]. In one embodiment, the compound of the invention has an oral bioavailability which is determined in Beagle dogs and measured as AUC/Dose [kg*hr/L]; wherein the AUC/Dose [kg*hr/L] is at least 2, preferably at least 5, and most preferably at least 10. In an embodiment, the oral bioavailability is measured as AUC/Dose [kg*hr/L] in Beagle dogs; and wherein the AUC/Dose [kg*hr/L] is 10-40.

Pharmaceutical Compositions

Also disclosed herein is a pharmaceutical composition comprising the amylin analogues disclosed herein. Pharmaceutical compositions comprising the amylin analogues, or a pharmaceutically acceptable salt thereof, and one or more pharmaceutically acceptable excipients, may be prepared using methods known to the person skilled in the art.

The term "pharmaceutically acceptable excipient" refers to any ingredient in the pharmaceutical composition which is not the active pharmaceutical ingredient. The excipient may be functional or inert and may serve one or more purposes. For example, the excipient may enhance absorption of the active substance. The excipient might be, amongst others, a buffer, an antimicrobial preservative, an isotonicity agent, a carrier, a vehicle, a filler, a binder, a lubricant, a glidant, a disintegrant, a flow control agent, a crystallization inhibitor, a solubilizer, a stabilizer, a coloring agent, a flavoring agent, a surfactant, an emulsifier. The amount of each excipient used may vary within ranges conventional in the art.

The pharmaceutical composition may be suitable for oral administration. Techniques and excipients which may be used to formulate orally administered pharmaceutical compositions are described in *Handbook of Pharmaceutical Excipients* (e.g. $8^{th}$ edition, Sheskey et al., Eds., American Pharmaceuticals Association and Pharmaceutical Press, publications department of the Royal Pharmaceutical Society of Great Britain (2017) and later editions); and *Remington: The Science and Practice of Pharmacy* (e.g. 22nd edition, Remington and Allen, Eds., Pharmaceutical Press (2013), and later editions).

The pharmaceutical composition may be a solid pharmaceutical composition (e.g. a compressed tablet or capsule) containing the active pharmaceutical ingredient, for example as a freeze-dried or spray-dried composition, and may be used as is, dissolved prior to use, or combined with excipients in the composition.

The pharmaceutical composition comprising the compound of the invention is suitable for oral administration. In an embodiment for oral administration, the pharmaceutical composition comprising the compound of the invention is prepared in the form of a tablet where the compound is formulated with the absorption enhancer sodium N-(8-[2-hydroxybenzoyl] amino) caprylate (SNAC), e.g. as described in WO 2019/149880 or WO 2019/215063. Optionally, the compound is further formulated with a lubricant magnesium stearate.

Alternatively, the pharmaceutical composition may be a liquid formulation, such as an aqueous formulation. Such liquid composition may be suitable for oral administration or for parenteral administration. Liquid compositions that are suitable for injection can be prepared using conventional techniques of the pharmaceutical industry which involve dissolving and mixing the ingredients as appropriate to give the desired end product. Thus, according to one procedure, the compound described herein is dissolved in a suitable buffer at a suitable pH. The composition may be sterilized, for example, by sterile filtration. Techniques and excipients which may be used to prepare liquid formulations are described in *Handbook of Pharmaceutical Excipients* (e.g. $8^{th}$ edition, Sheskey et al., Eds., American Pharmaceuticals Association and Pharmaceutical Press, publications department of the Royal Pharmaceutical Society of Great Britain (2017) and later editions); and *Remington: The Science and Practice of Pharmacy* (e.g. $22^{nd}$ edition, Remington and Allen, Eds., Pharmaceutical Press (2013), and later editions).

In aspect of the present invention is provided a pharmaceutical composition comprising the amylin receptor agonist and/or pharmaceutically acceptable salt, ester, or amide thereof, as disclosed herein.

In a particular embodiment, the pharmaceutical composition is for oral administration. Accordingly, in an embodiment the pharmaceutical composition is a solid pharmaceutical composition. More specifically, in an embodiment the pharmaceutical composition is a tablet.

In a particular embodiment, the pharmaceutical composition is for s.c. administration. Accordingly, in an embodiment the pharmaceutical composition is a liquid formulation, such as an aqueous formulation. Such liquid composition may be suitable for oral administration or for parenteral administration. Liquid compositions that are suitable for injection can be prepared using conventional techniques of the pharmaceutical industry which involve dissolving and mixing the ingredients as appropriate to give the desired end product. Thus, according to one procedure, the compound described herein is dissolved in a suitable buffer at a suitable pH. The composition may be sterilized, for example, by sterile filtration. Techniques and excipients which may be used to prepare liquid formulations are described in *Handbook of Pharmaceutical Excipients* (e.g. $8^{th}$ edition, Sheskey et al., Eds., American Pharmaceuticals Association and Pharmaceutical Press, publications department of the Royal Pharmaceutical Society of Great Britain (2017) and later editions); and *Remington: The Science and Practice of Pharmacy* (e.g. $22^{nd}$ edition, Remington and Allen, Eds., Pharmaceutical Press (2013), and later editions). Preferably, in an embodiment wherein pharmaceutical composition is in a liquid formulation, the liquid formulation provides an improved stability.

Pharmaceutical Indications

The amylin receptor agonist may exhibit a variety of properties rendering it useful as a medicament, as described herein. Accordingly, in an embodiment, the amylin analogue or pharmaceutical composition thereof as disclosed herein for use as a medicament. The amylin analogue disclosed herein may be used for the following medical treatments:

(i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1c;

(ii) delaying or preventing diabetic disease progression, such as progression in type 2 diabetes, delaying the progression of impaired glucose tolerance (IGT) to insulin requiring type 2 diabetes, and/or delaying the progression of non-insulin requiring type 2 diabetes to insulin requiring type 2 diabetes;

(iii) prevention and/or treatment of eating disorders, such as obesity, e.g. by decreasing food intake, reducing body weight, suppressing appetite, inducing satiety; treating or preventing binge eating disorder, food cravings, bulimia nervosa and/or obesity induced by administration of an antipsychotic or a steroid; reduction of gastric motility; and/or delaying gastric emptying;

(iv) weight maintenance after successful weight loss (either drug induced or by diet and exercise)—i.e. prevention of weight gain after successful weight loss;

(v) prevention and/or treatment of cardiovascular diseases, such as delaying or reducing development of a major adverse cardiovascular event (MACE) selected from the group consisting of cardiovascular death, non-fatal myocardial infarction, non-fatal stroke, revascularization, hospitalization for unstable angina pectoris, and hospitalization for heart failure.

(vi) prevention and/or treatment of non-alcoholic steatohepatitis (NASH);

(vii) prevention and/or treatment of cognitive impairment, such as that caused by Alzheimer's disease.

In some embodiments the indication is (i). In some embodiments the indication is (ii). In a still further particular aspect the indication is (iii). In some embodiments the indication is (iv). In some embodiments the indication is (v). In some embodiments the indication is (vi). In some embodiments the indication is (vii). In some embodiments the indication is type 2 diabetes and/or obesity.

The term "treatment", as used herein, refers to the medical therapy of any human or other vertebrate subject in need thereof. Said subject is expected to have undergone physical examination by a medical practitioner, or a veterinary medical practitioner, who has given a tentative or definitive diagnosis which would indicate that the use of said specific treatment is beneficial to the health of said human or other vertebrate. The timing and purpose of said treatment may vary from one individual to another, according to the status quo of the subject's health. Thus, said treatment may be prophylactic (preventative), palliative, symptomatic and/or curative.

In some embodiments the indication is (i) and (iii). In some embodiments the indication is (ii) and (iii).

In some embodiments the subject suffering from obesity is human, such as an adult human or a paediatric human (including infants, children, and adolescents).

Body mass index (BMI) is a measure of body fat based on height and weight. The formula for calculation is BMI=weight in kilograms/height in meters$^2$. A human subject suffering from obesity may have a BMI of $\geq 30$; this subject may also be referred to as being obese. In some embodiments the human subject suffering from obesity may have a BMI of $\geq 35$ or a BMI in the range of $\geq 30$ to $<40$. In some embodiments the obesity is severe obesity or morbid obesity, wherein the human subject may have a BMI of $\geq 40$.

In some embodiments the invention relates to a method for treatment or prevention of overweight, optionally in the presence of at least one weight-related comorbidity. In some embodiments the invention relates to use of the pharmaceutical composition for treatment or prevention of overweight, optionally in the presence of at least one weight-related comorbidity. In some embodiments the subject suffering from overweight is human, such as an adult human or a paediatric human (including infants, children, and adolescents). In some embodiments a human subject suffering from overweight may have a BMI of $\geq 25$, such as a BMI of $\geq 27$, such as a BMI of $\geq 30$, such as a BMI of $\geq 35$ or a BMI of $\geq 40$. In some embodiments a human subject suffering from overweight has a BMI in the range of 25 to $<30$ or in the range of 27 to $<30$. In some embodiments the weight-related comorbidity is selected from the group consisting of hypertension, diabetes (such as type 2 diabetes), dyslipidaemia, high cholesterol and obstructive sleep apnoea.

The term "reduction of body weight" may include treatment or prevention of obesity and/or overweight.

In an embodiment, administration of the compound disclosed herein is as an adjunct to a reduced-calorie diet and increased physical activity for chronic weight management in adult or paediatric patients with an initial body mass index (BMI) of 30 kg/m$^2$ or greater (obesity) or 27 kg/m$^2$ or greater (overweight) in the presence of at least one weight-related comorbidity (e.g. hypertension, type 2 diabetes mellitus, or dyslipidemia).

In an embodiment, the co-morbidity is diabetes and/or a cardiovascular disease.

In an embodiment, the amylin receptor agonist is for use in the treatment of subjects with diabetes, such as type II diabetes. In an embodiment, the amylin receptor agonist is for use in the treatment and/or prevention of cardiovascular disease. In an embodiment, the amylin receptor agonist is for use in the treatment of non-alcoholic steatohepatitis (NASH). In an embodiment, the amylin receptor agonist is for use in the treatment and/or prevention of cognitive impairment, such as that caused by Alzheimer's disease.

Fixed-Dose Combination

An aspect of the present invention relates to pharmaceutical co-formulation or co-treatment comprising an amylin receptor agonist as disclosed herein, and further comprising one or more GLP-1 receptor agonist(s). In an embodiment, the one or more GLP-1 receptor agonist(s) is a peptide GLP-1 receptor agonist or a small molecule GLP-1 receptor agonist. In an embodiment, the at least one of the one or more GLP-1 receptor agonist(s) is for the treatment and/or prevention of diabetes, a cardiovascular disease, NASH, and/or Alzheimer's disease. In an embodiment, pharmaceutical co-formulation or co-treatment comprises one or more GLP-1-GIP receptor co-agonist(s), wherein the GLP-1-GIP receptor co-agonist(s) is a peptide GLP-1-GIP receptor co-agonist or a small molecule GLP-1-GIP receptor co-agonist.

An aspect of the present invention relates to pharmaceutical co-formulation or co-treatment comprising an amylin receptor agonist as disclosed herein, and further comprising one or more peptide(s). In an embodiment, at least one of the one or more peptide(s) is for the treatment and/or prevention of diabetes, a cardiovascular disease, NASH, and/or Alzheimer's disease. In a particular embodiment, at least one of the one or more peptide(s) is a GLP-1 peptide. More specifically, in an embodiment the GLP-1 peptide is a GLP-1 compound, GLP-1 analogue, or GLP-1 derivative. Even more specifically, in an embodiment the GLP-1 compound, GLP-1 analogue, or GLP-1 derivative is semaglutide or liraglutide.

In an embodiment, at least one of the one or more peptide(s) is a GLP-1-GIP receptor co-agonist.

In an embodiment, at least one of the one or more peptide(s) is an insulin peptide. More specifically, in an embodiment the insulin peptide is an insulin compound, insulin analogue, or insulin derivative.

Dosing Frequency

In an embodiment, the amylin analogues are formulated for oral administration, such as in a tablet. In such an embodiment, the amylin analogues disclosed herein may be administered approximately once daily, such as once every 12-36 hours, such as once every 18-30 hours, such as approximately once every 24 hours. The amylin analogues disclosed herein may be administered approximately once every other day, such as once every 36-60 hours, such as once every 42-54 hours, such as approximately once every 48 hours. The amylin analogues disclosed herein may be administered approximately twice daily, such as once every 6-18 hours, such as once every 9-15 hours, such as approximately once every 12 hours.

In an embodiment, the amylin analogues are formulated for s.c. administration, such as in a liquid formulation. In such an embodiment, the amylin analogues disclosed herein may be administered approximately once daily, such as once every 12-36 hours, such as once every 18-30 hours, such as approximately once every 24 hours. In an embodiment, the amylin analogues in a liquid formulation may be administered once weekly, once every second week, or once monthly.

Methods of Production

The compounds disclosed herein may, for instance, be produced by classical peptide synthesis, e.g. solid phase peptide synthesis using t-Boc or Fmoc chemistry, or other well established techniques, see e.g. Greene and Wuts, "Protective Groups in Organic Synthesis", John Wiley & Sons, 1999; Florencio Zaragoza Dörwald, "Organic Synthesis on Solid Phase", Wiley-VCH Verlag GmbH, 2000; and "Fmoc Solid Phase Peptide Synthesis", Edited by W. C. Chan and P. D. White, Oxford University Press, 2000.

Alternatively, the compounds may be produced by recombinant methods, e.g. by culturing a host cell containing a DNA sequence encoding the peptide sequence and capable of expressing the peptide, in a suitable nutrient medium under conditions permitting the expression of the peptide. Non-limiting examples of host cells suitable for expression of these peptides are *Escherichia coli, Saccharomyces cerevisiae* and mammalian BHK or CHO. Specific examples of methods of preparing the disclosed compounds are included in the examples.

A further aspect of the invention relates to a method for preparing the peptides described herein. In an embodiment, the method for preparing a compound as described herein comprises a step of solid phase peptide synthesis. The substituent or protraction moiety may be built sequentially as part of the solid phase peptide synthesis or produced separately and attached via the alanine or lysine residue after peptide synthesis.

PARTICULAR EMBODIMENTS

The aspects of the present invention are now further described by the following non-limiting embodiments:

1. An amylin receptor agonist comprising a peptide according to Formula I (SEQ ID NO: 36):

$$AX_2X_3LX_5TX_7QTX_{10}RLAEFLHHX_{19}X_{20}X_{21}X_{22}FGX_{25}IX_{27}X_{28}$$

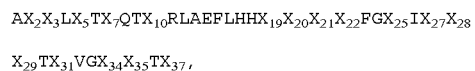

wherein
$X_2$ is S or G
$X_3$ is N, H, S, Q, A or E
$X_5$ is A or S
$X_7$ is A or L
$X_{10}$ is Q or A
$X_{19}$ is S or absent
$X_{20}$ is S, or absent
$X_{21}$ is D, E or absent
$X_{22}$ is N, P or absent
$X_{25}$ is A, K or P
$X_{27}$ is L or P
$X_{28}$ is S or P
$X_{29}$ is S or P
$X_{31}$ is D or E
$X_{34}$ is S or P
$X_{35}$ is N, D or E
$X_{37}$ is Y or P,
wherein the peptide comprises a C-terminal amide.

2. The amylin receptor agonist according to the preceding embodiment, wherein the peptide is an amylin analogue.

3. The amylin receptor agonist according to any one of the preceding embodiments, with the proviso that at least two of the amino acids at positions 21, 31 and 35 are an aspartic acid (Asp, D) or a glutamic acid (Glu, E).

4. The amylin receptor agonist according to any one of the preceding embodiments, comprising a peptide according to Formula I (SEQ ID NO: 36):

$$AX_2X_3LX_5TX_7QTX_{10}RLAEFLHHX_{19}X_{20}X_{21}X_{22}FGX_{25}IX_{27}X_{28}$$
$$X_{29}TX_{31}VGX_{34}X_{35}TX_{37},$$

wherein
$X_2$ is S or G
$X_3$ is H, S, Q or E
$X_5$ is S
$X_7$ is A
$X_{10}$ is Q or A
$X_{19}$ is S or absent
$X_{20}$ is S or absent
$X_{21}$ is D, E or absent
$X_{22}$ is N, P or absent
$X_{25}$ is A or P
$X_{27}$ is L or P
$X_{28}$ is S or P
$X_{29}$ is S or P
$X_{31}$ is D
$X_{34}$ is S or P
$X_{35}$ is N, D or E
$X_{37}$ is P.

5. The amylin receptor agonist according to any one of the preceding embodiments, comprising a peptide according to Formula I (SEQ ID NO: 36):

$$AX_2X_3LX_5TX_7QTX_{10}RLAEFLHHX_{19}X_{20}X_{21}X_{22}FGX_{25}IX_{27}X_{28}$$
$$X_{29}TX_{31}VGX_{34}X_{35}TX_{37},$$

wherein
$X_2$ is S or G
$X_3$ is H, S, Q or E
$X_5$ is S
$X_7$ is A
$X_{10}$ is Q or A
$X_{19}$ is absent
$X_{20}$ is absent
$X_{21}$ is absent
$X_{22}$ is absent
$X_{25}$ is A or P
$X_{27}$ is L or P
$X_{28}$ is S or P
$X_{29}$ is S or P
$X_{31}$ is D
$X_{34}$ is S or P
$X_{35}$ is N, D or E
$X_{37}$ is P.

6. The amylin receptor agonist according to any one of the preceding embodiments, comprising a peptide according to Formula I (SEQ ID NO: 36):

$$AX_2X_3LX_5TX_7QTX_{10}RLAEFLHHX_{19}X_{20}X_{21}X_{22}FGX_{25}IX_{27}X_{28}$$
$$X_{29}TX_{31}VGX_{34}X_{35}TX_{37},$$

wherein
$X_2$ is S or G
$X_3$ is H, S or E
$X_5$ is S
$X_7$ is A
$X_{10}$ is Q or A
$X_{19}$ is absent
$X_{20}$ is absent
$X_{21}$ is absent
$X_{22}$ is absent
$X_{25}$ is P
$X_{27}$ is L
$X_{28}$ is P
$X_{29}$ is P
$X_{31}$ is D
$X_{34}$ is S
$X_{35}$ is E
$X_{37}$ is P.

7. The amylin receptor agonist according to any one of the preceding embodiments, wherein $X_{27}X_{28}X_{29}$ is selected from LPP or PSS.

8. The amylin receptor agonist according to any one of the preceding embodiments, wherein the amino acid at position 2 is a glycine (Gly, G) or a serine (Ser, S).

9. The amylin receptor agonist according to any one of the preceding embodiments, wherein the amino acid at position 3 is a glutamic acid (Glu, E), a glutamine (Gln, Q), or a histidine (His, H).

10. The amylin receptor agonist according to any one of the preceding embodiments, wherein the amino acid at position 5 is serine (Ser, S).

11. The amylin receptor agonist according to any one of the preceding embodiments, wherein the amino acid at position 7 is alanine (Ala, A).

12. The amylin receptor agonist according to any one of the preceding embodiments, wherein the amino acid at position 10 is alanine (Ala, A).

13. The amylin receptor agonist according to any one of the preceding embodiments, wherein the amino acid at position 19 is a serine (Ser, S) or absent.

14. The amylin receptor agonist according to any one of the preceding embodiments, wherein the amino acid at position 20 is a serine (Ser, S) or absent.

15. In an embodiment, the amino acid at position 22 is an asparagine (Asn, N), a proline (Pro, P) or absent.

16. The amylin receptor agonist according to any one of the preceding embodiments, wherein the amino acid at position 25 is a proline (Pro, P) or a alanine (Ala, A).

17. The amylin receptor agonist according to any one of the preceding embodiments, wherein the amino acid at position 27 is a proline (Pro, P) or a leucine (Leu, L).

18. The amylin receptor agonist according to any one of the preceding embodiments, wherein the amino acid at position 28 is a proline (Pro, P) or a serine (Ser, S).

19. The amylin receptor agonist according to any one of the preceding embodiments, wherein the amino acid at position 29 is a proline (Pro, P) or a serine (Ser, S).

20. The amylin receptor agonist according to any one of the preceding embodiments, wherein the amino acid at position 21 is an aspartic acid (Asp, D) or absent.

21. The amylin receptor agonist according to any one of the preceding embodiments, wherein the amino acid at position 31 is aspartic acid (Asp, D).

22. The amylin receptor agonist according to any one of the preceding embodiments, wherein the amino acid at position 34 is a serine (Ser, S) or a proline (Pro, P).

23. The amylin receptor agonist according to any one of the preceding embodiments, wherein the amino acid at position 35 is an aspartic acid (Asp, D), an asparagine (Asn, N) or a glutamic acid (Glu, E).

24. The amylin receptor agonist according to any one of the preceding embodiments, wherein the amino acid at position 37 is proline (Pro, P).

25. An amylin receptor agonist comprising a peptide selected from the group consisting of SEQ ID Nos: 2-33.

26. An amylin receptor agonist comprising a peptide of SEQ ID NO: 2.

27. An amylin receptor agonist comprising a peptide of SEQ ID NO: 3.

28. An amylin receptor agonist comprising a peptide of SEQ ID NO: 4.

29. An amylin receptor agonist comprising a peptide of SEQ ID NO: 5.

30. An amylin receptor agonist comprising a peptide of SEQ ID NO: 6.

31. An amylin receptor agonist comprising a peptide of SEQ ID NO: 7.

32. An amylin receptor agonist comprising a peptide of SEQ ID NO: 8.

33. An amylin receptor agonist comprising a peptide of SEQ ID NO: 9.

34. An amylin receptor agonist comprising a peptide of SEQ ID NO: 10.

35. An amylin receptor agonist comprising a peptide of SEQ ID NO: 11.

36. An amylin receptor agonist comprising a peptide of SEQ ID NO: 12.

37. An amylin receptor agonist comprising a peptide of SEQ ID NO: 13.

38. An amylin receptor agonist comprising a peptide of SEQ ID NO: 14.

39. An amylin receptor agonist comprising a peptide of SEQ ID NO: 15.

40. An amylin receptor agonist comprising a peptide of SEQ ID NO: 16.

41. An amylin receptor agonist comprising a peptide of SEQ ID NO: 17.

42. An amylin receptor agonist comprising a peptide of SEQ ID NO: 18.

43. An amylin receptor agonist comprising a peptide of SEQ ID NO: 19.

44. An amylin receptor agonist comprising a peptide of SEQ ID NO: 20.

45. An amylin receptor agonist comprising a peptide of SEQ ID NO: 21.

46. An amylin receptor agonist comprising a peptide of SEQ ID NO: 22.

47. An amylin receptor agonist comprising a peptide of SEQ ID NO: 23.

48. An amylin receptor agonist comprising a peptide of SEQ ID NO: 24.

49. An amylin receptor agonist comprising a peptide of SEQ ID NO: 25.

50. An amylin receptor agonist comprising a peptide of SEQ ID NO: 26.

51. An amylin receptor agonist comprising a peptide of SEQ ID NO: 27.

52. An amylin receptor agonist comprising a peptide of SEQ ID NO: 28.

53. An amylin receptor agonist comprising a peptide of SEQ ID NO: 29.

54. An amylin receptor agonist comprising a peptide of SEQ ID NO: 30.

55. An amylin receptor agonist comprising a peptide of SEQ ID NO: 31.

56. An amylin receptor agonist comprising a peptide of SEQ ID NO: 32.

57. An amylin receptor agonist comprising a peptide of SEQ ID NO: 33.

58. An amylin receptor agonist comprising a peptide selected from any one of the following:

```
                                         (SEQ ID NO: 13)
AGELSTAQTARLAEFLHHFGPILPPTDVGSETP (SEQ ID NO: 16)
ASQLSTAQTARLAEFLHHSSDNFGPILPPTDVGSNTP (SEQ ID NO: 19)
ASHLSTAQTARLAEFLHHSSDPFGAIPSSTDVGPDTP.
```

59. The amylin receptor agonist according to any one of embodiments 251 to 58, wherein the peptide comprises a C-terminal amide.

60. The amylin receptor agonist according to any one of the preceding embodiments, which does not comprise an intact ring structure.

61. The amylin receptor agonist according to any one of the preceding embodiments, which does not comprise a disulfide bridge.

62. The amylin receptor agonist according to any one of the preceding embodiments, wherein the peptide does not comprise a cysteine (Cys, C) residue.

63. The amylin receptor agonist according to any one of the preceding embodiments, further comprising a protraction moiety.

64. The amylin receptor agonist according to the preceding embodiment, wherein the protraction moiety is attached to the alpha position of the alanine (Ala, A) at position 1 or to the epsilon position of a lysine (Lys, K) at position 25.

65. The amylin receptor agonist according to any one of the preceding embodiments 63 and 64, wherein the protraction moiety is represented by the formula (A)-(B), which is attached, via linker (A), to the alpha position of the alanine (Ala, A) at position 1 or to the epsilon position of a lysine (Lys, K) at position 25.

66. The amylin receptor agonist according to any one of preceding embodiments 64 and 65, wherein the protraction moiety is attached to the alpha position of the alanine (Ala, A) at position 1.

67. The amylin receptor agonist according to any one of the preceding embodiments 63 to 66, wherein the amino acid at position 25 is alanine (Ala, A) or Proline (Pro, P) when the protraction moiety is attached to the alanine (Ala, A) at position 1.

68. The amylin receptor agonist according to any one of the preceding embodiments 63 to 67, wherein the protraction moiety is attached to the epsilon position of lysine (Lys, K) at position 25.

69. The amylin receptor agonist according to the preceding embodiment, wherein the N-terminal amino acid is acylated.

70. The amylin receptor agonist according to embodiment 68, wherein the N-terminal amino acid is acetylated.

71. The amylin receptor agonist according to embodiment 68, wherein alanine at position 1 is Ac-Ala.

72. The amylin receptor agonist according to any one of the preceding embodiments 65 to 71, wherein the linker (A) of the protraction moiety comprises a moiety according to Chem. 8a or Chem. 8b.

73. The amylin receptor agonist according to the preceding embodiment, wherein the linker (A) of the protraction moiety comprises one or two moieties according to Chem. 8a or Chem. 8b.

74. The amylin receptor agonist according to any one of embodiments 72 and 73, wherein the linker (A) of the protraction moiety consists of one moiety according to Chem. 8a or Chem. 8b.

75. The amylin receptor agonist according to any one of embodiments 72 and 73, wherein the linker (A) of the protraction moiety consists of two moieties according to Chem. 8a or Chem. 8b.

76. The amylin receptor agonist according to any one of embodiments 72 and 73, wherein the linker (A) of the protraction moiety consists of one or two moieties according to Chem. 8a.

77. The amylin receptor agonist according to any one of embodiments 65 to 76, wherein the protractor (B) of the protraction moiety comprises a C14 diacid, a C16 diacid, a C18 diacid, a C20 diacid, a C18-tetrazole, a C14-sulfonic acid, 4-(9-carboxynonyloxy) benzoic acid, 4-(10-carboxydecyloxy) benzoic acid, or 3-(9-carboxynonyloxy) benzoic acid.

78. The amylin receptor agonist according to the preceding embodiment, wherein the protractor (B) of the protraction moiety comprises a C14 diacid, C16 diacid, C18 diacid, or C20 diacid.

79. The amylin receptor agonist according to the preceding embodiment, wherein the protractor (B) of the protraction moiety consists of a C18 diacid.

80. The amylin receptor agonist according to embodiment 78, wherein the protractor (B) of the protraction moiety consists of a C20 diacid.

81. An amylin receptor agonist according to formula:

Compound 2

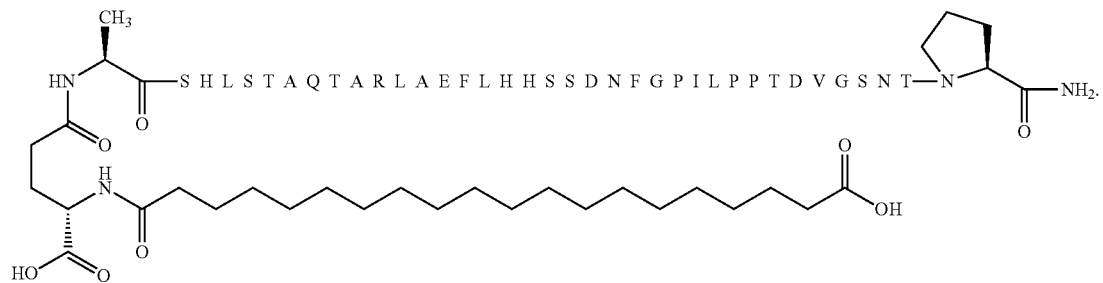

82. An amylin receptor agonist according to formula:

Compound 3

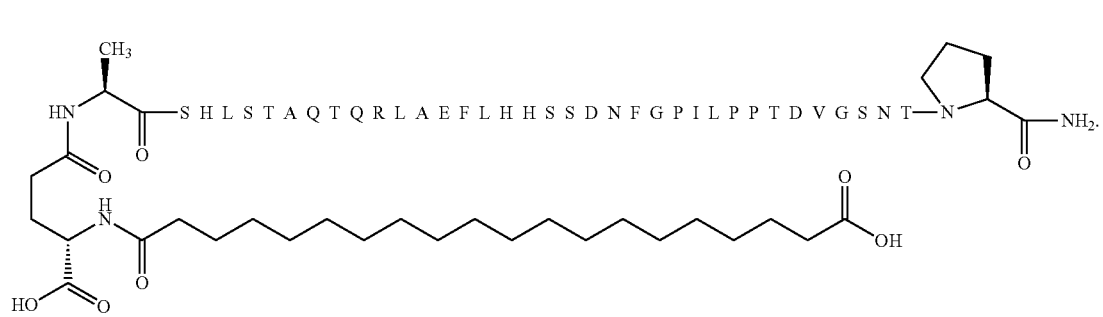

83. An amylin receptor agonist according to formula:

Compound 4

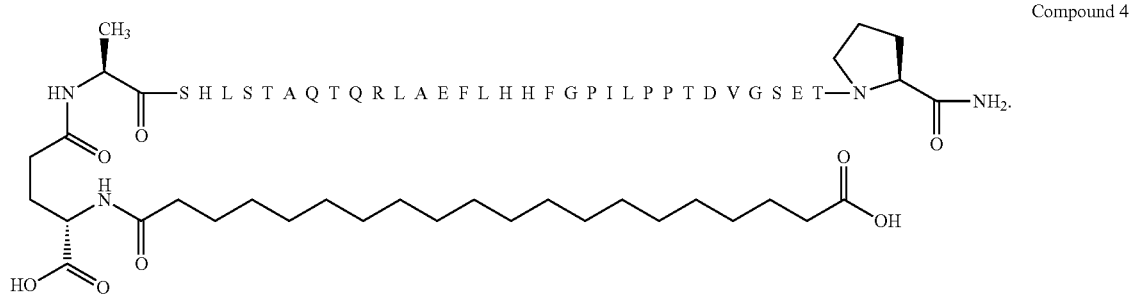

84. An amylin receptor agonist according to formula:
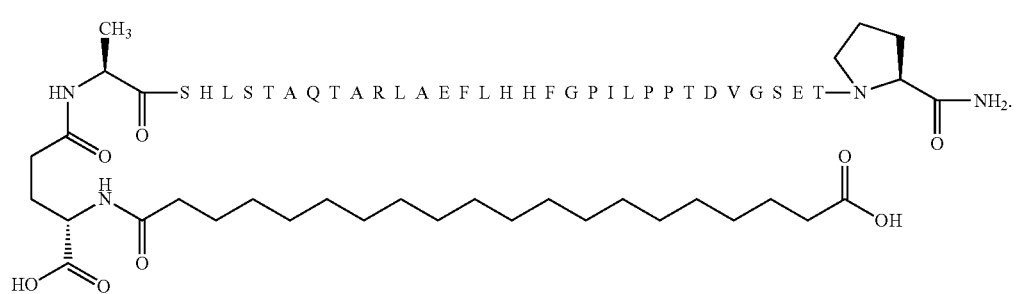
Compound 5
85. An amylin receptor agonist according to formula:
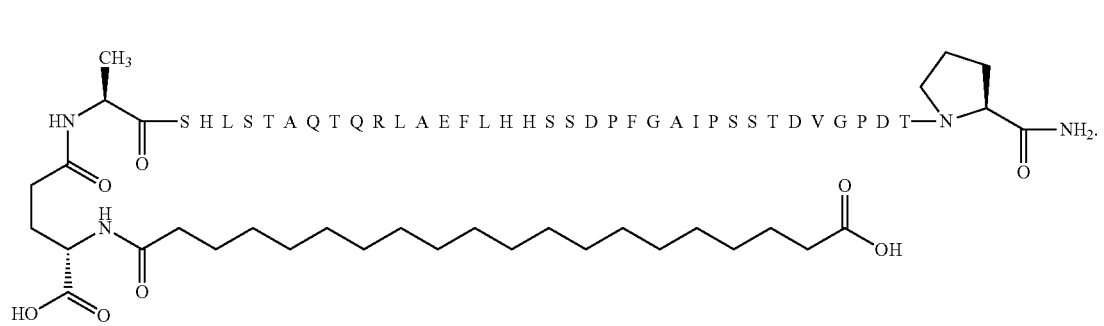
Compound 6
86. An amylin receptor agonist according to formula:
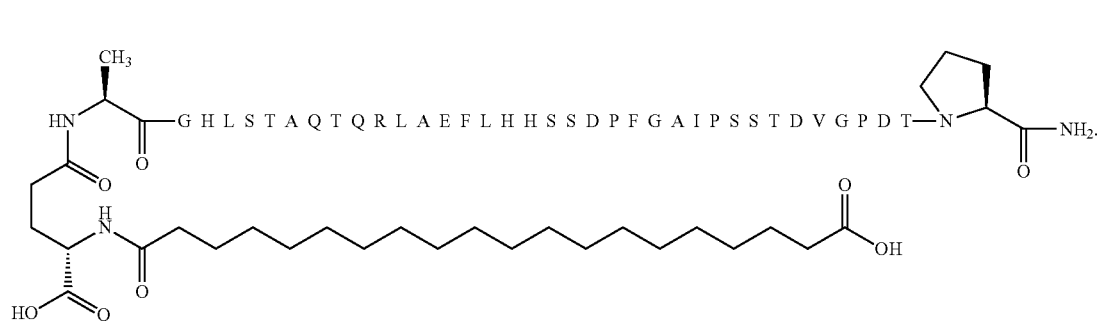
Compound 7
87. An amylin receptor agonist according to formula:
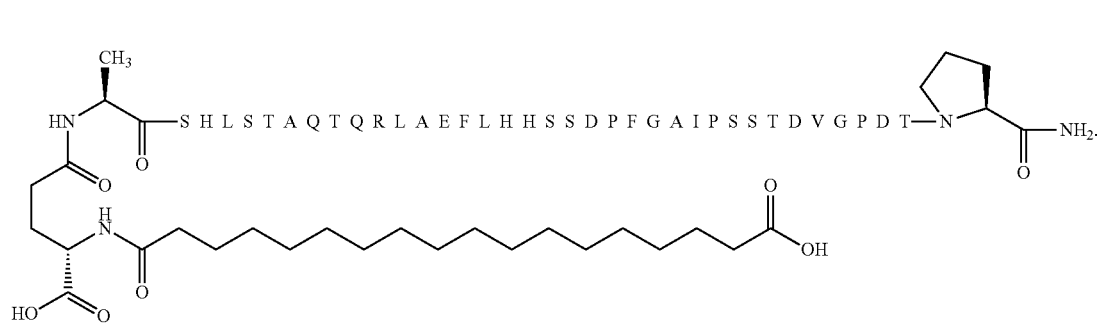
Compound 8

88. An amylin receptor agonist according to formula:
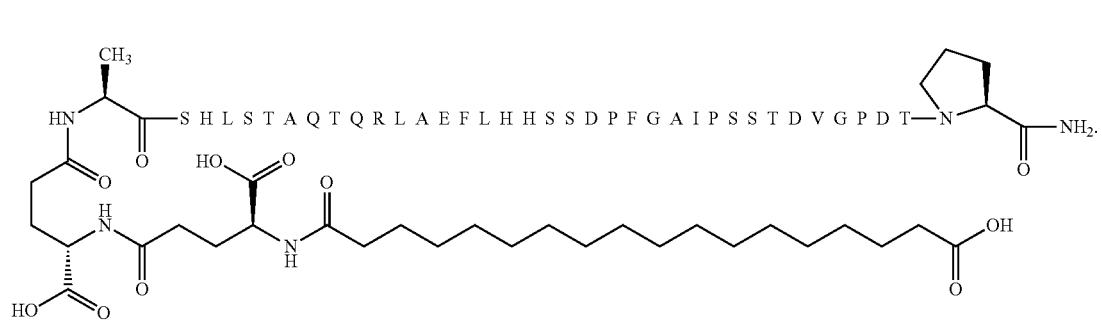
Compound 9
89. An amylin receptor agonist according to formula:
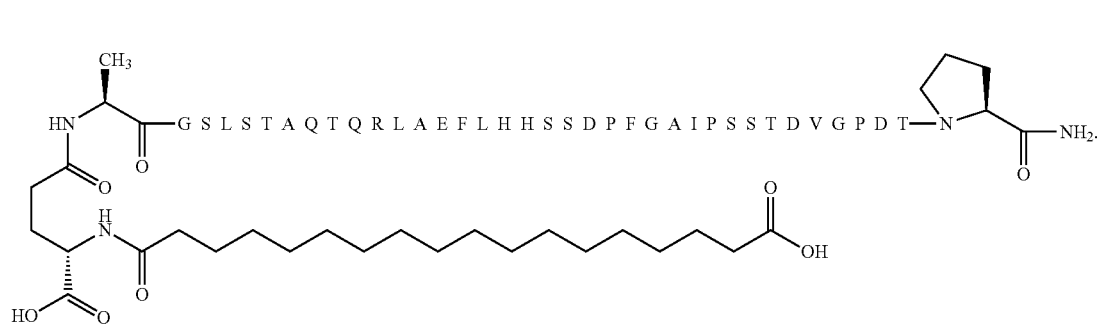
Compound 10
90. An amylin receptor agonist according to formula:
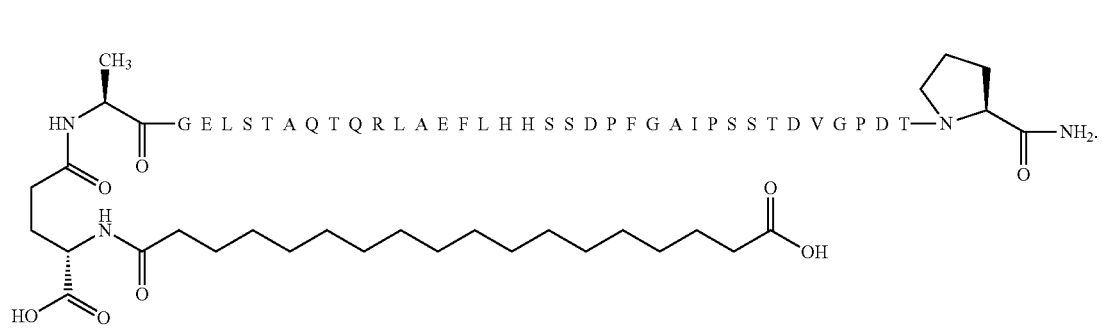
Compound 11
91. An amylin receptor agonist according to formula:
Compound 12

92. An amylin receptor agonist according to formula:
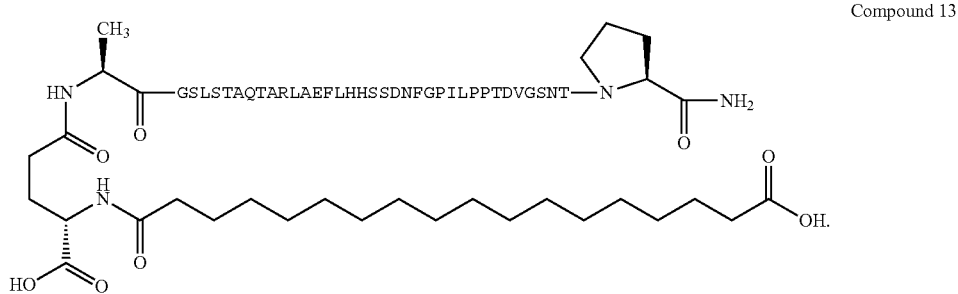
Compound 13
93. An amylin receptor agonist according to formula:
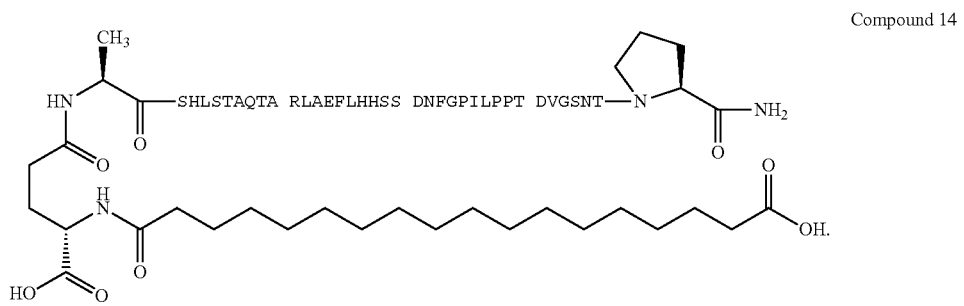
Compound 14
94. An amylin receptor agonist according to formula:
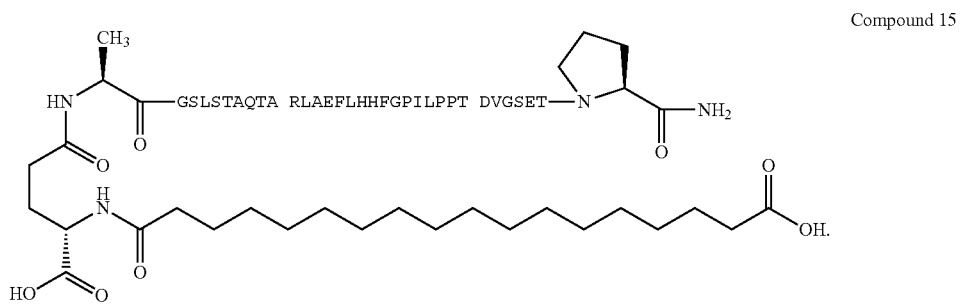
Compound 15
95. An amylin receptor agonist according to formula:
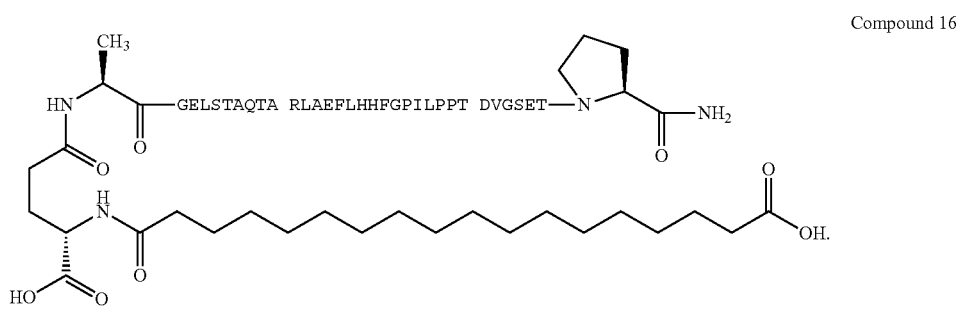
Compound 16

96. An amylin receptor agonist according to formula:
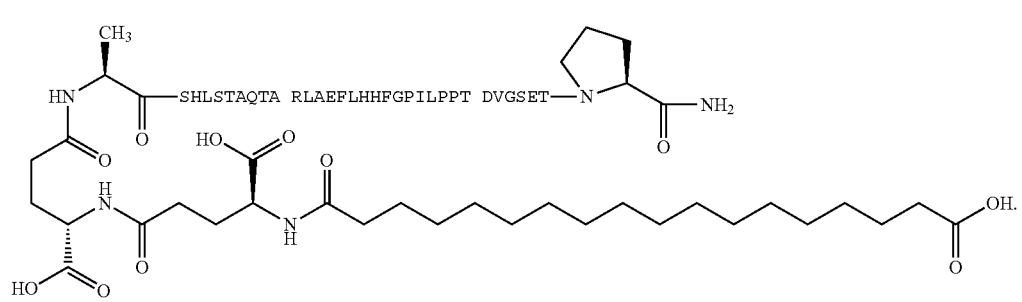
Compound 17
97. An amylin receptor agonist according to formula:
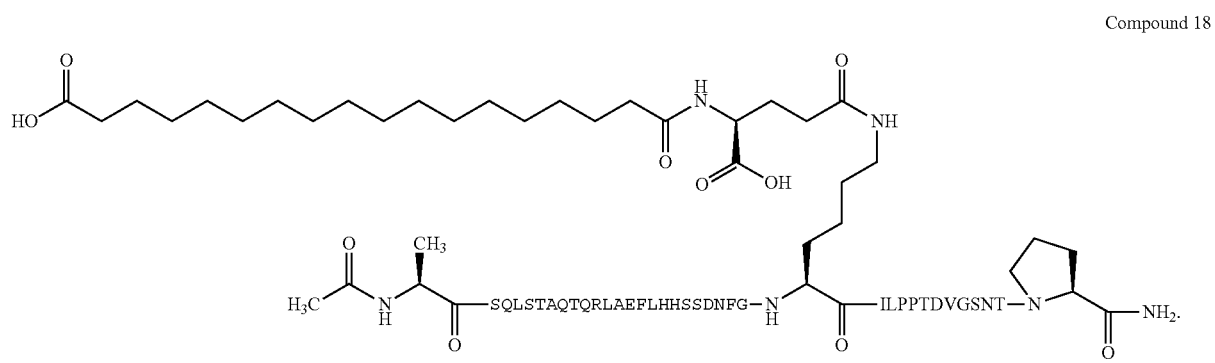
Compound 18
98. An amylin receptor agonist according to formula:
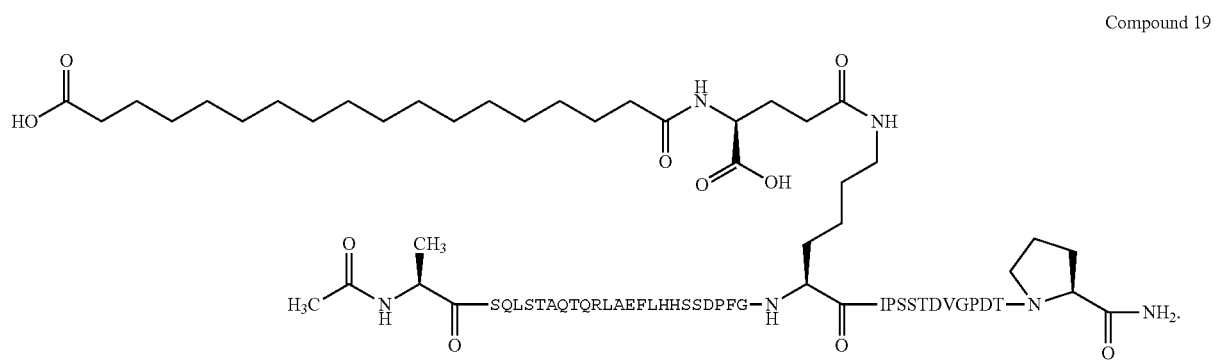
Compound 19
99. An amylin receptor agonist according to formula:
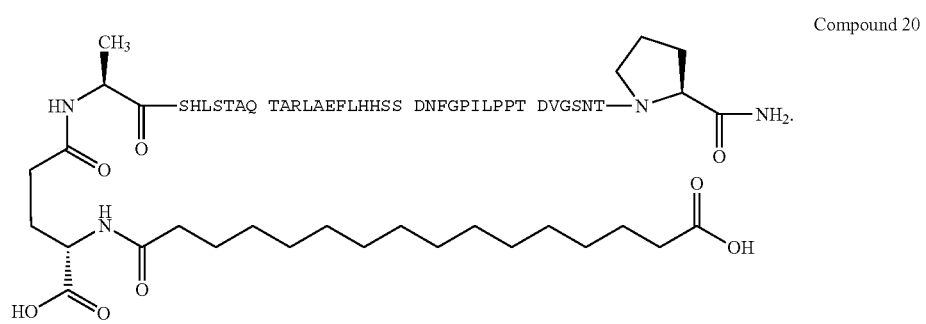
Compound 20

100. An amylin receptor agonist according to formula:
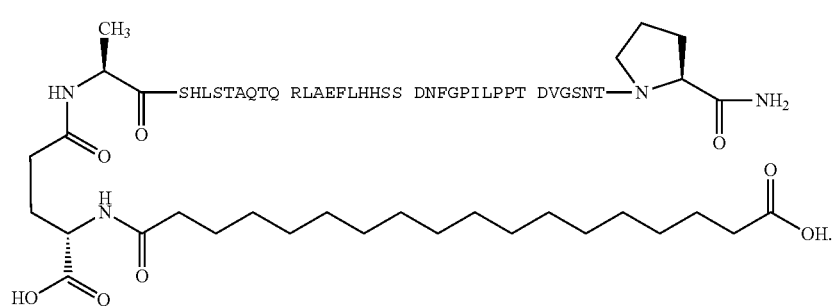
Compound 21
101. An amylin receptor agonist according to formula:
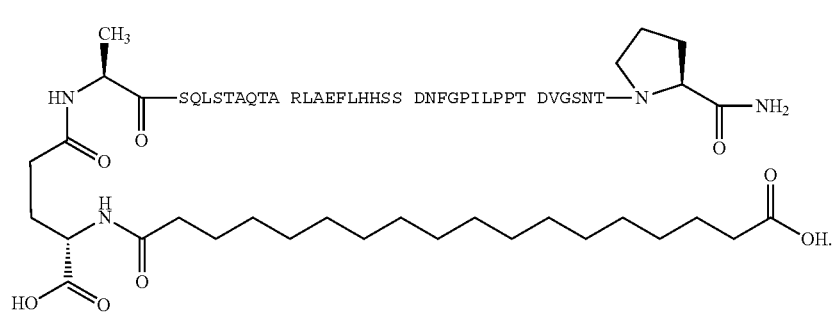
Compound 22
102. An amylin receptor agonist according to formula:
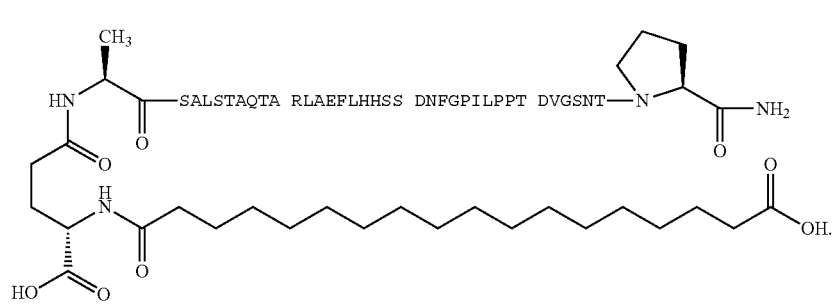
Compound 23
103. An amylin receptor agonist according to formula:
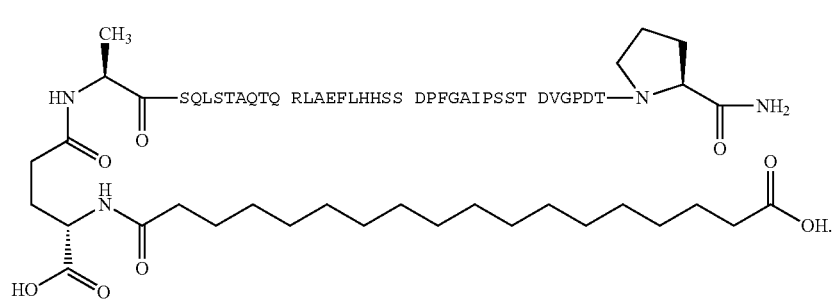
Compound 24

104. An amylin receptor agonist according to formula:
Compound 25
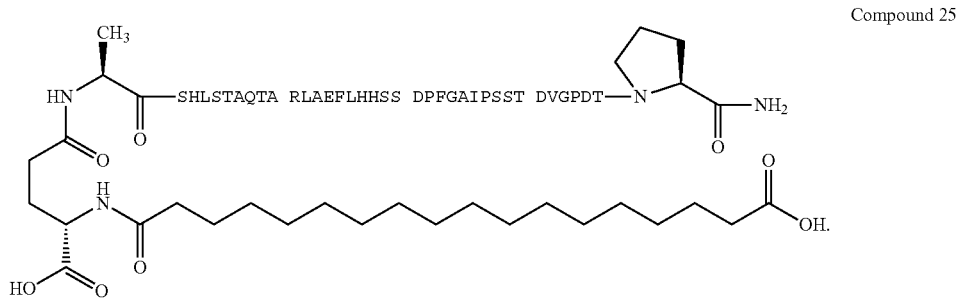
105. An amylin receptor agonist according to formula:
Compound 26
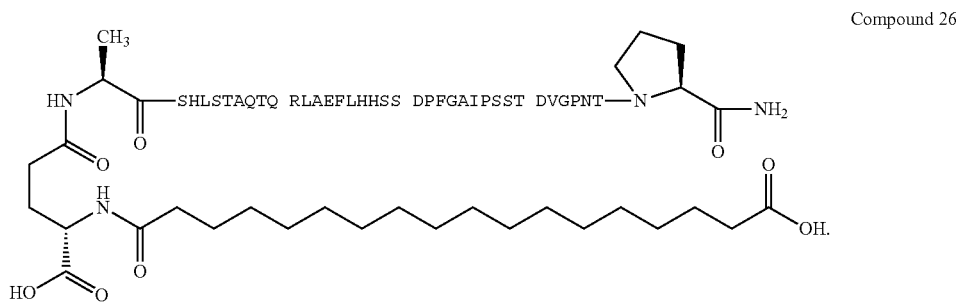
106. An amylin receptor agonist according to formula:
Compound 27
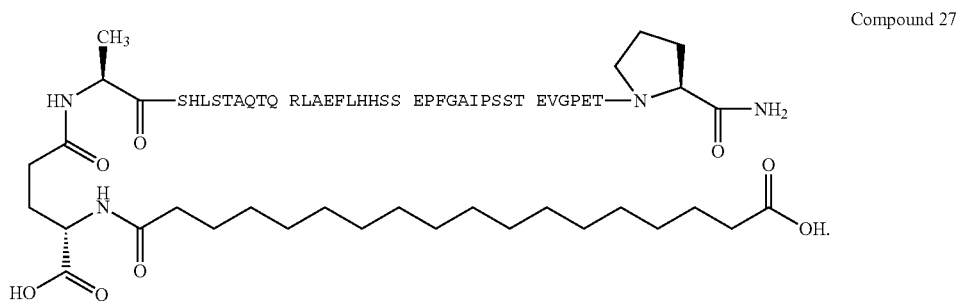
107. An amylin receptor agonist according to formula:
Compound 28
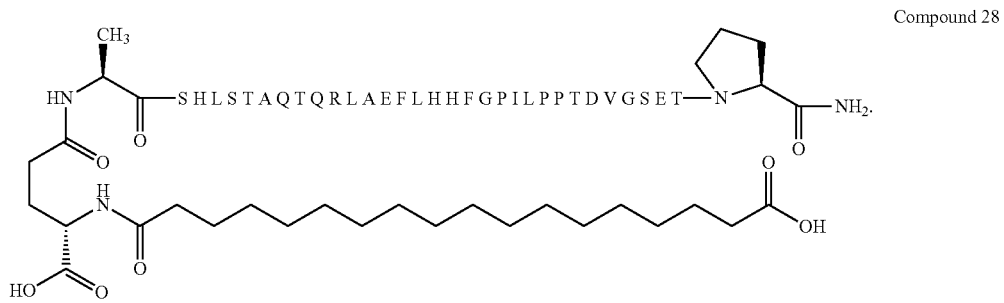

108. An amylin receptor agonist according to formula:
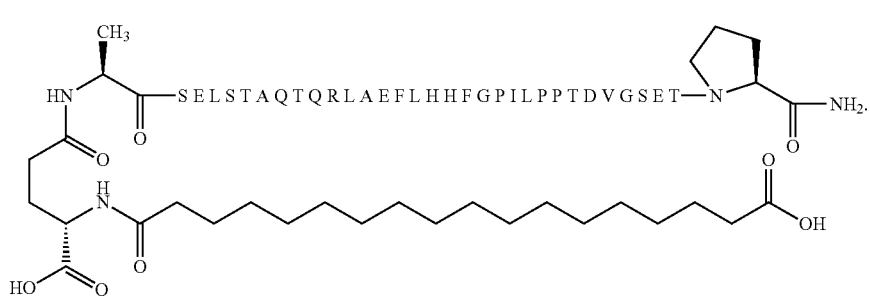
Compound 29
109. An amylin receptor agonist according to formula:
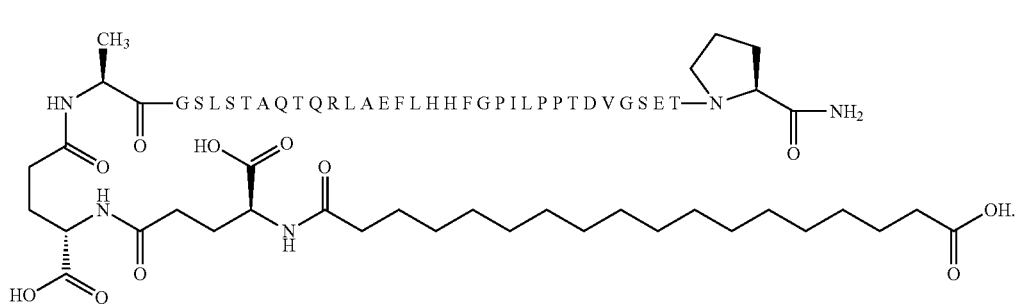
Compound 30
110. An amylin receptor agonist according to formula:
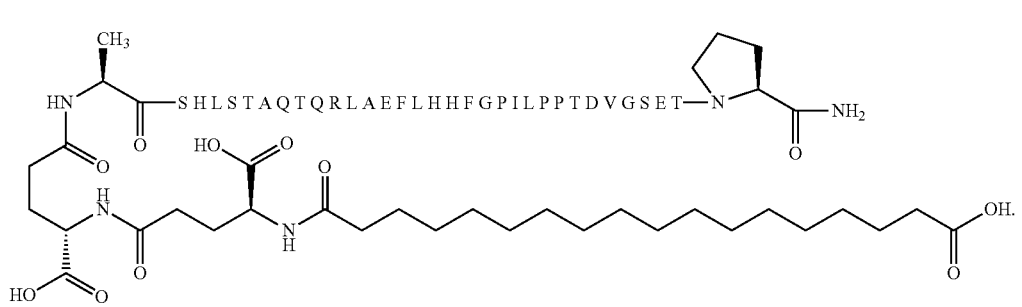
Compound 31
111. An amylin receptor agonist according to formula:
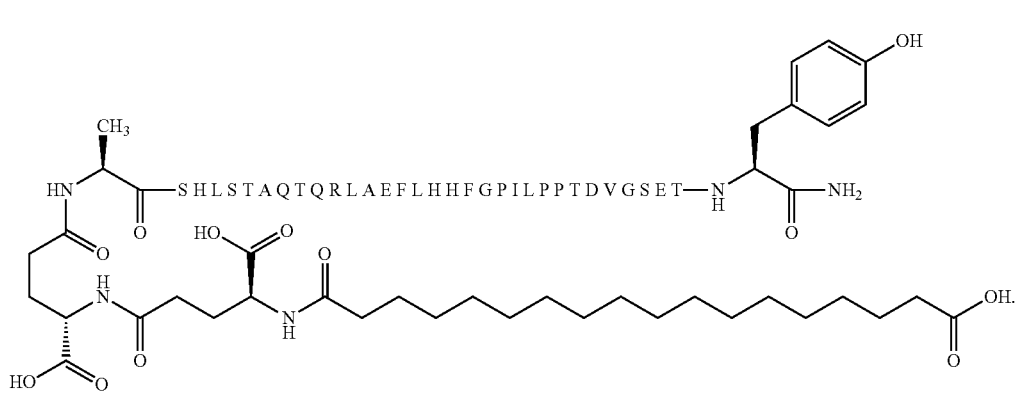
Compound 32

112. An amylin receptor agonist according to formula:
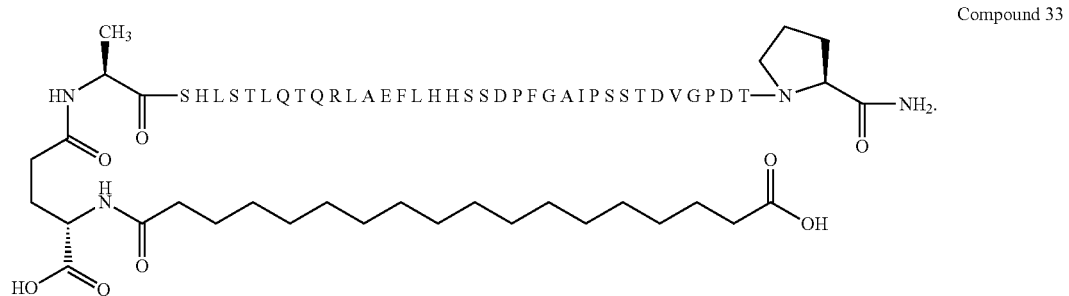
Compound 33
113. An amylin receptor agonist according to formula:
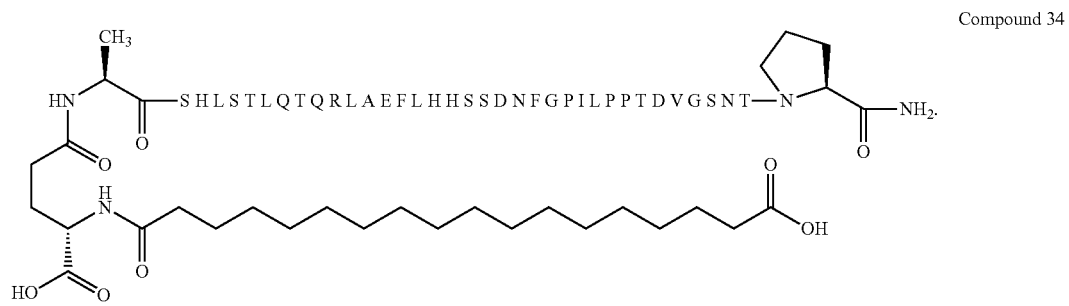
Compound 34
114. An amylin receptor agonist according to formula:
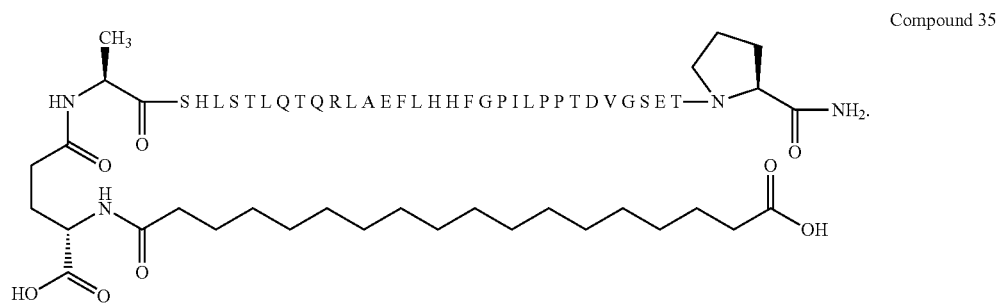
Compound 35
115. An amylin receptor agonist according to formula:
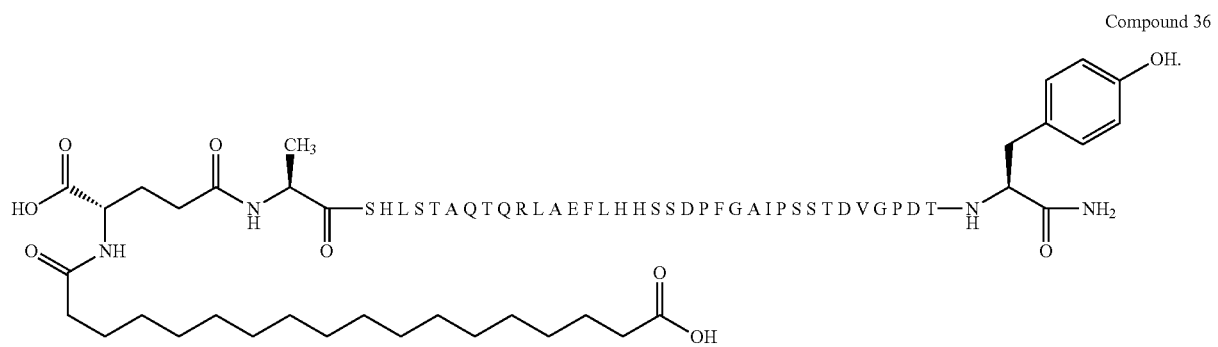
Compound 36

116. An amylin receptor agonist according to formula:
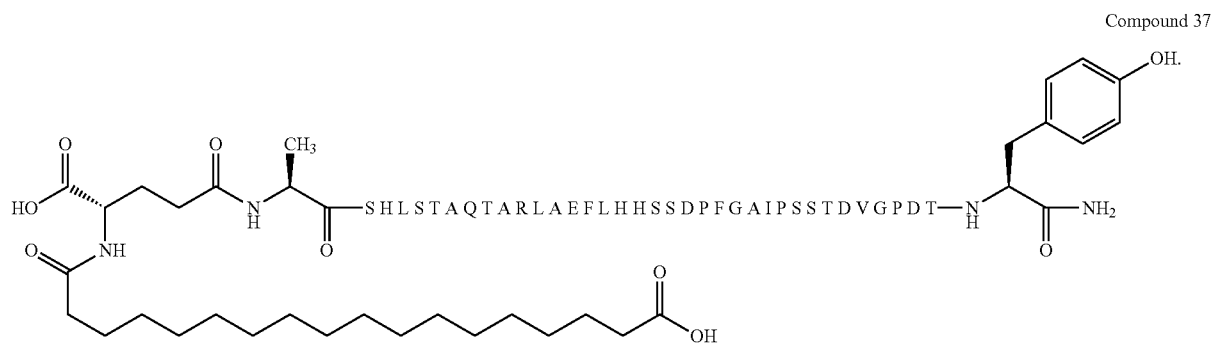
Compound 37
117. An amylin receptor agonist according to formula:
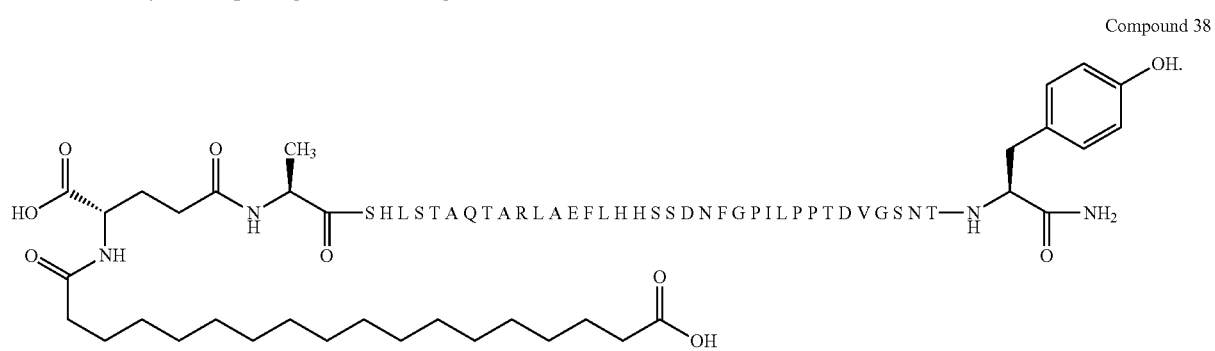
Compound 38
118. An amylin receptor agonist according to formula:
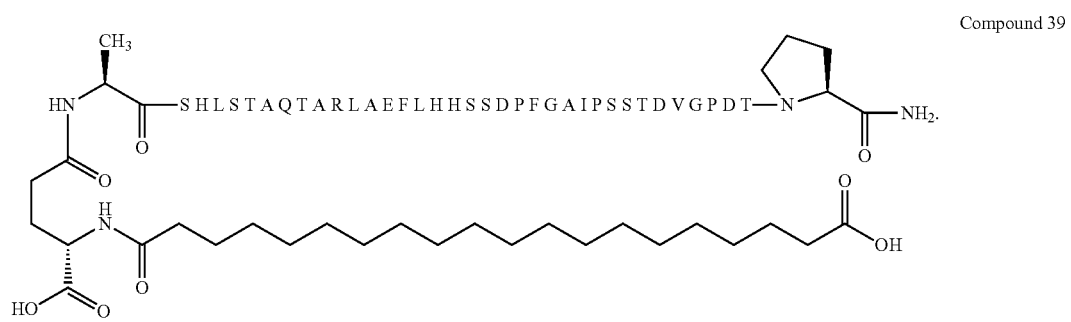
Compound 39
119. An amylin receptor agonist according to formula:
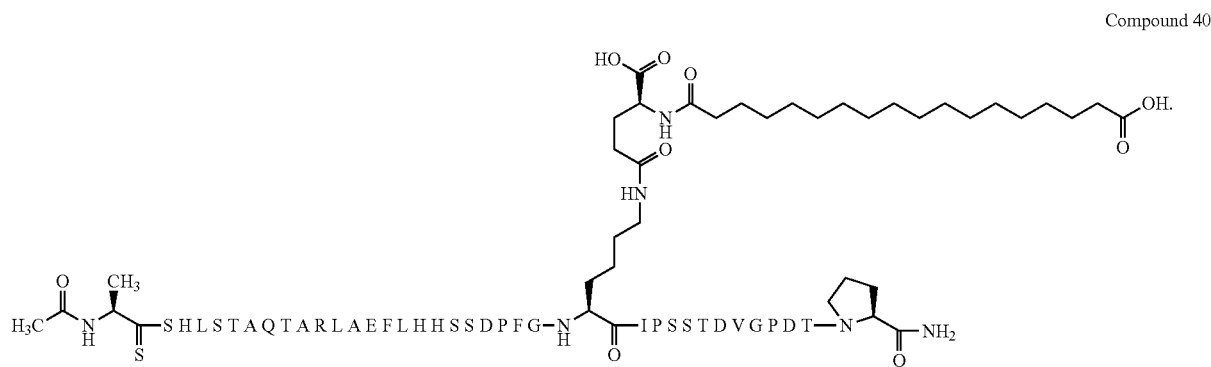
Compound 40

120. An amylin receptor agonist according to formula:

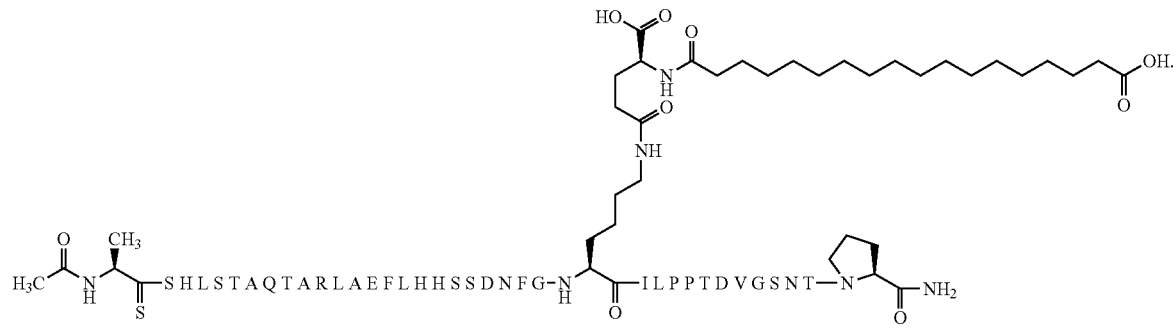

Compound 41

121. An amylin receptor agonist according to formula:

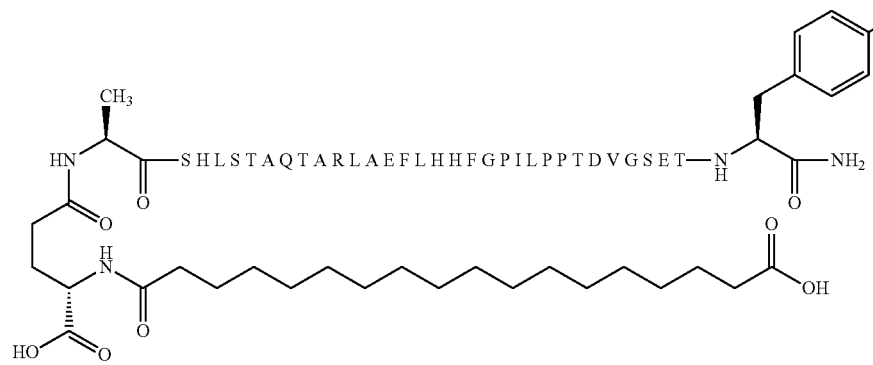

Compound 42

122. An amylin receptor agonist according to formula:

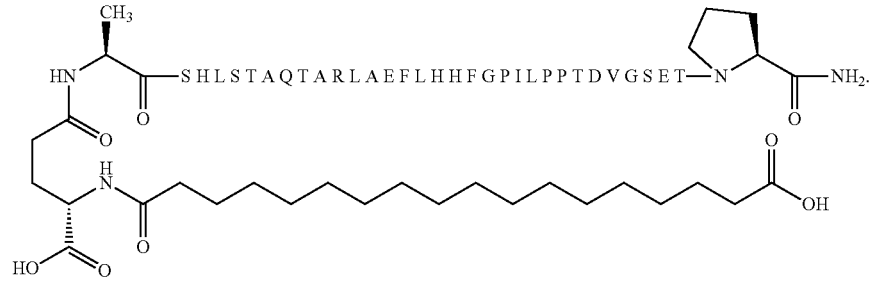

Compound 43

123. The amylin receptor agonist according to any one of the preceding embodiments, wherein the peptide comprises a C-terminal amide.

124. The amylin receptor agonist according to the preceding embodiment, wherein the amine group of the C-terminal amide is $NH_2$.

125. The amylin receptor agonist according to any one of preceding embodiments, with an $EC_{50}$ value of less than 10 pM, such as less than 7 pM, such as less than 5 pM, such as less than 3 pM, such as less than 2 pM, measured in an in vitro potency on the amylin-3 receptor according to the assay of Example 4.

126. The amylin receptor agonist according to any one of preceding embodiments, with an $EC_{50}$ value of less than 20 pM, such as less than 15 pM, such as less than 10 pM, such as less than 5 pM, such as less than 3 pM, such as less than 2 pM, measured in an in vitro potency on the calcitonin receptor according to the assay of Example 4.

127. The amylin receptor agonist according to any one of preceding embodiments, with a half-life [h] of at least 80 in Beagle dogs following oral administration, measured according to the assay of Example 5.

128. The amylin receptor agonist according to the preceding embodiment, with a half-life [h] of 80-150 in Beagle dogs following oral administration, measured according to the assay of Example 5.

129. The amylin receptor agonist according to any one of the preceding embodiments, wherein the oral bioavailability is suitable for oral dosing in humans.

130. The amylin receptor agonist according to any one of the preceding embodiments, wherein the oral bioavailability is determined in Beagle dogs, measured according to the assay of Example 5.

131. The amylin receptor agonist according to any one of the preceding embodiments, wherein the oral bioavailability is determined in Beagle dogs upon administration of tablets containing 3 mg of the compound, 300 mg sodium N-(8-(2-hydroxybenzoyl) amino)caprylate (SNAC) and 7.7 mg magnesium stearate.

132. The amylin receptor agonist according to any one of the preceding embodiments, wherein the oral bioavailability is measured as Cmax/Dose [kg/L].

133. The amylin receptor agonist according to any one of the preceding embodiments, wherein the oral bioavailability is measured as AUC/Dose [kg*hr/L].

134. The amylin receptor agonist according to any one of the preceding embodiments, wherein the oral bioavailability is measured as Cmax/Dose [kg/L] in Beagle dogs; and wherein the Cmax/Dose [kg/L] is at least 0.1.

135. The amylin receptor agonist according to any one of the preceding embodiments, wherein the oral bioavailability is measured as Cmax/Dose [kg/L] in Beagle dogs; and wherein the Cmax/Dose [kg/L] is at least 0.15.

136. The amylin receptor agonist according to any one of the preceding embodiments, wherein the oral bioavailability is measured as Cmax/Dose [kg/L] in Beagle dogs; and wherein the Cmax/Dose [kg/L] is 0.1-0.5.

137. The amylin receptor agonist according to any one of the preceding embodiments, wherein the oral bioavailability is measured as AUC/Dose [kg*hr/L] in Beagle dogs; and wherein the AUC/Dose [kg*hr/L] is at least 10.

138. The amylin receptor agonist according to any one of the preceding embodiments, wherein the oral bioavailability is measured as AUC/Dose [kg*hr/L] in Beagle dogs; and wherein the AUC/Dose [kg*hr/L] is 10-40.

139. The amylin receptor agonist according to any one of the preceding embodiments, wherein the amylin receptor agonist reduces appetite.

140. The amylin receptor agonist according to any one of the preceding embodiments, wherein the amylin receptor agonist reduces food intake.

141. The amylin receptor agonist according to any one of the preceding embodiments, wherein the amylin receptor agonist reduces body weight.

142. The amylin receptor agonist according to any one of the preceding embodiments, showing food intake reduction in rats tested according to the assay of Example 6 after administration of 3 nmol/kg.

143. The amylin receptor agonist according to any one of the preceding embodiments, showing reduction in food intake in rats tested according to the assay of Example 6 of which can be seen within 0-24 hours after administration of 3 nmol/kg.

144. The amylin receptor agonist according to any one of the preceding embodiments, showing reduction in food intake in rats tested according to the assay of Example 6 which can be seen within 0-24 and/or 24-48 hours after administration of 3 nmol/kg.

145. The amylin receptor agonist according to any one of the preceding embodiments, showing reduction in food intake by at least 10% in rats tested according to the assay of Example 6 which can be seen within 0-24 hours after administration of 3 nmol/kg.

146. The amylin receptor agonist according to any one of the preceding embodiments, showing reduction in food intake by at least 10% in rats tested according to the assay of Example 6 which can be seen within 24-48 hours after administration of 3 nmol/kg.

147. A pharmaceutically acceptable salt of the amylin receptor agonist according to any one of the preceding embodiments.

148. A pharmaceutically acceptable ester of the amylin receptor agonist according to any one of embodiments 1 to 146.

149. A pharmaceutically acceptable amide of the amylin receptor agonist according to any one of embodiments 1 to 146.

150. A pharmaceutical composition comprising the amylin receptor agonist and/or pharmaceutically acceptable salt, ester, or amide thereof, according to any one of the preceding embodiments, and one or more pharmaceutically acceptable excipients.

151. The pharmaceutical composition according to the preceding embodiment, which is for oral administration.

152. The pharmaceutical composition according to the preceding embodiment, which is a solid pharmaceutical composition.

153. The pharmaceutical composition according to the preceding embodiment, which is a tablet.

154. The tablet according to the preceding embodiment, wherein the compound is formulated with sodium N-(8-[2-hydroxybenzoyl] amino) caprylate (SNAC).

155. The tablet according to the preceding embodiment, wherein the compound is further formulated with a lubricant magnesium stearate.

156. The pharmaceutical composition according to any one of embodiments 153 to 155, which is for dosing approximately once daily, such as once every 12-36 hours, such as once every 18-30 hours, such as approximately once every 24 hours.

157. The pharmaceutical composition according to embodiment 150, which is a liquid formulation.

158. The pharmaceutical composition according to the preceding embodiment, which is for dosing approximately once weekly.

159. The pharmaceutical composition according to any one of embodiments 157 and 158, wherein the liquid formulation provides an improved stability.

160. An amylin receptor agonist according to any one of embodiments 1 to 146 or the pharmaceutical composition according to any one of embodiments 150 to 159 for use as a medicament.

161. An amylin receptor agonist according to any one of embodiments 1 to 146 or the pharmaceutical composition according to any one of embodiments 150 to 159, for use in the treatment of subjects with an initial body mass index (BMI) of 27 or more, such as 30 or more.

162. An amylin receptor agonist according to any one of embodiments 1 to 146 or the pharmaceutical composition according to any one of embodiments 150 to 159, for use in the treatment of subjects with an initial body mass index (BMI) of 27 or more and at least one weight-related co-morbidity.

163. An amylin receptor agonist according to any one of embodiments 1 to 146 or the pharmaceutical composition according to any one of embodiments 150 to 159, for use as an adjunct to a reduced-calorie diet and increased physical activity for chronic weight management in adult subjects with an initial body mass index (BMI) of 30 or greater (obesity) or 27 or greater (overweight) in the presence of at least one weight-related co-morbidity.

164. The amylin receptor agonist according to any one of embodiments 162 and 163, wherein the co-morbidity is diabetes and/or a cardiovascular disease.

165. An amylin receptor agonist according to any one of embodiments 1 to 146 or the pharmaceutical composition according to any one of embodiments 150 to 159, for use in the treatment of subjects with diabetes, such as type II diabetes.

166. An amylin receptor agonist according to any one of embodiments 1 to 146 or the pharmaceutical composition according to any one of embodiments 150 to 159, for use in the treatment and/or prevention of cardiovascular disease.

167. An amylin receptor agonist according to any one of embodiments 1 to 146 or the pharmaceutical composition according to any one of embodiments 150 to 159, for use in the treatment of non-alcoholic steatohepatitis.

168. An amylin receptor agonist according to any one of embodiments 1 to 146 or the pharmaceutical composition according to any one of embodiments 150 to 159, for use in the treatment and/or prevention of cognitive impairment, such as that caused by Alzheimer's disease.

169. A pharmaceutical co-formulation or co-treatment comprising an amylin receptor agonist according to any one of embodiments 1 to 146, and further comprising one or more GLP-1 receptor agonist(s) and/or GLP-1-GIP receptor agonist(s).

170. The pharmaceutical co-formulation or co-treatment according to the preceding embodiment, wherein the one or more GLP-1 receptor agonist(s) and/or GLP-1-GIP receptor agonist(s) is a peptide GLP-1 receptor agonist or peptide GLP-1-GIP receptor agonist, or a small molecule GLP-1 receptor agonist or small molecule GLP-1-GIP receptor agonist.

171. The pharmaceutical co-formulation or co-treatment according to the preceding embodiment, wherein the one or more GLP-1-GIP receptor agonist(s) is a peptide GLP-1-GIP receptor agonist or a small molecule GLP-1-GIP receptor agonist.

172. A pharmaceutical co-formulation or co-treatment comprising an amylin receptor agonist according to any one of embodiments 1 to 146, and further comprising one or more peptide(s).

173. The pharmaceutical co-formulation or co-treatment according to the preceding embodiment, wherein at least one of the one or more peptide(s) is for the treatment and/or prevention of diabetes, a cardiovascular disease, non-alcoholic steatohepatitis, and/or Alzheimer's disease.

174. The pharmaceutical co-formulation or co-treatment according to the any one of embodiments 172 and 173, wherein at least one of the one or more peptide(s) is a GLP-1 peptide.

175. The pharmaceutical co-formulation or co-treatment according to the preceding embodiment, wherein the GLP-1 peptide is a GLP-1 compound, GLP-1 analogue, or GLP-1 derivative.

176. The pharmaceutical co-formulation or co-treatment according to the preceding embodiment, wherein the GLP-1 compound, GLP-1 analogue, or GLP-1 derivative is semaglutide, liraglutide, or tirzepatide.

177. The pharmaceutical co-formulation or co-treatment according to any one of embodiments 169 to 176, wherein at least one of the one or more peptide(s) is a GLP-1-GIP receptor co-agonist.

178. The pharmaceutical co-formulation or co-treatment according to any one of embodiments 169 to 177, wherein at least one of the one or more peptide(s) is an insulin peptide.

179. The pharmaceutical co-formulation or co-treatment according to the preceding embodiment, wherein the insulin peptide is an insulin compound, insulin analogue, or insulin derivative.

180. A method for preparing the amylin receptor agonist according to any one of embodiments 1 to 146.

181. The method according to the preceding embodiment, comprises a step of solid phase peptide synthesis.

EXAMPLES

The following are non-limiting examples for carrying out the invention.
Synthesis of Amylin Analogues and Comparator Compounds
This example provides the identity, materials for making and methods of synthesis of many compounds according to the current invention.
Also provided are the identity, materials for making and methods of synthesis of the comparator compounds described herein.

LIST OF ABBREVIATIONS

The following abbreviations are used in the following, in alphabetical order:
Ac: acetyl
AUC: Area Under the Curve
Boc: t-butyloxycarbonyl
DCM: dichloromethane
DIC: diisopropylcarbodiimide
DIPEA: N,N-diisopropylethylamine or Hünig's base
DMF: dimethyl formamide
DTT: dithiothreitol
EDTA: ethylenediaminetetraacetic acid
ELISA: Enzyme Linked Immuno Sorbent Assay
Fmoc: 9-fluorenylmethyloxycarbonyl
HFIP: 1,1,1,3,3,3-hexafluoro-2-propanol or hexafluoroisopropanol
HOBt: 1-hydroxybenzotriazole
HPLC: High Performance Liquid Chromatography
Imp: imidazolepropionyl
i.v.: intravenously
LCMS or LC-MS: Liquid Chromatography Mass Spectrometry
MeCN: acetonitrile
Mtt: 4-methyltrityl
NHS: N-hydroxysuccinimide
NMP: N-methyl pyrrolidone
Oxyma Pure®: cyano-hydroxyimino-acetic acid ethyl ester
PK: pharmacokinetic
QTof: Quantitative Time of Flight
s.c.: subcutaneously
SD Standard Deviation
SEC-HPLC: Size Exclusion High Performance Liquid Chromatography
SEM: Standard Error of Mean
tBu: t-butyl
TFA: trifluoroacetic acid
TIPS: triisopropylsilane
Trt: triphenylmethyl or trityl
Trx tranexamic acid
UPLC: Ultra Performance Liquid Chromatography
General Methods of Preparation
This section relates to general methods for solid phase peptide synthesis (SPPS methods, including methods for cleaving the peptide from the resin and removal of the protecting groups and for its purification). Included as well are LCMS methods for detecting and characterizing the resulting peptide.
Fatty Acid and Special Amino Acid Building Blocks
For synthesis of octadecanedioic acid mono-tert-butyl ester: see patent application WO 2010/102886 (pages 27-28). The corresponding mono-tert-butyl esters of C16- and C20 diacid can be prepared accordingly.

Fmoc-Gln(Trt)-Thr($\psi^{Me,Me}$pro)-OH was commercially available from TechnoComm Ltd.

Synthesis of the Derivatives of the Invention

General Synthesis Method

The preparation of the peptide was carried out with SPPS using Fmoc based chemistry on a Symphony X from Protein Technologies. The Fmoc-protected amino acids used in the methods were the standard recommended: Fmoc-Ala-OH, Fmoc-Arg(Pbf)-OH, Fmoc-Asp(OtBu)-OH, Fmoc-Asn(Trt)-OH, Fmoc-Cys(Trt)-OH, Fmoc-Gln(Trt)-OH, Fmoc-Glu(OtBu)-OH, Fmoc-Gly-OH, Fmoc-His(Trt)-OH, Fmoc-Ile-OH, Fmoc-Leu-OH, Fmoc-Phe-OH, Fmoc-Pro-OH, Fmoc-Ser(tBu)-OH, Fmoc-Thr(tBu)-OH, Fmoc-Trp(Boc)-OH, Fmoc-Tyr(tBu)-OH, Fmoc-Val-OH, Fmoc-Lys(Boc)-OH, Fmoc-Glu-OtBu, and Fmoc-Lys(Mtt)-OH supplied from e.g. Anaspec, Bachem, Iris Biotech or NovabioChem.

A Fmoc-PAL AM resin was used, which was commercially available from NovabioChem. The subsequent amino acids were introduced in a stepwise procedure by the Symphony X peptide synthesizer following the SPPS principles.

Fmoc-deprotection was achieved with 20% piperidine in DMF with 0.3 M Oxyma Pure for 2×10 min. Introduction of the substituent at the alpha-position of the N-terminal amino acid was accomplished using a standard Fmoc-protected amino acid. The peptide couplings were performed with DIC/Oxyma Pure and collidine. Amino acid/Oxyma Pure solutions (0.3 M/0.3 M in DMF at a molar excess of 5-10-fold) was added to the resin first. Then, the same molar equivalent of DIC was added (1.5 M in DMF), followed by collidine (1.5 M in DMF). Most commonly, it was mixed for 2 hours. In some cases, the coupling time was increased, additional DIC was added, or the coupling step was repeated. Afterwards, a capping step was performed with 1 M acetic anhydride in DMF and collidine. The building block Fmoc-Gln(Trt)-Thr($\psi^{Me,Me}$Pro)-OH was introduced in the positions corresponding to 8 and 9 in the full length sequence where applicable.

Introduction of the final element of the moiety (i.e. the fatty acid group) was achieved using the suitable building block, such as but not limited to, octadecanedioic acid mono-tert-butyl-ester. Where relevant, acetyl groups on the N-terminal was introduced by acetylation with 1 M acetic anhydride in DMF and collidine.

Introduction of a substituent/protraction moiety on the epsilon-amino of a lysine within the sequence was achieved using Fmoc-Lys(Mtt)-OH. The Mtt group was removed by treatment with HFIP/DCM/TIPS (75:20:5) (5 min), followed by a wash with DCM. The resin was then resuspended in HFIP/DCM/TIPS (75:20:5) (2×30 min), and subsequently washed with DCM and DMF before the substituent/protraction moiety was introduced at the epsilon-amino of the lysine. In these cases, the last amino acid introduced before the Mtt removal was Boc protected, or an acetyl group was introduced as described previously.

General Cleavage Method

The peptides were cleaved with TFA/TIPS/H2O/DTT (90:4:3:3) for 2 hours. Hereafter, it was drained into cold diethyl ether, and centrifuged. The ether was decanted off, and the peptide was washed with ether two additional times.

General Method for Purification and Quantification of the Derivative

The crude peptide was dissolved in Acetic Acid/Acetonitrile/MQ water (4:2:4) and purified by reversed-phase preparative HPLC (Waters Delta Prep 4000) on a column comprising C18-silica gel. Elution was performed with an increasing gradient of MeCN in MQ water comprising 0.1% TFA. Relevant fractions were analysed with UPLC. Fractions containing the pure target peptide were pooled. The resulting solution was analyzed (UPLC, LCMS) and the peptide derivative was quantified using a CAD specific HPLC detector (Thermo-Fischer Vanquish HPLC-CAD). The product was dispensed into glass vials. The vials were capped with Millipore glassfibre prefilters. Freeze-drying afforded the trifluoroacetate salt of the derivative as a white solid.

Manufactured Compounds

The compounds were prepared using the methods described under the section General methods of preparation.

Example 1: Reference Compounds

Compound 1

$N^1$Alpha-[(4S)-4-carboxy-4-(19-carboxynonadecanoylamino)butanoyl]-[Glu14,Arg17,Pro25,Pro28,Pro29,Gln31,Pro37]-human amylin

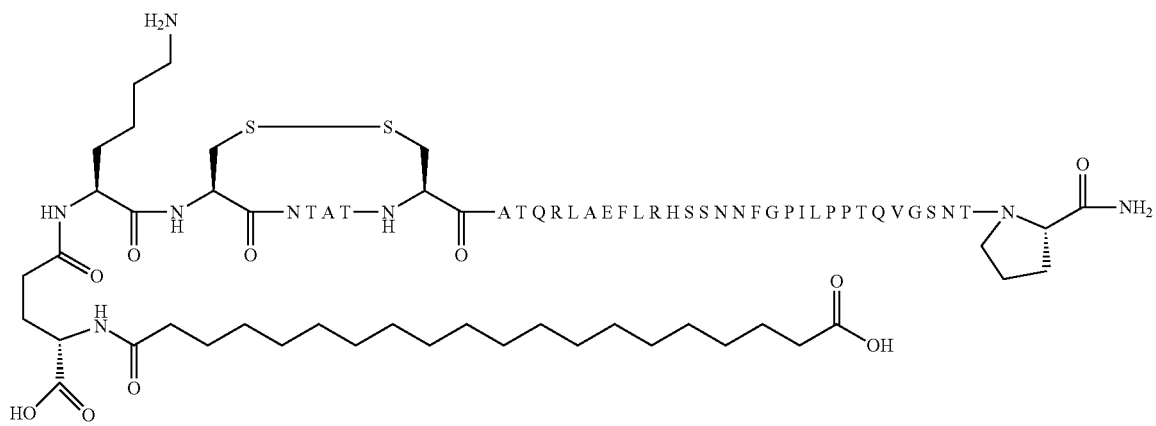

Example 2: Amylin Receptor Agonists According to the Invention

Compound 2

N$^1$-[(4S)-4-carboxy-4-(19-carboxynonadecanoylamino)butanoyl]-[Ala1,Ser2,His3,Leu4,Ser5,Ala7,Gln8,Ala10,Glu14,His17,Asp21,Pro25,Pro28,Pro29,Asp31,Pro37]-human amylin

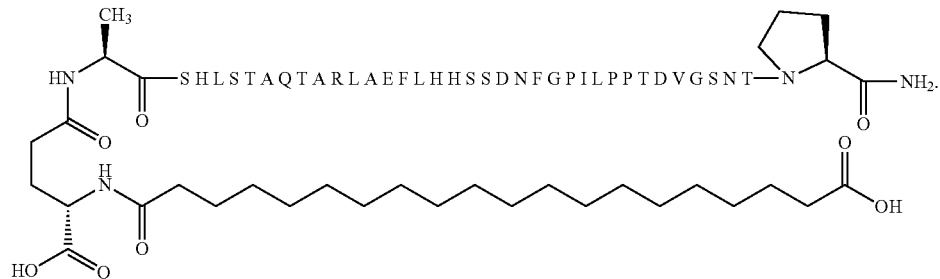

Compound 3

N$^1$-[(4S)-4-carboxy-4-(19-carboxynonadecanoylamino)butanoyl]-[Ala1,Ser2,His3,Leu4,Ser5,Ala7,Gln8,Glu14,His17,Asp21,Pro25,Pro28,Pro29,Asp31,Pro37]-human amylin

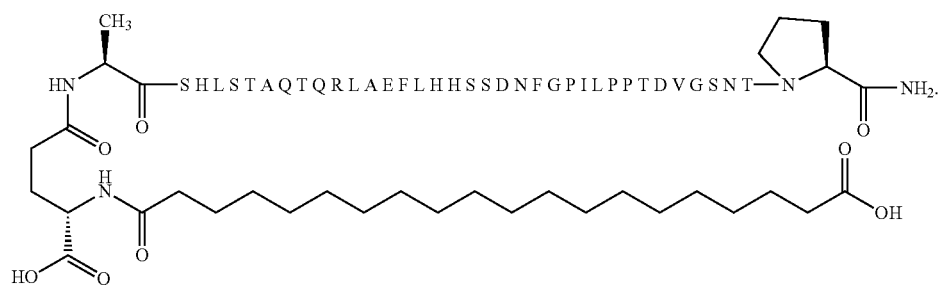

Compound 4

N$^1$-[(4S)-4-carboxy-4-(19-carboxynonadecanoylamino)butanoyl]-[Ala1,Ser2,His3,Leu4,Ser5,Ala7,Gln8,Glu14,His17,Pro25,Pro28,Pro29,Asp31,Glu35,Pro37],des-(19-22)-human amylin

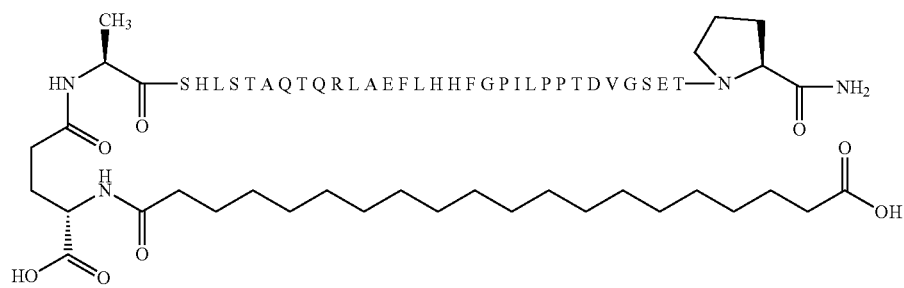

Compound 5

N$^1$-[(4S)-4-carboxy-4-(19-carboxynonadecanoy-
lamino)butanoyl]-[Ala1,Ser2,His3,Leu4,Ser5,Ala7,
Gln8,Ala10,Glu14,His17,Pro25,Pro28,Pro29,Asp31,
Glu35,Pro37],des-(19-22)-human amylin

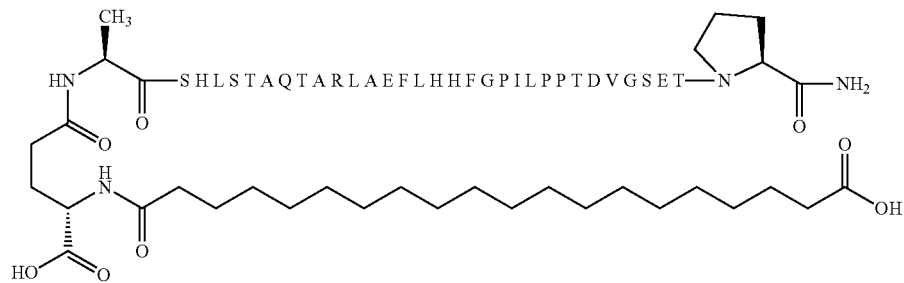

Compound 6

N$^1$-[(4S)-4-carboxy-4-(19-carboxynonadecanoy-
lamino)butanoyl]-[Ala1,Ser2,His3,Leu4,Ser5,Ala7,
Gln8,Glu14,His17,Asp21,Pro22,Pro27,Asp31,Pro34,
Asp35,Pro37]-human amylin

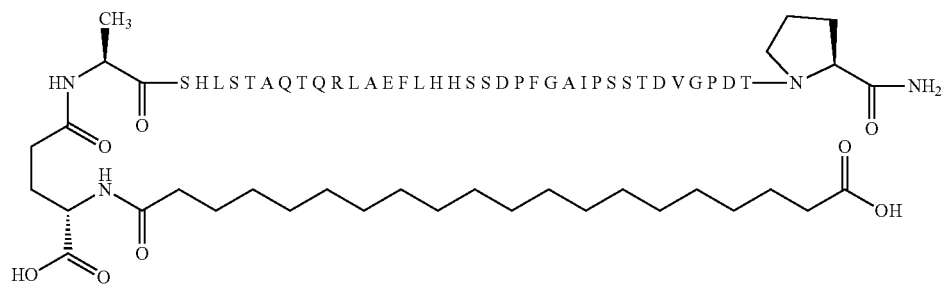

Compound 7

N$^1$-[(4S)-4-carboxy-4-(19-carboxynonadecanoy-
lamino)butanoyl]-[Ala1,Gly2,His3,Leu4,Ser5,Ala7,
Gln8,Glu14,His17,Asp21,Pro22,Pro27,Asp31,Pro34,
Asp35,Pro37]-human amylin

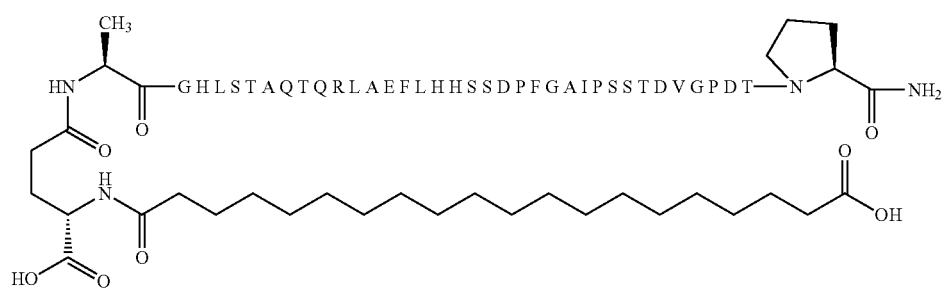

Compound 8

N¹-[(4S)-4-carboxy-4-(17-carboxyheptadecanoylamino)butanoyl]-[Ala1,Ser2,His3,Leu4,Ser5,Ala7,Gln8,Glu14,His17,Asp21,Pro22,Pro27,Asp31,Pro34,Asp35,Pro37]-human amylin

Compound 9

N¹-[(4S)-4-carboxy-4-[[(4S)-4-carboxy-4-(17-carboxyheptadecanoylamino)butanoyl]amino]butanoyl]-[Ala1,Ser2,His3,Leu4,Ser5,Ala7,Gln8,Glu14,His17,Asp21,Pro22,Pro27,Asp31,Pro34,Asp35,Pro37]-human amylin

Compound 10

N¹-[(4S)-4-carboxy-4-(17-carboxyheptadecanoylamino)butanoyl]-[Ala1,Gly2,Ser3,Leu4,Ser5,Ala7,Gln8,Glu14,His17,Asp21,Pro22,Pro27,Asp31,Pro34,Asp35,Pro37]-human amylin

Compound 11

$N^1$-[(4S)-4-carboxy-4-(17-carboxyheptadecanoylamino)butanoyl]-[Ala1,Gly2,Glu3,Leu4,Ser5,Ala7, Gln8,Glu14,His17,Asp21,Pro22,Pro27,Pro34, Asp35,Pro37]-human amylin

Compound 12

$N^1$-[(4S)-4-carboxy-4-(17-carboxyheptadecanoylamino)butanoyl]-[Ala1,Ser2,Leu4,Ala7,Gln8, Glu14,His17,Asp21,Pro22,Pro27,Asp31,Pro34, Asp35,Pro37]-human amylin

Compound 13

$N^1$-[(4S)-4-carboxy-4-(17-carboxyheptadecanoylamino)butanoyl]-[Ala1,Gly2,Ser3,Leu4,Ser5,Ala7, Gln8,Ala10,Glu14,His17,Asp21,Pro25,Pro28,Pro29, Asp31,Pro37]-human amylin

Compound 14

$N^1$-[(4S)-4-carboxy-4-(17-carboxyheptadecanoy-lamino)butanoyl]-[Ala1,Ser2,His3,Leu4,Ser5,Ala7, Gln8,Ala10,Glu14,His17,Asp21,Pro25,Pro28,Pro29, Asp31,Pro37]-human amylin

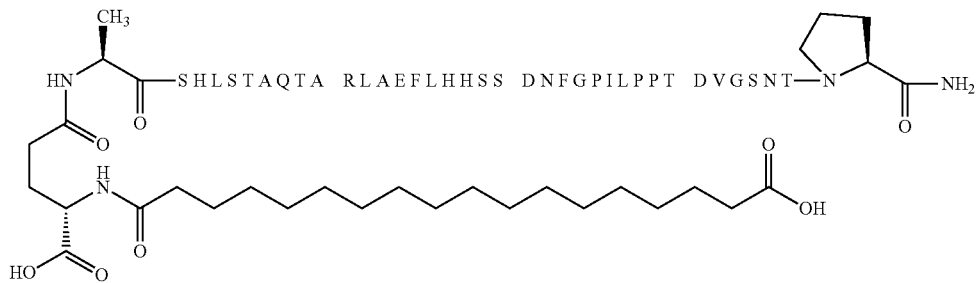

Compound 15

$N^1$-[(4S)-4-carboxy-4-(17-carboxyheptadecanoy-lamino)butanoy]-[Ala1,Gly2,Ser3,Leu4,Ser5,Ala7, Gln8,Ala10,Glu14,His17,Pro25,Pro28,Pro29,Asp31, Glu35,Pro37],des-(19-22)-human amylin

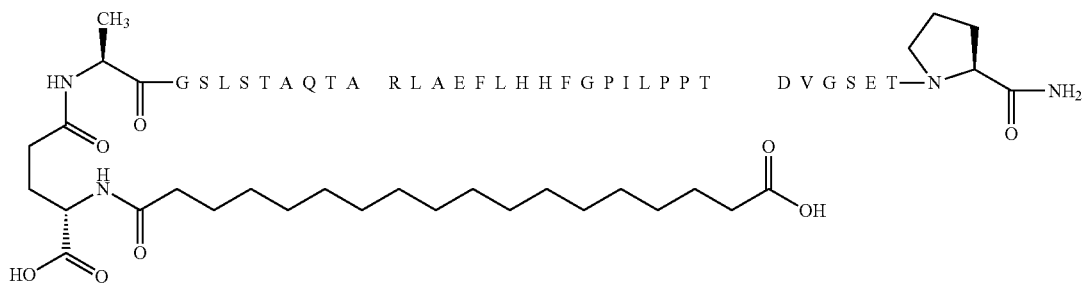

Compound 16

$N^1$-[(4S)-4-carboxy-4-(17-carboxyheptadecanoy-lamino)butanoyl]-[Ala1,Gly2,Glu3,Leu4,Ser5,Ala7, Gln8,Ala10,Glu14,His17,Pro25,Pro28,Pro29,Asp31, Glu35,Pro37],des-(19-22)-human amylin

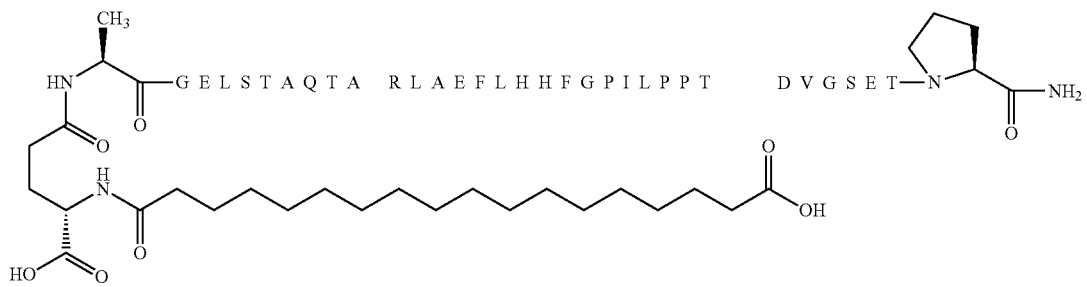

Compound 17

N¹-[(4S)-4-carboxy-4-[[(4S)-4-carboxy-4-(17-carboxyheptadecanoylamino)butanoyl]amino]butanoyl]-[Ala1,Ser2,His3,Leu4,Ser5,Ala7,Gln8,Ala10,Glu14,His17,Pro25,Pro28,Pro29,Asp31,Glu35,Pro37],des-(19-22)-human amylin

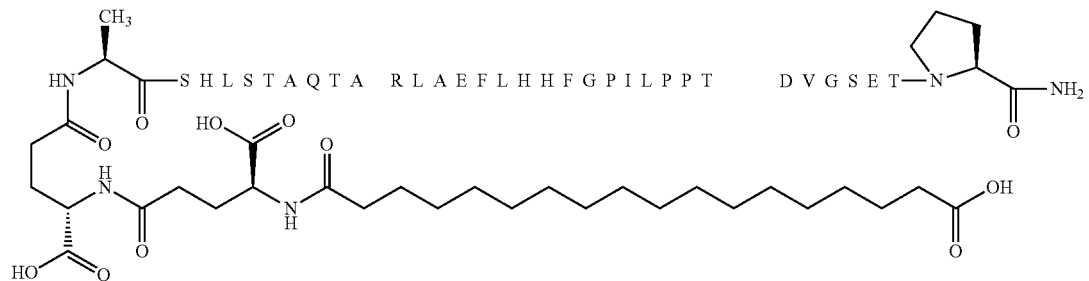

Compound 18

N¹-acetyl,N{Epsilon-25}-[(4S)-4-carboxy-4-(17-carboxyheptadecanoylamino)butanoyl]-[Ala1,Ser2,Gln3,Leu4,Ser5,Ala7,Gln8,Glu14,His17,Asp21,Lys25,Pro28,Pro29,Asp31,Pro37]-human amylin

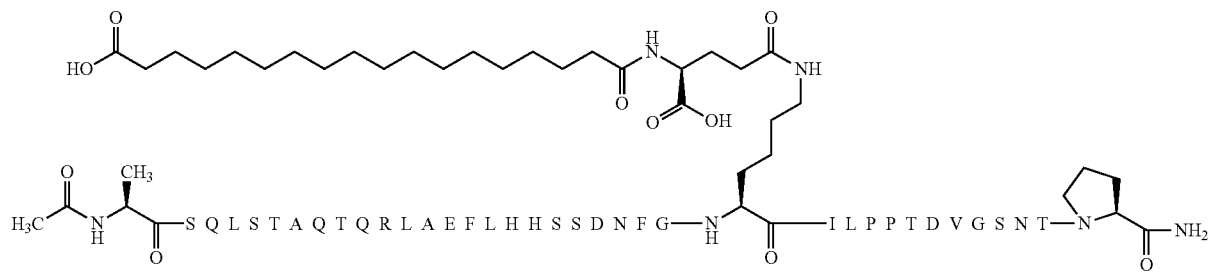

Compound 19

N¹-acetyl,N{Epsilon-25}-[(4S)-4-carboxy-4-(17-carboxyheptadecanoylamino)butanoyl]-[Ala1,Ser2,Gln3,Leu4,Ser5,Ala7,Gln8,Glu14,His17,Asp21,Pro22,Lys25,Pro27,Asp31,Pro34,Asp35,Pro37]-human amylin

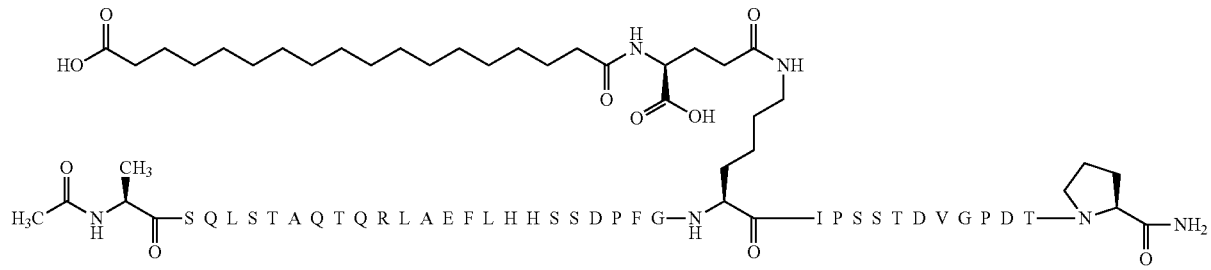

Compound 20

$N^1$-[(4S)-4-carboxy-4-(15-carboxypentadecanoy-
lamino)butanoyl]-[Ala1,Ser2,His3,Leu4,Ser5,Ala7,
Gln8,Ala10,Glu14,His17,Asp21,Pro25,Pro28,Pro29,
Asp31,Pro37]-human amylin

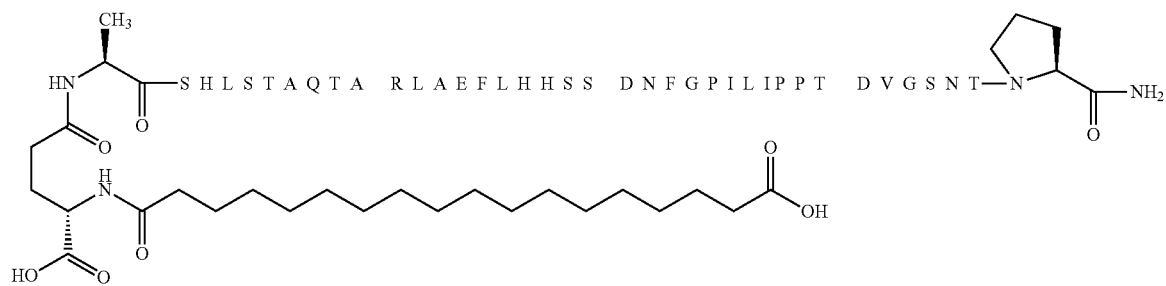

Compound 21

$N^1$-[(4S)-4-carboxy-4-(17-carboxyheptadecanoy-
lamino)butanoyl]-[Ala1,Ser2,His3,Leu4,Ser5,Ala7,
Gln8,Glu14,His17,Asp21,Pro25,Pro28,Pro29,Asp31,
Pro37]-human amylin

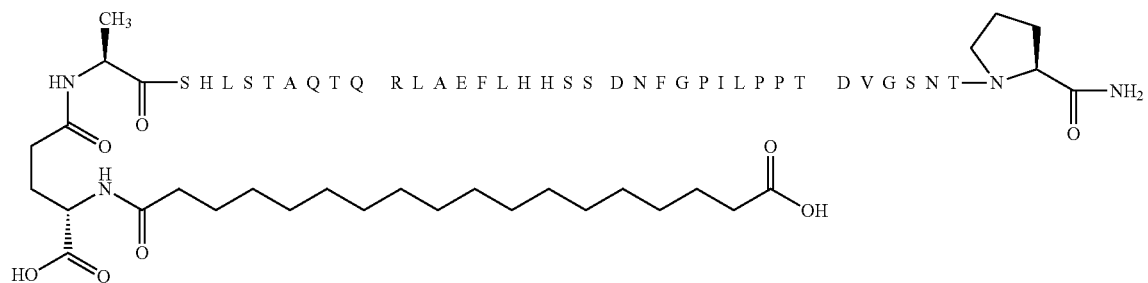

Compound 22

$N^1$-[(4S)-4-carboxy-4-(17-carboxyheptadecanoy-
lamino)butanoyl]-[Ala1,Ser2,Gln3,Leu4,Ser5,Ala7,
Gln8,Ala10,Glu14,His17,Asp21,Pro25,Pro28,Pro29,
Asp31,Pro37]-human amylin

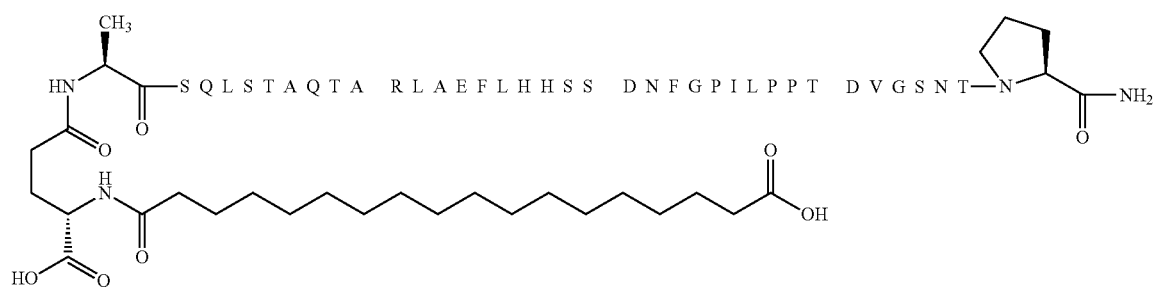

Compound 23

N¹-[(4S)-4-carboxy-4-(17-carboxyheptadecanoy-
lamino)butanoyl]-[Ala1,Ser2,Ala3,Leu4,Ser5,Ala7,
Gln8,Ala10,Glu14,His17,Asp21,Pro25,Pro28,Pro29,
Asp31,Pro37]-human amylin

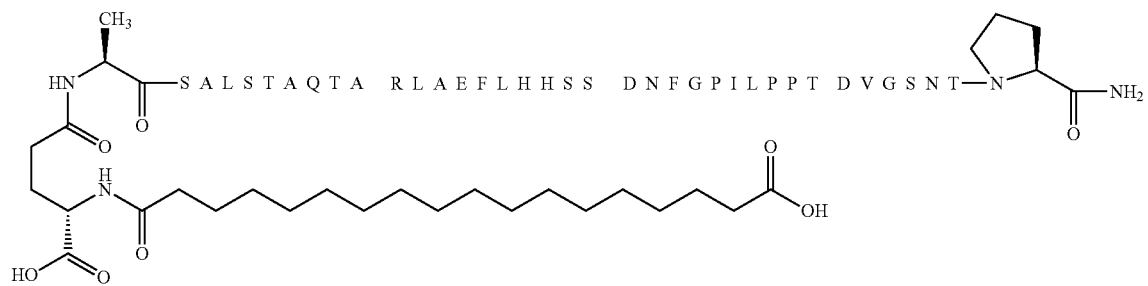

Compound 24

N¹-[(4S)-4-carboxy-4-(17-carboxyheptadecanoy-
lamino)butanoyl]-[Ala1,Ser2,Gln3,Leu4,Ser5,Ala7,
Gln8,Glu14,His17,Asp21,Pro22,Pro27,Asp31,Pro34,
Asp35,Pro37-human amylin

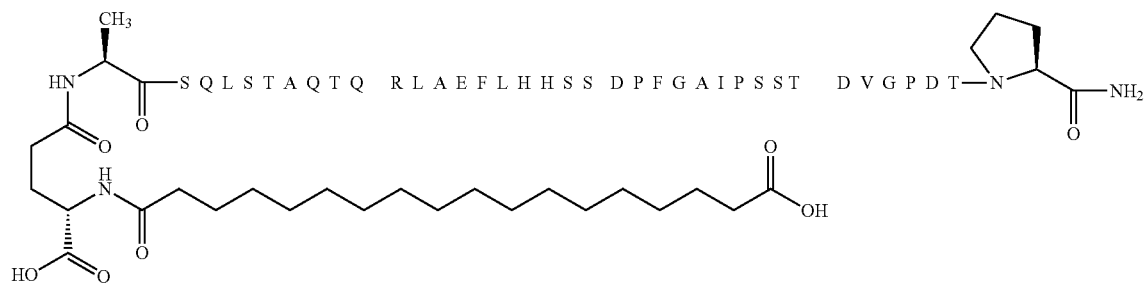

Compound 25

N¹-[(4S)-4-carboxy-4-(17-carboxyheptadecanoy-
lamino)butanoyl]-[Ala1,Ser2,His3,Leu4,Ser5,Ala7,
Gln8,Ala10,Glu14,His17,Asp21,Pro22,Pro27,Asp31,
Pro34,Asp35,Pro37]-human amylin

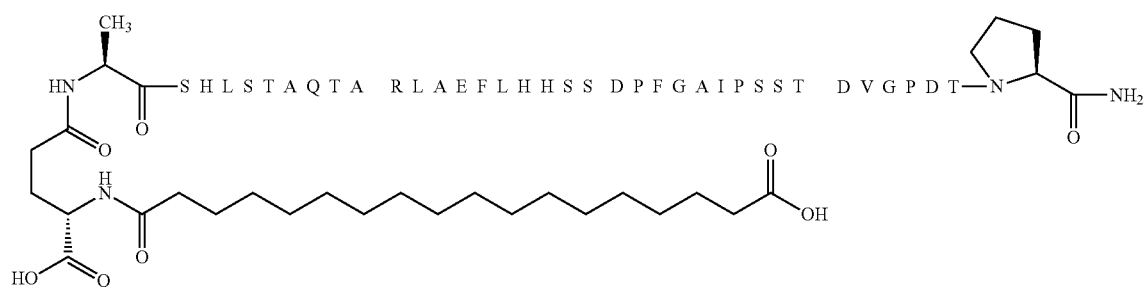

Compound 26

N$^1$-[(4S)-4-carboxy-4-(17-carboxyheptadecanoy-
lamino)butanoyl]-[Ala1,Ser2,His3,Leu4,Ser5,Ala7,
Gln8,Glu14,His17,Asp21,Pro22,Pro27,Asp31,Pro34,
Pro37]-human amylin

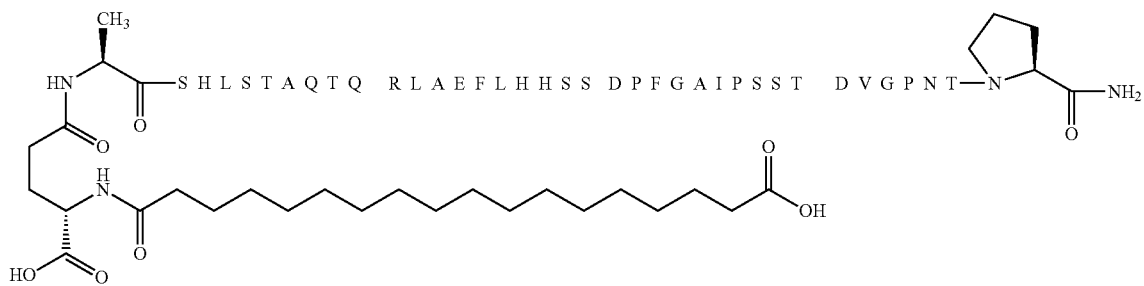

Compound 27

N$^1$-[(4S)-4-carboxy-4-(17-carboxyheptadecanoy-
lamino)butanoyl]-[Ala1,Ser2,His3,Leu4,Ser5,Ala7,
Gln8,Glu14,His17,Glu21,Pro22,Pro27,Glu31,Pro34,
Glu35,Pro37]-human amylin

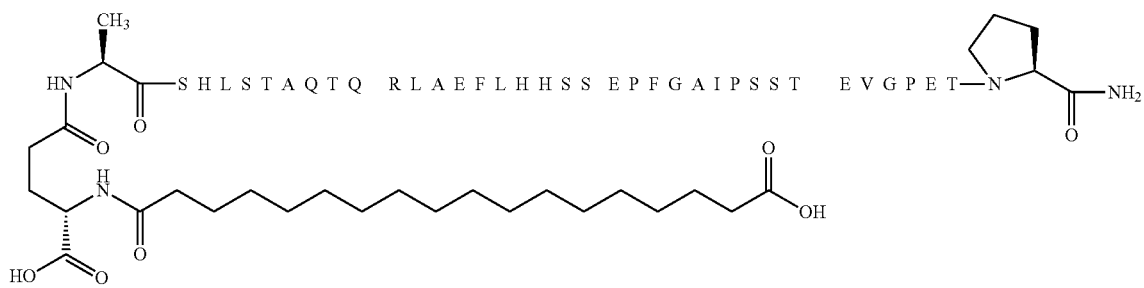

Compound 28

N$^1$-[(4S)-4-carboxy-4-(17-carboxyheptadecanoy-
lamino)butanoyl]-[Ala1,Ser2,His3,Leu4,Ser5,Ala7,
Gln8,Glu14,His17,Pro25,Pro28,Pro29,Asp31,Glu35,
Pro37],des-(19-22)-human amylin

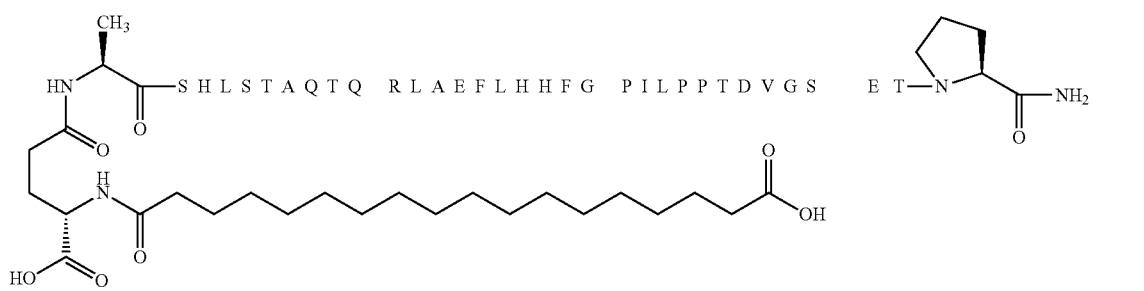

Compound 29

N¹-[(4S)-4-carboxy-4-(17-carboxyheptadecanoy-
lamino)butanoyl]-[Ala1,Ser2,Glu3,Leu4,Ser5,Ala7,
Gln8,Glu14,His17,Pro25,Pro28,Pro29,Asp31,Glu35,
Pro37],des-(19-22)-human amylin

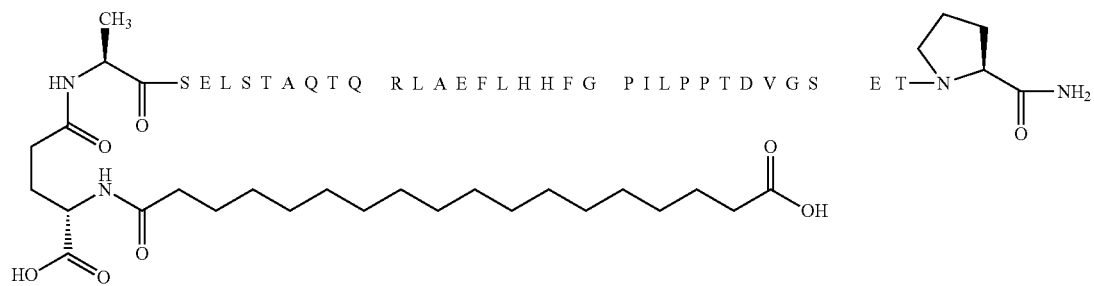

Compound 30

N¹-[(4S)-4-carboxy-4-[[(4S)-4-carboxy-4-(17-car-
boxyheptadecanoylamino)butanoyl]amino]bu-
tanoyl]-[Ala1,Gly2,Ser3,Leu4,Ser5,Ala7,Gln8,
Glu14,His17,Pro25,Pro28,Pro29,Asp31,Glu35,
Pro37],des-(19-22)-human amylin

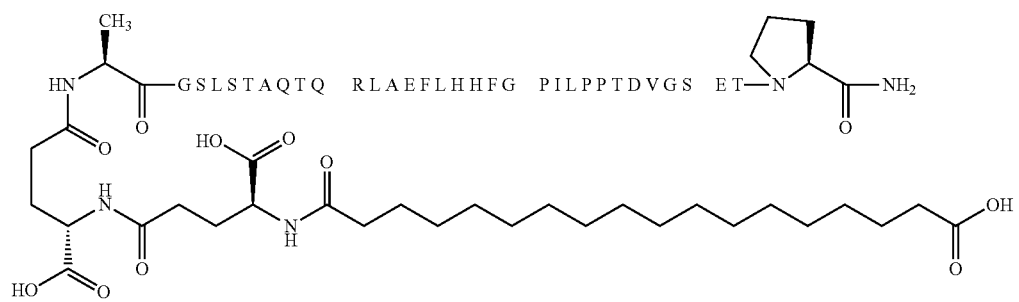

Compound 31

N¹-[(4S)-4-carboxy-4-[[(4S)-4-carboxy-4-(17-car-
boxyheptadecanoylamino)butanoyl]amino]bu-
tanoyl]-[Ala1,Ser2,His3,Leu4,Ser5,Ala7,Gln8,
Glu14,His17,Pro25,Pro28,Pro29,Asp31,Glu35,
Pro37],des-(19-22)-human amylin

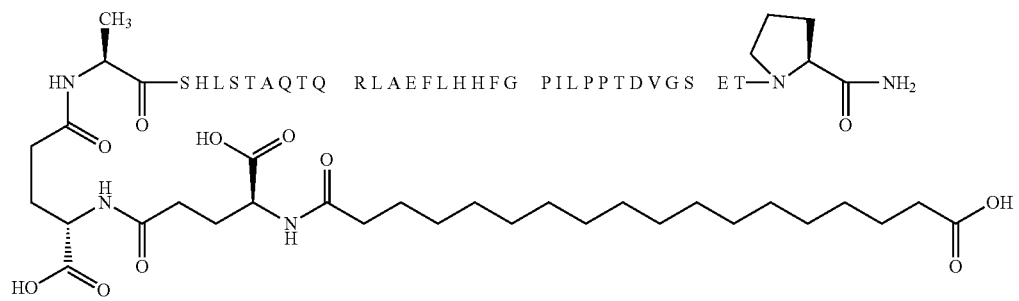

Compound 32

N[1]-[(4S)-4-carboxy-4-[[(4S)-4-carboxy-4-(17-carboxyheptadecanoylamino)butanoyl]amino]butanoyl]-[Ala1,Ser2,His3,Leu4,Ser5,Ala7,Gln8,Glu14,His17,Pro25,Pro28,Pro29,Asp31,Glu35],des-(19-22)-human amylin

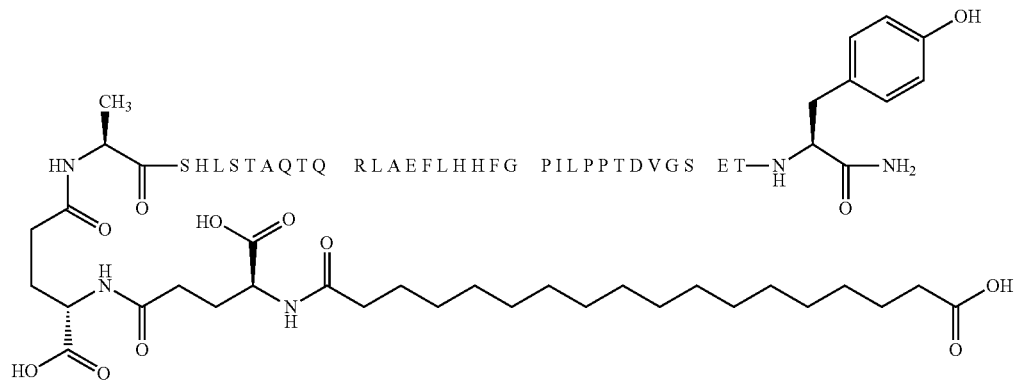

Compound 33

N[1]-[(4S)-4-carboxy-4-(17-carboxyheptadecanoylamino)butanoyl]-[Ala1,Ser2,His3,Leu4,Ser5,Leu7,Gln8,Glu14,His17,Asp21,Pro22,Pro27,Asp31,Pro34,Asp35,Pro37]-human amylin

Compound 34

N[1]-[(4S)-4-carboxy-4-(17-carboxyheptadecanoylamino)butanoyl]-[Ala1,Ser2,His3,Leu4,Ser5,Leu7,Gln8,Glu14,His17,Asp21,Pro25,Pro28,Pro29,Asp31,Pro37]-human amylin

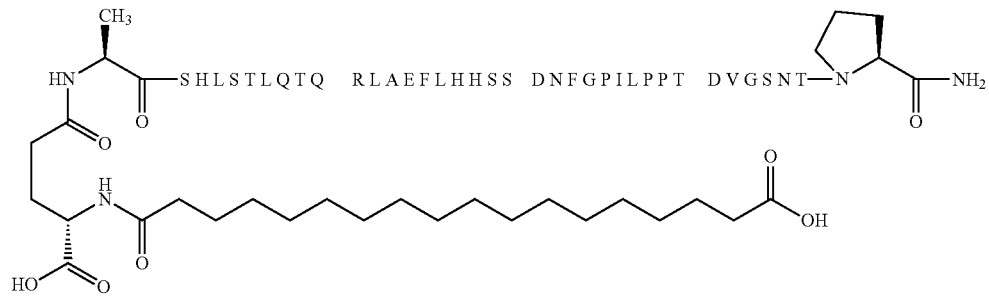

Compound 35

N¹-[(4S)-4-carboxy-4-(17-carboxyheptadecanoy-
lamino)butanoyl]-[Ala1,Ser2,His3,Leu4,Ser5,Leu7,
Gln8,Glu14,His17,Pro25,Pro28,Pro29,Asp31,Glu35,
Pro37],des-(19-22)-human amylin

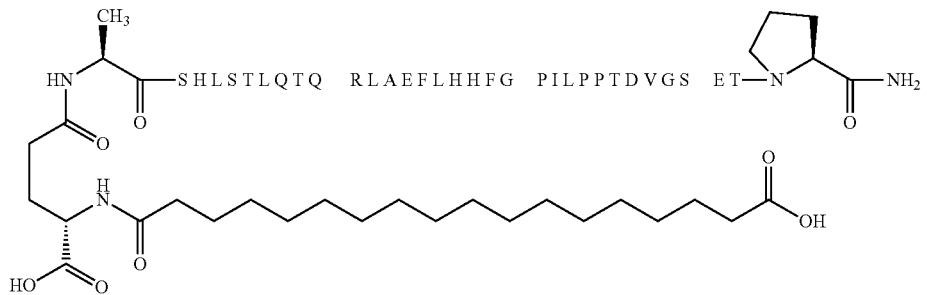

Compound 36

N¹-[(4S)-4-carboxy-4-(17-carboxyheptadecanoy-
lamino)butanoyl]-[Ala1,Ser2,His3,Leu4,Ser5,Ala7,
Gln8,Glu14,His17,Asp21,Pro22,Pro27,Asp31,Pro34,
Asp35]-human amylin

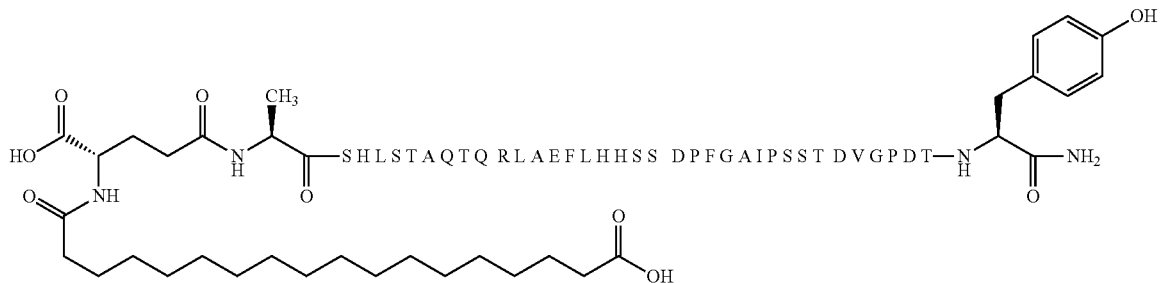

Compound 37

N¹-[(4S)-4-carboxy-4-(17-carboxyheptadecanoy-
lamino)butanoyl]-[Ala1,Ser2,His3,Leu4,Ser5,Ala7,
Gln8,Ala10,Glu14,His17,Asp21,Pro22,Pro27,Asp31,
Pro34,Asp35]-human amylin

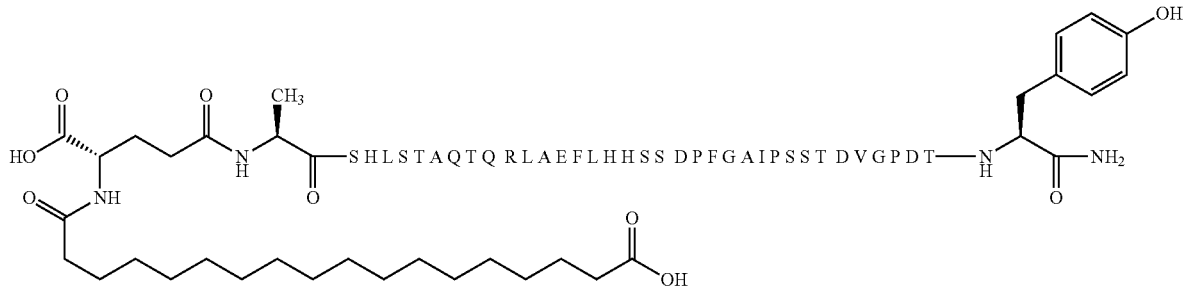

Compound 38

N¹-[(4S)-4-carboxy-4-(17-carboxyheptadecanoy-
lamino)butanoyl]-[Ala1,Ser2,His3,Leu4,Ser5,Ala7,
Gln8,Ala10,Glu14,His17,Asp21,Pro25,Pro28,Pro29,
Asp31]-human amylin

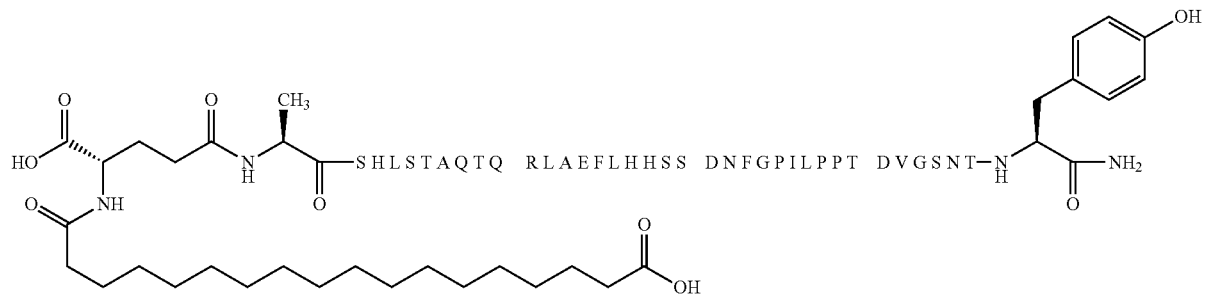

Compound 39

N¹-[(4S)-4-carboxy-4-(19-carboxynonadecanoy-
lamino)butanoyl]-[Ala1,Ser2,His3,Leu4,Ser5,Ala7,
Gln8,Ala10,Glu14,His17,Asp21,Pro22,Pro27,Asp31,
Pro34,Asp35,Pro37]-human amylin

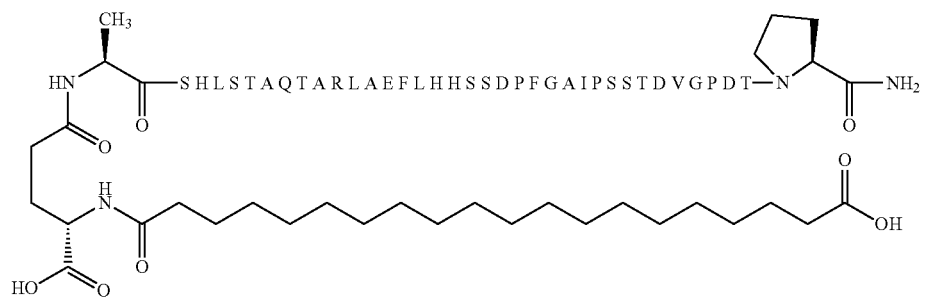

Compound 40

N¹-acetyl,N{Epsilon-25}-[(4S)-4-carboxy-4-(17-
carboxyheptadecanoylamino)butanoyl]-[Ala1,Ser2,
His3,Leu4,Ser5,Ala7,Gln8,Ala10,Glu14,His17,
Asp21,Pro22,Lys25,Pro27,Asp31,Pro34,Asp35,
Pro37]-human amylin

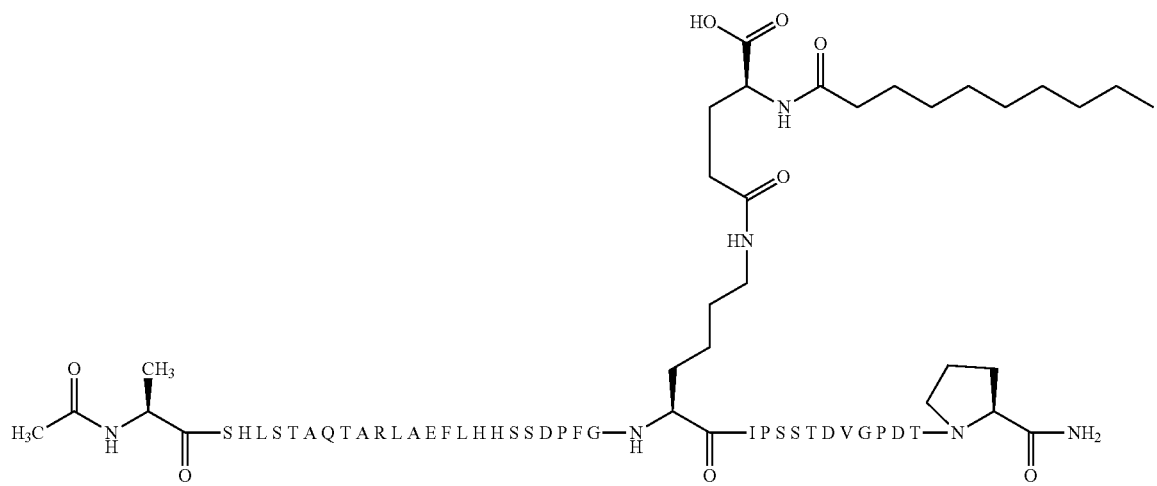

Compound 41

N¹-acetyl,N{Epsilon-25}-[(4S)-4-carboxy-4-(17-carboxyheptadecanoylamino)butanoyl]-[Ala1,Ser2, His3,Leu4,Ser5,Ala7,Gln8,Ala10,Glu14,His17, Asp21,Lys25,Pro28,Pro29,Asp31,Pro37]-human amylin Compound 42

N¹-[(4S)-4-carboxy-4-(17-carboxyheptadecanoylamino)butanoyl]-[Ala1,Ser2,His3,Leu4,Ser5,Ala7, Gln8,Ala10,Glu14,His17,Pro25,Pro28,Pro29,Asp31, Glu35],des-(19-22)-human amylin

Compound 43

N¹-[(4S)-4-carboxy-4-(17-carboxyheptadecanoylamino)butanoyl]-[Ala1,Ser2,His3,Leu4,Ser5,Ala7,Gln8,Ala10,Glu14,His17,Pro25,Pro28,Pro29,Asp31,Glu35,Pro37],des-(19-22)-human amylin

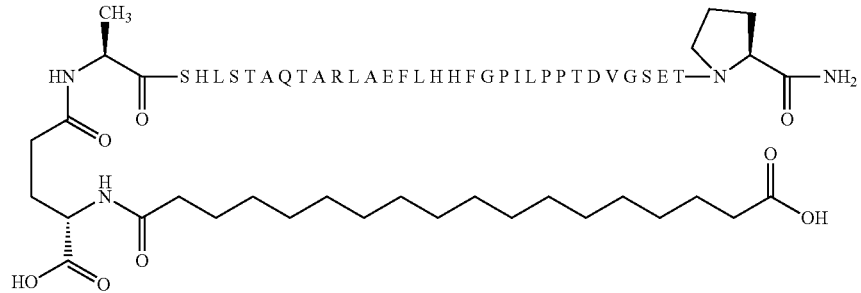

Example 3: LCMS Characterization of the Synthesized Compounds

LCMS analysis was performed on a set up consisting of Waters Acquity UPLC H Class system and Waters Xevo G2-xS QTof. Eluents: A: MQ water; B: MeCN; C: 2% formic acid+0.1% TFA in MQ water.

The analysis was performed at RT (column temp 60° C.) by injecting an appropriate volume of the sample onto the column which was eluted with a gradient of A, B, and 5% C. The UPLC conditions, detector settings, and mass spectrometer settings were: Column: Waters Acquity BEH, C-18, 1.7 μm, 2.1 mm×50 mm. Gradient: Linear 5%-95% B during 4.0 min at 0.4 ml/min. Total run-time: 7.0 min. Detection: MS resolution mode, ionisation method: ES. Scan: 50-5000 amu.

The monoisotopic mass was recorded for the examples and the found and calculated values are depicted in Table 1.

TABLE 1

Measured and calculated MS species for examples

| | Species | m/z found | m/z calc |
|---|---|---|---|
| Compound 1 | [M + 4H]4+ | 1106.074 | 1106.074 |
| | [M + 3H]3+ | 1474.435 | 1474.430 |
| Compound 2 | [M + 4H]4+ | 1085.319 | 1085.316 |
| | [M + 3H]3+ | 1446.749 | 1446.752 |
| Compound 3 | [M + 4H]4+ | 1099.577 | 1099.571 |
| | [M + 3H]3+ | 1465.757 | 1465.759 |
| Compound 4 | [M + 4H]4+ | 1002.537 | 1002.537 |
| | [M + 3H]3+ | 1336.383 | 1336.381 |
| Compound 5 | [M + 4H]4+ | 988.283 | 988.282 |
| | [M + 3H]3+ | 1317.374 | 1317.374 |
| Compound 6 | [M + 4H]4+ | 1082.556 | 1082.553 |
| | [M + 3H]3+ | 1443.077 | 1443.068 |
| Compound 7 | [M + 4H]4+ | 1075.055 | 1075.050 |
| | [M + 3H]3+ | 1433.066 | 1433.064 |
| Compound 8 | [M + 4H]4+ | 1075.552 | 1075.545 |
| | [M + 3H]3+ | 1433.733 | 1433.724 |
| Compound 9 | [M + 4H]4+ | 1107.817 | 1107.805 |
| | [M + 3H]3+ | 1476.746 | 1476.738 |
| Compound 10 | [M + 4H]4+ | 1055.538 | 1055.535 |
| | [M + 3H]3+ | 1407.047 | 1407.045 |
| Compound 11 | [M + 4H]4+ | 1066.042 | 1066.038 |
| | [M + 3H]3+ | 1421.053 | 1421.048 |
| Compound 12 | [M + 4H]4+ | 1065.789 | 1065.792 |
| | [M + 3H]3+ | 1420.729 | 1420.720 |

TABLE 1-continued

Measured and calculated MS species for examples

| | Species | m/z found | m/z calc |
|---|---|---|---|
| Compound 13 | [M + 4H]4+ | 1058.306 | 1058.298 |
| | [M + 3H]3+ | 1410.734 | 1410.729 |
| Compound 14 | [M + 4H]4+ | 1078.305 | 1078.308 |
| | [M + 3H]3+ | 1437.408 | 1437.408 |
| Compound 15 | [M + 4H]4+ | 961.269 | 961.265 |
| | [M + 3H]3+ | 1281.361 | 1281.351 |
| Compound 16 | [M + 4H]4+ | 971.767 | 971.768 |
| | [M + 3H]3+ | 1295.362 | 1295.354 |
| Compound 17 | [M + 4H]4+ | 1013.545 | 1013.535 |
| | [M + 3H]3+ | 1351.041 | 1351.044 |
| Compound 18 | [M + 4H]4+ | 1108.580 | 1108.576 |
| | [M + 3H]3+ | 1477.769 | 1477.766 |
| Compound 19 | [M + 4H]4+ | 1098.071 | 1098.062 |
| | [M + 3H]3+ | 1463.752 | 1463.747 |
| Compound 20 | [M + 4H]4+ | 1071.301 | 1071.300 |
| | [M + 3H]3+ | 1428.066 | 1428.064 |
| Compound 21 | [M + 4H]4+ | 1092.558 | 1092.563 |
| | [M + 3H]3+ | 1456.417 | 1456.415 |
| Compound 22 | [M + 4H]4+ | 1076.062 | 1076.058 |
| | [M + 3H]3+ | 1434.415 | 1434.408 |
| Compound 23 | [M + 4H]4+ | 1061.810 | 1061.802 |
| | [M + 3H]3+ | 1415.411 | 1415.401 |
| Compound 24 | [M + 4H]4+ | 1073.298 | 1073.295 |
| | [M + 3H]3+ | 1430.728 | 1430.724 |
| Compound 25 | [M + 4H]4+ | 1061.290 | 1061.289 |
| | [M + 3H]3+ | 1414.719 | 1414.717 |
| Compound 26 | [M + 4H]4+ | 1075.310 | 1075.299 |
| | [M + 3H]3+ | 1433.407 | 1433.396 |
| Compound 27 | [M + 4H]4+ | 1086.060 | 1086.056 |
| | [M + 3H]3+ | 1447.746 | 1447.740 |
| Compound 28 | [M + 4H]4+ | 995.527 | 995.530 |
| | [M + 3H]3+ | 1327.033 | 1327.037 |
| Compound 29 | [M + 4H]4+ | 993.526 | 993.526 |
| | [M + 3H]3+ | 1324.365 | 1324.365 |
| Compound 30 | [M + 4H]4+ | 1007.781 | 1007.781 |
| | [M + 3H]3+ | 1343.379 | 1343.372 |
| Compound 31 | [M + 4H]4+ | 1027.785 | 1027.790 |
| | [M + 3H]3+ | 1370.048 | 1370.051 |
| Compound 32 | [M + 4H]4+ | 1044.305 | 1044.293 |
| | [M + 3H]3+ | 1392.057 | 1392.055 |
| Compound 33 | [M + 4H]4+ | 1086.060 | 1086.056 |
| | [M + 3H]3+ | 1447.746 | 1447.740 |
| Compound 34 | [M + 4H]4+ | 1103.081 | 1103.075 |
| | [M + 3H]3+ | 1470.430 | 1470.431 |
| Compound 35 | [M + 4H]4+ | 1006.041 | 1006.041 |
| | [M + 3H]3+ | 1341.055 | 1341.053 |
| Compound 36 | [M + 4H]4+ | 1092.057 | 1092.047 |
| | [M + 3H]3+ | 1455.730 | 1455.727 |

TABLE 1-continued

Measured and calculated MS species for examples

| | Species | m/z found | m/z calc |
|---|---|---|---|
| Compound 37 | [M + 4H]4+ | 1077.794 | 1077.792 |
| | [M + 3H]3+ | 1436.725 | 1436.720 |
| Compound 38 | [M + 4H]4+ | 1094.805 | 1094.810 |
| | [M + 3H]3+ | 1459.418 | 1459.412 |
| Compound 39 | [M + 4H]4+ | 1068.302 | 1068.297 |
| | [M + 3H]3+ | 1424.063 | 1424.060 |
| Compound 40 | [M + 4H]4+ | 1086.060 | 1086.056 |
| | [M + 3H]3+ | 1447.746 | 1447.740 |
| Compound 41 | [M + 4H]4+ | 1096.566 | 1096.571 |
| | [M + 3H]3+ | 1461.764 | 1461.759 |
| Compound 42 | [M + 4H]4+ | 997.775 | 997.777 |
| | [M + 3H]3+ | 1330.031 | 1330.033 |
| Compound 43 | [M + 4H]4+ | 981.283 | 981.274 |
| | [M + 3H]3+ | 1308.032 | 1308.030 |

Example 4: Human Amylin- and Calcitonin Receptor In Vitro Potency Assay

Amylin Receptor Assay

To determine the ability of compounds to activate or agonize the amylin receptor, in vitro potency assays on cells expressing the human amylin receptor (hAMYR3) can be performed as described below.

Assay Principle

Activation of hAMYR3 leads to increased cellular concentrations of cAMP. Consequently, transcription is activated by promotors containing multiple copies of the CAMP response element (CRE). It is thus possible to measure hAMYR3 activity using a CRE-luciferase reporter gene introduced into Baby Hamster Kidney (BHK) cells co-expressing the hAMYR3.

Cells and Assay Reagents

A BHK cell line was stably transfected with the human calcitonin receptor (a) and a CRE-responsive luciferase (CRE-Luc) reporter gene according to methods known to the person skilled in the art (Hollex-1 cell line, obtained from Zymogenetics described in U.S. Pat. No. 5,622,839). The cell line was further transfected with human receptor modifying protein 3 (RAMP3) using standard methods. This turns the human calcitonin receptor into a human amylin-3(a) receptor.

Cells stocks were prepared by culturing of the stably transfected BHK hAMYR3/CRE-Luc cell line in growth medium consisting of DMEM (Gibco, 31966-021) supplemented with 10% FBS (Gibco, 16140-071), 1% Pen/Strep (Gibco, 15140-122), 0.5 mg/mL Geneticin (Gibco, 10131-027), 0.4 mg/mL Hygromycin (Invitrogen, 10687010) and 250 nM Methotrexate (Sigma, A6770). Cells at approximately 80-90% confluence were washed once with PBS (Gibco 14190-094) and loosened from the cell flasks with Versene (Gibco, 15040-033) or TrypLE™ (Gibco, 12605-010). After centrifugation, the cell pellet was dissolved and diluted to approximately 2.5×10E6 cells/mL in Recovery™ Cell Culture Freezing Medium (Gibco, 12648-010). Cells were aliquoted and stored at −180° C. until use.

The assay buffer consisted of DMEM without phenol red (Gibco, 11880-028) supplemented with 1× GlutaMAX (Gibco, 35050-038), 10 mM HEPES (Gibco, 15630-056) and 1% (w/v) ovalbumin (Sigma, A5503).

Procedure

To perform the assay, BHK hAMYR3/CRE-Luc cells were thawed, washed once in PBS and seeded in 40 µL growth medium in a white 384-well culture plate (PerkinElmer, 6007688) at a cell density of 4.000 cells/well on the day before the experiment. The plate was incubated over night at 37° C. in 5% $CO_2$. On the day of the assay, cells were washed once in assay buffer. Serial dilutions (7-fold dilutions, 7 concentrations Pr. compound and one well containing only assay buffer) of comparator compounds and amylin analogues were performed in assay buffer often starting from approximately 10 nM in 96-well plates and 30 µL of each concentration added to the 384-well assay plate with cells. The assay plate was incubated for 3 hours at 37° C. in 5% $CO_2$ after which 30 µL SteadyLite Plus (PerkinElmer, 6066759) was added to each well. The assay plate was sealed, incubated at room temperature with gentle shaking for 5 minutes followed by 30 minutes incubation without shaking while protected from light. Luminescence was detected on a luminescence plate reader e.g. a Synergy 2 (BioTek). The $EC_{50}$ values [pM] were calculated by non-linear curve fitting applying a four-parameter logistic model (Hill slope=1.5, shared bottom response within each plate) using GraphPad Prism or by means of TIBCO Enterprise Runtime for R (TIBCO Software, Palo Alto, CA, USA).

Calcitonin Receptor Assay

To determine the ability of compounds to activate or agonize the calcitonin receptor, in vitro potency assays on cells expressing the human calcitonin receptor (hCTR) can be performed as described below.

Assay Principle

Activation of hCTR leads to increased cellular concentrations of CAMP. Consequently, transcription is activated by promotors containing multiple copies of the CAMP response element (CRE). It is thus possible to measure hCTR activity using a CRE-luciferase reporter gene introduced into Baby Hamster Kidney (BHK) cells co-expressing the hCTR.

Cells and Assay Reagents

A BHK cell line was stably transfected with the human calcitonin receptor (a) and a CRE-responsive luciferase (CRE-Luc) reporter gene according to methods known to the person skilled in the art (Hollex-1 cell line, obtained from Zymogenetics described in U.S. Pat. No. 5,622,839).

Cells stocks were prepared by culturing of the stably transfected BHK hCTR/CRE-Luc cell line in growth medium consisting of DMEM (Gibco, 31966-021) supplemented with 10% FBS (Gibco, 16140-071), 1% Pen/Strep (Gibco, 15140-122), 0.5 mg/mL Geneticin (Gibco, 10131-027) and 250 nM Methotrexate (Sigma, A6770). Cells at approximately 80-90% confluence were washed once with PBS (Gibco 14190-094) and loosened from the cell flasks with Versene (Gibco, 15040-033) or TrypLE™ (Gibco, 12605-010). After centrifugation, the cell pellet was dissolved and diluted to approximately 2.5×10E6 cells/mL in Recovery™ Cell Culture Freezing Medium (Gibco, 12648-010). Cells were aliquoted and stored at −180° C. until use.

The assay buffer consisted of DMEM without phenol red (Gibco, 11880-028) supplemented with 1× GlutaMAX (Gibco, 35050-038), 10 mM HEPES (Gibco, 15630-056) and 1% (w/v) ovalbumin (Sigma, A5503).

Procedure

To perform the assay, BHK hCTR/CRE-Luc cells were thawed, washed once in PBS and seeded in 40 µL growth medium in a white 384-well culture plate (PerkinElmer, 6007688) at a cell density of 4.000 cells/well on the day before the experiment. The plate was incubated over night at 37° C. in 5% $CO_2$. On the day of the assay, cells were washed once in assay buffer. Serial dilutions (7-fold dilutions, 7 concentrations Pr. compound and one well containing only assay buffer) of comparator compounds and amylin analogues were performed in assay buffer often starting from approximately 10 nM in 96-well plates and 30 µL of each concentration added to the 384-well assay plate with cells. The assay plate was incubated for 3 hours at 37° C. in 5% $CO_2$ after which 30 µL SteadyLite Plus (PerkinElmer, 6066759) was added to each well. The assay plate was sealed, incubated at room temperature with gentle shaking for 5 minutes followed by 30 minutes incubation without shaking while protected from light. Luminescence was detected on a luminescence plate reader e.g. a Synergy 2 (BioTek). The $EC_{50}$ values [pM] were calculated by non-linear curve fitting applying a four-parameter logistic model (Hill slope=1.5, shared bottom response within each plate) using GraphPad Prism or by means of TIBCO Enterprise Runtime for R (TIBCO Software, Palo Alto, CA, USA).

TABLE 2

In vitro human AmyR3 and human CalcR potency of amylin analogues

| Compound number | hAmyR3 potency, EC50 (pM) | hCalcR potency, EC50 (pM) |
| --- | --- | --- |
| Compound 2 | 0.77 | 1.31 |
| Compound 3 | 0.90 | 1.30 |
| Compound 4 | 1.12 | 1.44 |
| Compound 5 | 1.09 | 1.49 |
| Compound 6 | 0.86 | 1.25 |
| Compound 7 | 1.68 | 1.81 |
| Compound 8 | 1.50 | 1.44 |
| Compound 9 | 2.18 | 1.68 |
| Compound 10 | 1.44 | 1.49 |
| Compound 11 | 2.43 | 1.58 |
| Compound 12 | 1.88 | 1.99 |
| Compound 13 | 1.36 | 1.58 |
| Compound 14 | 1.28 | 1.63 |
| Compound 15 | 0.81 | 1.01 |
| Compound 16 | 1.25 | 1.03 |
| Compound 17 | 1.11 | 1.15 |
| Compound 18 | 1.38 | 1.19 |
| Compound 19 | 1.50 | 1.00 |
| Compound 20 | 1.62 | 1.50 |
| Compound 21 | 1.64 | 1.89 |
| Compound 22 | 1.22 | 1.86 |
| Compound 23 | 1.62 | 1.58 |
| Compound 24 | 1.49 | 1.56 |
| Compound 25 | 1.27 | 1.50 |
| Compound 26 | 1.31 | 2.19 |
| Compound 27 | 2.68 | 1.78 |
| Compound 28 | 2.06 | 1.72 |
| Compound 29 | 5.20 | 3.08 |
| Compound 30 | 2.37 | 2.07 |
| Compound 31 | 2.03 | 2.13 |
| Compound 32 | 5.71 | 15.70 |
| Compound 33 | 1.69 | 1.74 |
| Compound 34 | 1.91 | 2.06 |
| Compound 35 | 1.60 | 2.26 |
| Compound 36 | 2.96 | 3.22 |
| Compound 37 | 1.68 | 2.16 |
| Compound 38 | 1.97 | 3.15 |
| Compound 39 | 1.05 | 1.41 |
| Compound 40 | 1.38 | 1.29 |
| Compound 41 | 1.16 | 1.16 |
| Compound 42 | 2.11 | 2.78 |
| Compound 43 | 1.06 | 1.76 |

TABLE 3

In vitro human AmyR3 and human CalcR potency of amylin comparators

| Compound | Comparator special features | hAmyR3 potency, EC50 (pM) | hCalcR potency, EC50 (pM) |
| --- | --- | --- | --- |
| cagrilintide | Amylin receptor agonist (RA) in development | 1.58 | 2.53 |

The data in Table 2 show that all the tested compounds agonize both the human AmyR3 and CalcR and the most compounds agonize the two receptors with $EC_{50}$ values comparable to cagrilintide (Table 3).

The compounds listed in Table 2 are all compounds according to the invention.

Example 5: Oral Pharmacokinetic Profiles in Beagle Dogs

Preparation of Tablets for Pharmacokinetic Studies in Beagles

To be able to evaluate oral exposure following tablet dosing, tablet compositions comprising the test substance and SNAC (sodium N-(8-(2-hydroxybenzoyl)amino)caprylate) were prepared by mixing test substance with roller compacted SNAC and magnesium stearate as, e.g., described in WO 2019/149880.

Methods for Measuring Oral PK Profiles in Beagle Dogs

This assay was performed to measure the oral bioavailability of a compound. The assay determined the exposure of test compound following oral administration in Beagle dogs as described by relevant pharmacokinetic parameters and plasma concentration curves.

Preparation of tablets for oral administration: tablets containing test compound used for the assay described herein were immediate release SNAC-based tablets. The test compound was spray-dried as neutral sodium salt (pH 7-8). Dry granulation was carried out by roller compaction on a Gerteis MINI-PACTOR. Tablets containing 3 mg test compound, 300 mg sodium N-(8-(2-hydroxybenzoyl)amino) caprylate (SNAC) and 7.7 mg magnesium stearate were produced on at Kilian Style One using 7.2×12 mm punches.

Determination of the absorption following oral administration: eight (8) male Beagle dogs, 1 to 8 years of age and weighing approximately 10-15 kg at the start of the studies, were used. The dogs were group-housed in pens (12 hours light:12 hours dark), and fed individually and restrictedly once daily with Royal Canin Medium Adult dog (Royal Canin Products, China Branch, or Brogaarden A/S, Denmark). Exercise and group social were permitted daily, whenever possible. The dogs were used for repeated pharmacokinetic studies with a suitable wash-out period between successive dosing. An appropriate acclimatisation period was given prior to initiation of the first pharmacokinetic study. All handling, dosing and blood sampling of the animals were performed by trained and skilled staff. Before the studies the dogs were fasted overnight and from 0 to 4 h after dosing. Besides, the dogs were restricted to water 1 hour before dosing until 4 hours after dosing, but otherwise had ad libitum access to water during the whole period.

Tablets containing the test compound were administered in the following manner: 10 min prior to tablet administration the dogs were dosed subcutaneously with approximately 3.2 nmol/kg of glucagon. The tablets were placed in the back of the mouth of the dog to prevent chewing. The mouth was then closed, and 10 mL of tap water was given by a syringe to facilitate swallowing of the tablet. Blood was sampled at predefined time points for up till 288 hours after dosing to adequately cover the full plasma concentration-time absorption profile of the compound. For each blood sampling time point approximately 1.2 mL of whole blood was collected in a 1.5 mL EDTA coated tube, and the tube was gently turned to allowing mixing of the sample with the EDTA. Then, the blood samples were kept on ice until centrifugation (4 min, 4° C., 4000 rpm). Plasma was pipetted into Micronic tubes on dry ice and kept at −20° C. until analysis. Blood samples were taken as appropriate, for example from a venflon in the cephalic vein in the front leg for the first 2 hours and then with syringe from the jugular vein for the rest of the time points (the first few drops were allowed to drain from the venflon to avoid heparin saline from the venflon in the sample).

Bioanalysis was carried out as follows: plasma concentrations of test compound were assayed by plasma protein precipitation and analysed by liquid chromatography-mass spectrometry (LC-MS). Calibrators were prepared by spiking blank dog plasma with analytes to reach the final concentrations in the range typically from 0.5 to 200 nM. Calibrators, plasma blanks or study samples were prepared for LC-MS by protein precipitation by adding 3 volumes of ethanol followed by centrifugation at 4000 rpm at 4° C. for 1 h. The supernatant was diluted with 2 volumes of Milli-Q water containing 0.1% formic acid before injection on the LC-MS system. The system used was a Transcend II Interface Module SRD3200 system from Thermo Scientific (Waltham, MA, USA) coupled to a Orbitrap Exploris 240 mass spectrometer from Thermo Scientific. The LC was equipped with a TurboFlow Cyclone Column 0.5×50 mm (CH-953288, Thermo Scientific) as the first dimensional trapping column and Poroshell 120 SB-C18 2.7 µm as the analytical column (2.1×50 mm from Agilent, Santa Clara, CA, USA). The mobile phase composition of the loading pump is as below: mobile phase A consists of 95% milli-Q water, 2.5% acetonitrile, 2.5% methanol and 0.1% formic acid; mobile phase B consists of 47.5% acetonitrile, 47.5% methanol, 5% milli-Q water, and 0.1% formic acid. The analyte of interest was loaded from the Turbo flow column at 30% B to the second dimensional analytical column. A gradient elution was conducted at the elution pump using mobile phase A (95% milli-Q water, 2.5% acetonitrile, 2.5% methanol and 0.1% formic acid) and mobile phase B (47.5% acetonitrile, 47.5% methanol, 5% milli-Q water, and 0.1% formic acid) with a ramping gradient of 0% mobile phase B to 60% mobile phase B in 0.25 minute and from 60% mobile phase B to 80% mobile phase B in 1.17 min, and then from 80% mobile phase B to 100% mobile phase B in 1.17 min. The Orbitrap Exploris 240 was operating in positive ionization mode with the parallel reaction monitoring (PRM) scan mode. Linear calibration curves (weighting 1/x2) were used for calculating the test compound concentrations in the plasma samples to determine maximal plasma concentration (Cmax). Quality control samples for analytes were included. The deviation between nominal and calculated concentration in the calibrators and quality control samples were below 15% and the LLOQ sample was below 20%. The plasma concentration (vs time) profile of the test compound was evaluated and standard pharmacokinetic parameters were estimated by non-compartmental analysis (NCA) using WinNonlin Phoenix 64 (version 8.3.3, CERTARA). Results were reported as dose-corrected maximum plasma concentration (Cmax/Dose), dose-corrected area under curve (AUC/Dose) and half-life (T½).

AUC from time of dosing extrapolated to infinity, based on the last observed concentration (_obs) or last predicted concentration (_pred). "Linear up Log down" option was chosen.

$$AUCINF = AUClast + \frac{Clast}{Lambda\_z}; \quad AUC/D = \frac{AUCINF}{Dose}$$

(if AUC_% Extrap>20%, use AUClast/D)

$$AUC\_\% \, Extrap = \frac{AUCINF - AUClast}{AUCINF} \cdot 100$$

Using WinNonlin NCA analysis, first-order rate constant (Lambda-Z) was estimated by linear regression of time vs. log concentration. First-order rate constant associated with the terminal (log-linear) portion of the curve. The software calculated the value of Lambda-Z and provided half-life (T½) by the formula as below:

$$\text{Terminal half-life} = \ln(2)/\lambda_2$$

TABLE 4

Pharmacokinetic parameters following oral administration in Beagle dogs

| Compound number | Cmax/D [kg/L] | AUC/D [kg*hr/L] | T½ [hours] |
|---|---|---|---|
| Compound 2 | 0.15 | 14.06 | 145.81 |
| Compound 4 | 0.23 | 21.24 | 129.71 |
| Compound 8 | 0.24 | 17.52 | 121.2 |
| Compound 10 | 0.34 | 27.73 | 131.38 |
| Compound 14 | 0.34 | 20.76 | 112.99 |
| Compound 15 | 0.29 | 21.07 | 85.92 |
| Compound 16 | 0.48 | 35.59 | 95.85 |
| Compound 17 | 0.28 | 19.7 | 94.82 |
| Compound 22 | 0.35 | 24.43 | 96.56 |
| Compound 24 | 0.36 | 31.21 | 120.49 |
| Compound 25 | 0.34 | 24.15 | 152.46 |

TABLE 5

Pharmacokinetic parameters following oral administration in Beagle dogs of comparator compound

| Compound number | Special feature | Cmax/D [kg/L] |
|---|---|---|
| Compound 1 | Cagrilintide analogue [Gln31]-Cagrilintide | 0.057 |

All of the compounds in Table 4 showed plasma exposure following oral dosing to Beagle dogs in SNAC (sodium N-(8-(2-hydroxybenzoyl)amino)caprylate) tablets containing magnesium stearate.

The compounds in Table 4 showed improved exposure level compared to the close cagrilintide analogue compound 1 (Table 5). In addition, the compounds in Table 4 exhibit a long T½ following oral administration.

The compounds listed in Table 4 are all compounds according to the invention.

Example 6: Food Intake Studies in the Rat Model

Preparation of Formulations for sc Dosing to Rats

Lyophilised compound was dissolved in vehicle, 8 mM phosphate, 250 mM glycerol, 0.007% polysorbate 20, and pH was adjusted to 7.4 with 1N NaOH.

The final formulation was sterile filtrated and filled into penfill cartridges for dosing.

Experimental Protocol for Efficacy Testing on Appetite Using an Ad Libitum Fed Rat Model Normal weight Sprague Dawley (SD) rats from Taconic Europe, Denmark, were used for the acute food intake studies. The purpose of these studies was to test in vivo effect on food intake and to provide an indication of the compounds' duration of action. Experiments were conducted with permission from the Danish Animal Experiments Inspectorate and were performed in accordance with the guidelines of the Danish legislation governing animal experimentation (1987) as well as the National Institutes of Health (publication number 85-23) and the European Convention for the Protection of Vertebrate Animals used for Experimental and other Scientific Purposes (Council of Europe No 123, Strasbourg 1985).

Prior to study start, rats were acclimatized to the experimental settings for 14 days. During this period, the animals were handled at least 2 times. Immediately upon arrival, rats were put on a reversed light cycle (dark from 10 am-10 pm or 11 am-11 pm) and were transferred into one of three following food intake measuring systems: FeedWin, BioDaq or HM2. Rats were single housed in the FeedWin and BioDaq system and were housed three a cage in the HM2 system (rats were in this case ID-chipped). During the acclimatization period, in which the rats get used to the new light cycle and diet, the animals had free access to food and water. Since rats are nocturnal animals (e.g. most active and consume the majority of calories during the dark period), they were dosed in the morning immediately before onset of dark to prevent interference with their natural feeding pattern and thereby minimize data variation and improve sensitivity. Each amylin analogue was tested in a group of 5-6 rats. A vehicle group of 5-6 rats was included in each experiment and were used as reference point. In case of studies in the HM2 system, rats in same cage received different treatments to eliminate interference of potential technical variations between cages. At start of treatment, rats were dosed once (subcutaneously) based on body weight with a protracted amylin analogue, receiving a dose of 3 nmol/kg. The time of dosing was recorded for each rat.

After dosing, rats were returned to their home cages, where they had access to food and water. Food consumption was recorded individually and continuously by on-line registration for up to 72 h post dosing. At the end of the experiment, body weight was measured again, and animals were euthanized by $CO_2$ overdose.

Data from the food intake studies in rats are shown in Table 6.

TABLE 6

Acute food intake in rat after a single s.c. administration of new amylin analogues (3 nmol/kg). A negative value indicates reduced food intake relative to vehicle whereas a positive value indicates increased food intake relative to vehicle.

| Compound number | Food intake relative to vehicle (%) 0-24 hr, 3 nmol/kg | Food intake relative to vehicle (%) 24-48 hr, 3 nmol/kg | Food intake relative to vehicle (%) 48-72 hr, 3 nmol/kg |
|---|---|---|---|
| Compound 2  | −45 | −93 | −47 |
| Compound 3  | −60 | −76 | −17 |
| Compound 4  | −61 | −89 | −45 |
| Compound 6  | −45 | −90 | −66 |
| Compound 8  | −59 | −82 | −20 |
| Compound 10 | −71 | −77 | −37 |
| Compound 13 | −75 | −92 | −38 |
| Compound 14 | −88 | −84 | −21 |
| Compound 15 | −66 | −80 | −36 |
| Compound 16 | −76 | −63 | −9  |
| Compound 17 | −78 | −90 | −25 |
| Compound 18 | −72 | −61 | 3   |
| Compound 19 | −56 | −42 | −4  |
| Compound 20 | −88 | −16 | 16  |
| Compound 22 | −87 | −82 | −24 |
| Compound 23 | −79 | −67 | 7   |
| Compound 24 | −75 | −79 | −6  |
| Compound 25 | −80 | −96 | −49 |
| Compound 35 | −77 | −69 | −20 |
| Compound 37 | −82 | −89 | −29 |
| Compound 38 | −81 | −66 | −2  |
| Compound 41 | −88 | −76 | −15 |
| Compound 42 | −86 | −77 | −25 |
| Compound 43 | −78 | −94 | −31 |

TABLE 7

Acute food intake in rat after a single s.c. administration of amylin comparator compounds (3 nmol/kg). A negative value indicates reduced food intake relative to vehicle whereas a positive value indicates increased food intake relative to vehicle.

| Special feature of comparator | Food intake relative to vehicle (%) 0-24 hr, 3 nmol/kg | Food intake relative to vehicle (%) 24-48 hr, 3 nmol/kg | Food intake relative to vehicle (%) 48-72 hr, 3 nmol/kg |
|---|---|---|---|
| Amylin receptor agonist (RA) in development | −42 | −38 | 3 |

Amylin comparator compound cagrilintide (Table 7) comprises a peptide according to SEQ ID NO: 34 and is further disclosed in WO 2012/168432.

Following dosing of amylin analogues to rats, it was observed that many of them induced a profound food intake inhibition, compared with vehicle treatment, as can be deduced from the data presented in Table 6. In general, the compounds in Table 6 showed improved reduction in food intake compared to the comparator cagrilintide (Table 7).

The compounds listed in Table 6 are all compounds according to the invention.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. An amylin receptor agonist according to Formula I (SEQ ID NO: 36):

$$AX_2X_3LX_5TX_7QTX_{10}RLAEFLHHX_{19}X_{20}X_{21}X_{22}FGX_{25}IX_{27}X_{28}X_{29}TX_{31}VGX_{34}X_{35}TX_{37},$$

wherein
- $X_2$ is S or G,
- $X_3$ is H, S, Q, or E,
- $X_5$ is S,
- $X_7$ is A,
- $X_{10}$ is Q or A,
- $X_{19}$ is S or absent,
- $X_{20}$ is S or absent,
- $X_{21}$ is D or absent,
- $X_{22}$ is N, P or absent,
- $X_{25}$ is A or P,
- $X_{27}$ is L or P,
- $X_{28}$ is S or P,
- $X_{29}$ is S or P,
- $X_{31}$ is D,
- $X_{34}$ is S or P,
- $X_{35}$ is N, D, or E, and
- $X_{37}$ is P.

2. The amylin receptor agonist according to claim 1, wherein
$X_{27}X_{28}X_{29}$ is selected from LPP or PSS.

3. The amylin receptor agonist according to claim 2, comprising a peptide selected from the following:

```
                                            (SEQ ID NO: 13)
AGELSTAQTARLAEFLHHFGPILPPTDVGSETP, (SEQ ID NO: 16)
ASQLSTAQTARLAEFLHHSSDNFGPILPPTDVGSNTP,
and (SEQ ID NO: 19)
ASHLSTAQTARLAEFLHHSSDPFGAIPSSTDVGPDTP,
``` wherein the peptide comprises a C-terminal amide.

4. The amylin receptor agonist according to claim 1, further comprising a protraction moiety.

5. The amylin receptor agonist according to claim 4, wherein the protraction moiety represented by formula (A)-(B) is attached via linker (A) to the alpha position of the A at position 1.

6. The amylin receptor agonist according to claim 5, wherein the amino acid at position 25 is A or P when the protraction moiety is attached to the A at position 1.

7. The amylin receptor agonist according to claim 5, wherein protractor (B) of the protraction moiety represented by formula (A)-(B) comprises a C-14 diacid, C-16 diacid, C-18 diacid, or C-20 diacid.

8. The amylin receptor agonist according to claim 5, wherein the linker (A) of the protraction moiety comprises a moiety according to Chem. 8a:

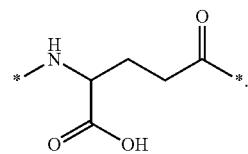

9. The amylin receptor agonist according to claim 7, selected from the following:

Compound 16

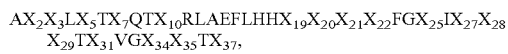

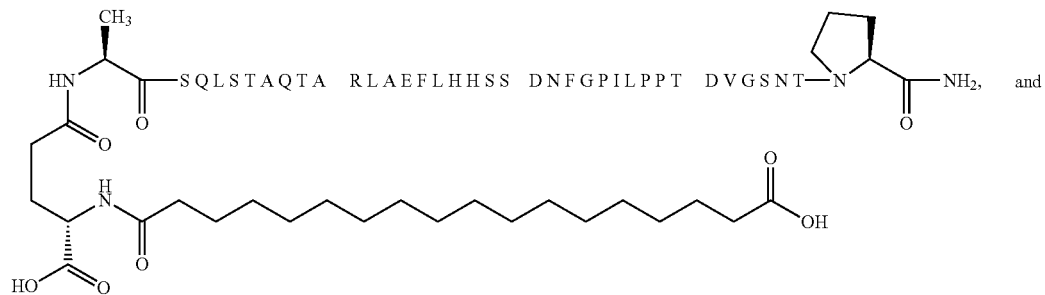

Compound 22

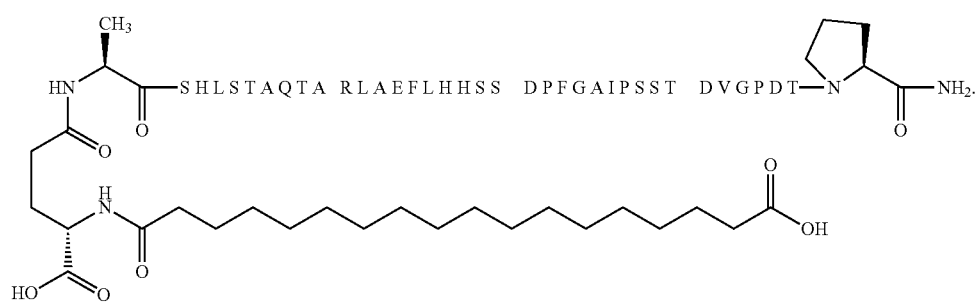

Compound 25

10. A pharmaceutical composition comprising the amylin receptor agonist according to claim 1, one or more pharmaceutically acceptable excipients, and/or pharmaceutically acceptable salt, ester, or amide forms thereof.

11. A pharmaceutical composition comprising the amylin receptor agonist peptide according to claim 3, one or more pharmaceutically acceptable excipients, and/or pharmaceutically acceptable salt, ester, or amide forms thereof.

12. A pharmaceutical composition comprising the amylin receptor agonist according to claim 9, one or more pharmaceutically acceptable excipients, and/or pharmaceutically acceptable salt, ester, or amide forms thereof.

13. A method of treating diabetes, cardiovascular disease, non-alcoholic steatohepatitis (NASH), cognitive impairment, and/or a Body Mass Index (BMI) of 27 or more, comprising administering to a subject in need of such treatment a pharmaceutically effective amount of the pharmaceutical composition according to claim 10.

14. A method of treating diabetes, cardiovascular disease, NASH, cognitive impairment, and/or a BMI of 27 or more, comprising administering to a subject in need of such treatment a pharmaceutically effective amount of the pharmaceutical composition according to claim 11.

15. A method of treating diabetes, cardiovascular disease, NASH, cognitive impairment, and/or a BMI of 27 or more, comprising administering to a subject in need of such treatment a pharmaceutically effective amount of the pharmaceutical composition according to claim 12.

* * * * *